United States Patent [19]
Kamboj et al.

[11] Patent Number: 6,136,544
[45] Date of Patent: Oct. 24, 2000

[54] GLUTAMATE RECEPTOR (OR EAA RECEPTOR) POLYNUCLEOTIDES AND THEIR USES

[75] Inventors: Rajender Kamboj, Mississauga, Canada; Stephen Nutt, Vienna, Austria

[73] Assignee: Allelix Biopharmaceuticals Inc., Ontario, Canada

[21] Appl. No.: 08/666,221

[22] Filed: Jun. 20, 1996

Related U.S. Application Data

[63] Continuation-in-part of application No. PCT/CA94/00705, Dec. 21, 1994, which is a continuation-in-part of application No. 08/172,188, Dec. 23, 1993, abandoned.

[51] Int. Cl.$^7$ .......................... C07K 14/705; C12N 15/12
[52] U.S. Cl. ........................... 435/7.1; 435/7.2; 435/69.1; 435/252.3; 435/320.1; 530/350; 536/23.5
[58] Field of Search ................................. 435/6, 7.1, 7.2, 435/69.1, 252.3, 320.1; 530/350; 536/23.5

[56] References Cited

FOREIGN PATENT DOCUMENTS

| | | |
|---|---|---|
| 0 568 384 A1 | 11/1993 | European Pat. Off. . |
| 0 574 257 A2 | 12/1993 | European Pat. Off. . |
| 0 578 409 A2 | 1/1994 | European Pat. Off. . |
| 0 617 123 A1 | 9/1994 | European Pat. Off. . |

OTHER PUBLICATIONS

McNamara et al, *J. of Neuroscience* 112(7): 2555–2562, Jul. 1992.
Backus et al Nucleic Acids Res, 1992, 20(22):6007 "Three distinct TNA sequence elements are requuired for efficient apolipoprotein B (apoB) RNA editing in vitro".
Boulter et al Science, 1990, 249:1033 "Molecular cloning and functional expression of glutamate receptor subunit genes".
Burnashev et al Science, 1992, 256:1566 "Calcium–permeable cerebellar glial cells".
Burnashev et al Neuron, 1992, 8:189 "Divalent ion permeability of AMPA receptor channels is dominated by the edited form of a single subunit".
Cech et al Cell, 1991, 64:667 "RNA editing: World's smallest introns".
Choi et al Neuron, 1988, 1:623 "Glutamate neurotoxicity and diseases of the nervous system".
Egegjerg et al Proc Natl Acad Sci USA, 1993, 90:755 "$Ca^{2+}$ permeability of unedited and edited versions of the kainate selective glutamate receptor GluR6".
Greenamyre J Neuroscience, 1987, 7(4):1022 "Evidence for transient perinatel glutamatergic innervation of Globus Pallidus".
Harris et al J Biol Chem, 1993, 268(10):7382 "Extract–specific heterogeneity in high–order complexes containing apolipoprotein BmRNA editing activity and RNA–binding proteins".
Higuchi et al Cell, 1993, 75:1361 "RNA editing of AMPA receptor subunit GluR–B: A base–paired intron–exon structure determines positon and efficiency".
Hollman et al Science, 1991, 252:851 "Ca2+ permeability of KA–AMPA–gated glutamate receptor channels depends on subunit composition".

Hollman et al Nature, 1989, 342:643 "Cloning by functional expression of a member of the glutamate receptor family".
Hume et al Science, 1991, 253:1028 "Identification of a site in glutamate receptor subunits that controls calcium permeability".
Jonas et al J Physiology, 1992, 455:143 "Glutamate receptor channels in isolated patches from CA1 and CA3pyramidal cells of rat hippocamal slices".
Keinanen et al Science, 1990, 249:556 "A family of AMPA–selective glutamate receptors".
Kohler et al Neuron, 1993, 10:491 "Determinants of Ca2+ permeability in both TM1 and TM2 of high affinity kainate receptor channels: diversity by RNA editing".
McLaughlin etal European Journal of Pharmacology 244:89–92 (1993) "Expression of alternatively–spliced glutamate receptors in human hippocampus".
Monyer et al Neuron, 1991, 6:799 "Glutamate–operated channels: developmentally early and mature forms arise by alternative splicing".
Muller et al Science, 1992, 256:1563 "Calcium entry through kainate receptors and resulting potassium–channel blockade in Bergman glial cells".
Nakanishi et al Neuron, 1990, 5:569 "A family of glutamate receptor genes: evidence for the formation of heteromultimeric receptors with distinct channel properties".
Navaratnam J Biol Chem, 1993, 268(28):20709 "The p27 catalytic subunit of the apolipoprotein B mRNA editing enzyme is a cytidine deaminase".
Rothman et al Ann Neurol, 1986, 19:105 "Glutamate and the pathophysiology of hypoxic–ischemic brain damage".
Sakamura et al FEBS, 1990, 272:73 "Functional expression from cloned cDNAs of glutamate receptror species responsive to kainate and quisqualate".
Sommer et al Cell, 1991, 67:11 "RNA editing in brain controls a determinant of ion flow in glutamate–gated channels".
Sun et al Proc Natl Acad Sci USA, 1992, 89:1443 "Molecular cloning, chromosomal mapping, and functional expression of human brain glutamate receptors".
Teng et al Science, 1993, 260:1816 "Molecular cloning of an apolipoprotein B messinger RNA editing protein".
Teng et al J Biol Chem, 1990, 265(33):20616 "Apolipoprotein B messenger RNA editing is developmentally regulated and widely expressed in human tissues".
Verdoorn et al Science, 1991, 252:1715 "Structural determinants of ion flow through recombinant glutamate receptor channels".
Wu et al J Biol Chem, 1990, 265:12312 "Apolipoprotein B mRNA editing".

*Primary Examiner*—John Ulm
*Attorney, Agent, or Firm*—Foley & Lardner

[57] ABSTRACT

Human CNS receptor-encoding DNA is provided from which more than one form of the receptor protein, an edited form and an unedited form, is expressed in vivo. The edited and unedited receptor forms are functionally distinct, and appear to be selectively expressed. Thus, a CNS receptor-encoding gene that is subject to such editing has value in screening compounds for potential therapeutic utility.

24 Claims, 35 Drawing Sheets

FIG. IA-I

```
    EcoRI
    GAATTCCGTGAGTGCATGGGAGGTGCTGATATTCCGAGACACTGGGACCACAGCGGCA
1   ----------+---------+---------+---------+---------+---------+   60
    CTTAAGGCACTCACGTACCCTCCACGACTATAAGGCTCTGTGACCCTGGTGTCGCCGT

GCTCCGCTGAAAACTGCATTCAGCCAGTCCTCCGGACTTCTGGAGCGGGACAGGGCGCA
61  ----------+---------+---------+---------+---------+---------+   120
    CGAGGCGACTTTTGACGTAAGTCGGTCAGGAGGCCTGAAGACCTCGCCCCTGTCCCGCGT

GGGCATCAGCAGCCACCAGCAGGACCTGGGAAATAGGATTCTTCTGCCTCCACTTCAGG
121 ----------+---------+---------+---------+---------+---------+   180
    CCCGTAGTCGTCGGTGGTCCTGGACCCTTTATCCTAAGAAGACGGAGGTGAAGTCC

TTTTAGCAGCTTGGTGTCTAAATTGCTGTGTCTCAAAATGCAGAGGATCTAATTGCAGAGGA
181 ----------+---------+---------+---------+---------+---------+   240
    AAAATCGTCGAACCACGATTTAACGACACAGAGTTTTACGTCTCCTAGATTAAACGTCTCCT

AAACAGCCAAAGAAGGAAGAGGAGGAAAAAAAGGGGTATATTGTGGATGCTC
241 ----------+---------+---------+---------+---------+---------+   300
    TTTGTCGGTTTCTTCCTTCTCCTCCTTTTTTTTCCCCATATAACACCTACGAG

TACTTTTCTTGGAAATGCAAAAGATTATGCATATTTCTGTCCTCCTTTCCTCCTGTTTTAT
301 ----------+---------+---------+---------+---------+---------+   360
    ATGAAAAGAACCTTTACGTTTTCTAATACGTATAAAGACAGGAGGAAAGAGGACAAAATA

M  Q  K  I  M  H  I  S  V  L  L  S  P  V  L  W    -5

GGGGACTGATTTTGGTCTCTTCTAACAGCATACAGATAGGGGGGCTATTCCTAGGG
361 ----------+---------+---------+---------+---------+---------+   420
    CCCCTGACTAAAACCAGAGAAGATTGTCGTATGCTGTCTATCCCCCCGATAAAGGATCCC
```

FIG. IA-2

```
       G   L   I   F   G₁  V   S   S   N   S   I   Q   I   G   G   L   F   P   P   R   G    16
                       |___Mature N-Terminal
     GCGCCGATCAAGAATACAGTGCATTTCGAGTAGGATGGTTCAGTTTTCCACTTCGGAGT
421  ------+---------+---------+---------+---------+---------+   480
     CGCGGCTAGTTCTTATGTCACGTAAAGCTCATCCTACCAAGTCAAAAGGTGAAGCCTCA A   D   Q   E   Y   S   A   F   R   V   G   M   V   Q   F   S   T   S   E   F    36
     TCAGACTGACACCCCACATCGACAATTGGAGGTGGCAAACAGCTTGCCAGTCACTAATG
481  ------+---------+---------+---------+---------+---------+   540
     AGTCTGACTGTGGGGTGTAGCTGTTAACCTCCACCGTTTGTCGAACGGTCAGTGATTAC R   L   T   P   H   I   D   N   L   E   V   A   N   S   F   A   V   T   N   A    56
     CTTTCTGCTCCCAGTTTTCGAGAGGAGTCTATGCTATTTTTGGATTTTATGACAAGAAGT
541  ------+---------+---------+---------+---------+---------+   600
     GAAAGACGAGGGTCAAAAGCTCTCCTCAGATACGATAAAAACCTAAAATACTGTTCTTCA F   C   S   Q   F   S   R   G   V   Y   A   I   F   G   F   Y   D   K   K   S    76
     CTGTAAATACCATCACATCATTTGCGGAACACTCCACGTCTCCTTCATCACTCCCAGCT
601  ------+---------+---------+---------+---------+---------+   660
     GACATTTATGGTAGTGTAGTAAACGCCTTGTGAGGTGCAGAGGAAGTAGTGAGGGTCGA V   N   T   I   T   S   F   C   G   T   L   H   V   S   F   I   T   P   S   F    96
```

```
661  TCCCAACAGATGGCACACATCCATTGTCATTCAGATGAGACCCGACCTCAAAGGAGCTC
     ----+----+----+----+----+----+----+----+----+----+----+----+  720
     AGGGTTGTCTACCGTGTGTAGGTAACAGTAGTCTACTCTGGGCTGGAGTTTCCTCGAG
      P  T  D  G  T  H  P  F  V  I  Q  M  R  P  D  L  K  G  A  L   116

721  TCCTTAGCTTGATTGAATACTATCAATGGGACAAGTTTGCATACCTCTATGACAGTGACA
     ----+----+----+----+----+----+----+----+----+----+----+----+  780
     AGGAATCGAACTAACTTATGATAGTTACCCTGTTCAAACGTATGGAGATACTGTCACTGT
      L  S  L  I  E  Y  Y  Q  W  D  K  F  A  Y  L  Y  D  S  D  R   136

781  GAGGCTTATCAACACTGCAAGCTGTGCTGGATTCTGCTGAAAAGAAATGGCAAGTGA
     ----+----+----+----+----+----+----+----+----+----+----+----+  840
     CTCCGAATAGTTGTGACGTTCGACACGACCTAAGACGACTTTTCTTTACCGTTCACT
      G  L  S  T  L  Q  A  V  L  D  S  A  A  E  K  K  W  Q  V  T   156

841  CTGCTATCAATGTGGGAAACATTAACAATGACAAGAAGATGAGATGTACCGATCACTTT
     ----+----+----+----+----+----+----+----+----+----+----+----+  900
     GACGATAGTTACACCCTTGTAATTGTTACTGTTCTTCTACTCTACATGGCTAGTGAAA
      A  I  N  V  G  N  I  N  N  D  K  K  D  E  M  Y  R  S  L  F   176

901  TTCAAGATCTGGAGTTAAAAAAGGAACGGCGTGTAATTCTGGACTGTGAAAGGGATAAAG
     ----+----+----+----+----+----+----+----+----+----+----+----+  960
     AAGTTCTAGACCTCAATTTTTCCTTGCCGCACATTAAGACCTGACACTTTCCCTATTTC
      Q  D  L  E  L  K  K  E  R  R  V  I  L  D  C  E  R  D  K  V   196
```

FIG. 1B-2

```
961  TAAACGACATTGTAGACCAGTTATTACCATTGGAAAACACGTTAAAGGGTACCACTACA
     ----+----+----+----+----+----+----+----+----+----+----+----+ 1020
     ATTTGCTGTAACATCTGGTCAATAATGGTAACCTTTTGTGCAATTTCCCATGGTGATGT

N  D  I  V  D  Q  V  I  T  I  G  K  H  V  K  G  Y  H  Y  I   216

1021 TCATTGCAAATCTGGGATTTACTGATGGAGACCTATTAAAAATCCAGTTTGGAGGTGCAA
     ----+----+----+----+----+----+----+----+----+----+----+----+ 1080
     AGTAACGTTTAGACCCTAAATGACTACCTCTGGATAATTTTAGGTCAAACCTCCACGTT

I  A  N  L  G  F  T  D  G  D  L  L  K  I  Q  F  G  G  A  N   236

1081 ATGTCTCTGGATTTCAGATAGTGGACTATGATGATTCGTTGGTATCTAAATTTATAGAAA
     ----+----+----+----+----+----+----+----+----+----+----+----+ 1140
     TACAGAGACCTAAAGTCTATCACCTGATACTACTAAGCAACCATAGATTTAAATATCTTT

V  S  G  F  Q  I  V  D  Y  D  D  S  L  V  S  K  F  I  E  R   256

1141 GATGGTCAACACTGGAAGAAAAAGAATACCCTGGAGCTCACACATGAAGTATA
     ----+----+----+----+----+----+----+----+----+----+----+----+ 1200
     CTACCAGTTGTGACCTTCTTTTTCTTATGGGACCTCGAGTGTGTTCATAT

W  S  T  L  E  E  K  E  Y  P  G  A  H  T  T  I  K  Y  T   276

1201 CTTCTGCTCTGACCTATGATGCCGTTCAAGTGATGACTGAAGCCTTCCGCAACCTAAGGA
     ----+----+----+----+----+----+----+----+----+----+----+----+ 1260
     GAAGACGAGACTGGATACTACGGCAAGTTCACTACTGACTTCGGAAGGCGTTGGATTCCT

```
      AGCAAAGAATTGAAATCTCCCGAAGGGGAATGCAGGAGACTGTCTGGCAAACCCAGCAG
1261  ------+---------+---------+---------+---------+---------+  1320
      TCGTTTCTTAACTTTAGAGGGCTTCCCCCTTACGTCCTCTGACAGACCGTTTGGGTCGTC
         Q   R   I   E   I   S   R   R   G   N   A   G   D   C   L   A   N   P   A   V     316

TGCCCTGGGGACAAGGTGTAGAAATAGAAAGGGCCCTCAAACAGGTTCAGGTTGAAGGTC
1321  ------+---------+---------+---------+---------+---------+  1380
      ACGGGACCCCTGTTCCACATCTTTATCTTTCCCGGGAGTTTGTCCAAGTCCAACTTCCAG
         P   W   G   Q   G   V   E   I   E   R   A   L   K   Q   V   Q   V   E   G   L     336

TCTCAGGAAATATAAAGTTTGACCAGAATGGGAAAAGAATAAACTATACAATTAACATCA
1381  ------+---------+---------+---------+---------+---------+  1440
      AGAGTCCTTTATATTTCAAACTGGTCTTACCCTTTTCTTATTTGATATGTTAATTGTAGT
         S   G   N   I   K   F   D   Q   N   G   K   R   I   N   Y   T   I   N   I   M     356

TGGAGCTCAAAACTAATGGGCCCCGGAAGATTGGCTACTGGAGTGAAGTGGACAAAATGG
1441  ------+---------+---------+---------+---------+---------+  1500
      ACCTCGAGTTTTGATTACCCGGGGCCTTCTAACCGATGACCTCACTTCACCTGTTTTACC
         E   L   K   T   N   G   P   R   K   I   G   Y   W   S   E   V   D   K   M   V     376

TTGTTACCCTTACTGAGCTCCCTTCTGGAAATGACACCTCTGGGCTTGAGAATAAGACTG
1501  ------+---------+---------+---------+---------+---------+  1560
      AACAATGGGAATGACTCGAGGGAAGACCCTTTACTGTGGAGACCCGAACTCTTATTCTGAC
         V   T   L   T   E   L   P   S   G   N   D   T   S   G   L   E   N   K   T   V     396
```

FIG. IC-2

```
1561  TTGTTGTCACCACAATTTGGAATCTCCGTATGTTATGATGAAGAAAAATCATGAAATGC
      ----------+---------+---------+---------+---------+---------+  1620
      AACAACAGTGGTGTTAAACCTTAGAGGCATACAATACTACTTCTTCTTTTAGTACTTTACG
       V  V  T  T  I  L  E  S  P  Y  V  M  M  K  K  N  H  E  M  L    416

1621  TTGAAGGCAATGAGCGCTATGAGGGCTACTGTGTTGACCTGGCTGCAGAAATCGCCAAAC
      ----------+---------+---------+---------+---------+---------+  1680
      AACTTCCGTTACTCGCGATACTCCCGATGACACAACTGGACCGACGTCTTTAGCGGTTTG
       E  G  N  E  R  Y  E  G  Y  C  V  D  L  A  A  E  I  A  K  H    436

1681  ATTGTGGGTTCAAGTACAAGTTGACAATTGTTGGTGATGGCAAGTATGGGGCCAGGGATG
      ----------+---------+---------+---------+---------+---------+  1740
      TAACACCCAAGTTCATGTTCAACTGTTAACAACCACTACCGTTCATACCCCGGTCCCTAC
       C  G  F  K  Y  K  L  T  I  V  G  D  G  K  Y  G  A  R  D  A    456

1741  CAGACACGAAATTTGGAATGGGATGGTTGGAGAACTTGTATATGGGAAAGCTGATATTG
      ----------+---------+---------+---------+---------+---------+  1800
      GTCTGTGCTTTTAAACCTTACCCTACCAACCTCTTGAACATATACCCTTTCGACTATAAC
       D  T  K  I  W  N  G  M  V  G  E  L  V  Y  G  K  A  D  I  A    476

1801  CAATTGCTCCATTAACTATTACCCTTGTGAGAGAAGAGGTGATTGACTTCTCAAAGCCCT
      ----------+---------+---------+---------+---------+---------+  1860
      GTTAACGAGGTAATTGATAATGGGAACACTCTCTTCTCCACTAACTGAAGAGTTTCGGGA
       I  A  P  L  T  I  T  L  V  R  E  E  V  I  D  F  S  K  P  F    496
```

FIG. ID-1

```
1861  TCATGAGCCTCGGGATATCTATCATGATCAAGAAGCCTCAGAAGTCCAAACCAGGAGTGT
      ------+---------+---------+---------+---------+---------+  1920
      AGTACTCGGAGCCCTATAGATAGTACTAGTTCTTCGGAGTCTTCAGGTTTGGTCCTCACA
       M   S   L   G   I   S   I   M   I   K   K   P   Q   K   S   K   P   G   V   F   516

1921  TTTCCTTTCTTGATCCTTTAGCCTATGAGATCTGGATGTGCATTGTTTTTGCCTACATTG
      ------+---------+---------+---------+---------+---------+  1980
      AAAGGAAAGAACTAGGAAATCGGATACTCTAGACCTACACGTAACAAAAACGGATGTAAC
       S   F   L   D   P   L   A   Y   E   I   W   M   C   I   V   F   A   Y   I   G   536

1981  GGGTCAGTGTAGTTTTATTCCTGGTCAGCAGATTAGCCCCTACGAGTGGCACACTGAGG
      ------+---------+---------+---------+---------+---------+  2040
      CCCAGTCACATCAAAATAAGGACCAGTCGTCTAAATCGGGATGCTCACCGTGTGACTCC
       V   S   V   V   L   F   L   V   S   R   F   S   P   Y   E   W   H   T   E   E   556

2041  AGTTTGAAGATGGAAGAGAAACACAAAGTAGTGAATCAACTAATGAATTTGGGATTTTA
      ------+---------+---------+---------+---------+---------+  2100
      TCAAACTTCTACCTTCTCTTTGTGTTTCATCACTTAGTTGATTACTTAAACCCTAAAAAT
       F   E   D   G   R   E   T   Q   S   S   E   S   T   N   E   F   G   I   F   N   576

2101  ATAGTCTCTGGTTTCCTTGGTGCCTTTATGCAGCAAGGATGCGATATTCGCCAAGAT
      ------+---------+---------+---------+---------+---------+  2160
      TATCAGAGACCAAAGGAACCACGGAAATACGTCGTTCCTACGCTATAAAGCGGTTCTA
       S   L   W   F   S   L   G   A   F   M   Q   Q   G   C   D   I   S   P   R   S   596
```

FIG. ID-2

```
      CCCTCTCTGGGCGCATTGTTGGAGGTGTGTGGTTCTTACCCTGATCATAATCTCT
2161  ------+---------+---------+---------+---------+---------+   2220
      GGGAGAGACCCGCGTAACAACCTCCACACACCACCAGAAATGGACTAGTATTAGAGGA

L  S  G  R  I  V  G  G  V  W  F  F  T  L  I  I  S  S      616

CCTACACGGCTAACTTAGCTGCCTTCCTGACTGTAGAGAGGATGGTGTCTCCCATCGAAA
2221  ------+---------+---------+---------+---------+---------+   2280
      GGATGTGCCGATTGAATCGACGGAAGGACTGACATCTCCTACCACAGAGGGTAGCTTT

Y  T  A  N  L  A  A  F  L  T  V  E  R  M  V  S  P  I  E  S  636

GTGCTGAGGATCTTTCTAAGCAAACAGAAATTGCTTATGGAACATTAGACTCTGGCTCCA
2281  ------+---------+---------+---------+---------+---------+   2340
      CACGACTCCTAGAAAGATTCGTTTGTCTTTAACGAATACCTTGTAATCTGAGACCGAGGT

A  E  D  L  S  K  Q  T  E  I  A  Y  G  T  L  D  S  G  S  T  656

CTAAAGAGTTTTTCAGGAGATCTAAAATTGCAGTGTTTGATAAAATGTGGACCTACATGC
2341  ------+---------+---------+---------+---------+---------+   2400
      GATTTCTCAAAAAGTCCTCTAGATTTTAACGTCACAAACTATTTTACACCTGGATGTACG

K  E  F  F  R  R  S  K  I  A  V  F  D  K  M  W  T  Y  M  R  676

GGAGTGCGGGAGCCCTCTGTGTTTGTGAGGACTACGGCCGAAGGGGTGGCTAGAGTGCGGA
2401  ------+---------+---------+---------+---------+---------+   2460
      CCTCACGCCTCGGGAGACACAAACACTCCTGATGCCGGCTTCCCCACCGATCTCACGCCT

```
     AGTCCAAAGGGAAATATGCCTACTGTGTTGGAGTCCACGATGAACGAGTACATTGAGCAAA
2461 ------------+------------+------------+------------+------------+------------+ 2520
     TCAGGTTTCCCTTTATACGGATGACACAACCTCAGGTGCTACTTGCTCATGTAACTCGTTT

S  K  G  K  Y  A  Y  L  L  E  S  T  M  N  E  Y  I  E  Q  R   716

GGAAGCCTTGCCGACACCATGAAAGTTGGTGTGGAAACCTGGATTCCAAAGGCTATGGCATCG
2521 ------------+------------+------------+------------+------------+------------+ 2580
     CCTTCGGAACGCTGTGGTACTTCAACCACCTTTGGACCTAAGGTTTCCGATACCGTAGC

K  P  C  D  T  M  K  V  G  G  N  L  D  S  K  G  Y  I  A   736

CAACACCTAAAGGATCCTCATTAGGAACCCCAGTAAATCTTGCAGTATTGAAACTCAGTG
2581 ------------+------------+------------+------------+------------+------------+ 2640
     GTTGTGGATTTCCTAGGAGTAATCCTTGGGGTCATTTAGAACGTCATAACTTTGAGTCAC

T  P  K  G  S  S  L  G  T  P  V  N  L  A  V  L  K  L  S  E   756

AGCAAGGCGTCTTAGACAAGCTGAAAAACAAATGGTGGTACGATAAAGGTGAATGTGGAG
2641 ------------+------------+------------+------------+------------+------------+ 2700
     TCGTTCCGCAGAATCTGTTCGACTTTTTGTTTACCACCATGCTATTTCCACTTACACCTC

Q  G  V  L  D  K  L  K  N  K  W  W  Y  D  K  G  E  C  G  A   776

CCAAGGACTCTGGAAGTAAGGAAAAGACCAGTGCCCTCAGTCTGAGCAACGTTGCTGGAG
2701 ------------+------------+------------+------------+------------+------------+ 2760
     GGTTCCTGAGACCTTCATTCCTTTTCTGGTCACGGGAGTCAGACTCGTTGCAACGACCTC

```
       TATTCTACATCCTTGTCGGGGCCTTGGTTTGGCAAATGCTGGTGTGGCTTTGATTGAGTTCT
2761   ------+---------+---------+---------+---------+---------+----  2820
       ATAAGATGTAGGAACAGCCCCGGAACCAAACGTTACGACCACCGAAACTAACTCAAGA

F  Y  I  L  V  G  G  L  G  L  A  M  L  V  A  L  I  E  F  C    816

GTTACAAGTCAAGGGCCGAGGCGAAACGAATGAAGGTGGCAAAGAATGCACAGAATATTA
2821   ------+---------+---------+---------+---------+---------+----  2880
       CAATGTTCAGTTCCCGGCTCCGCTTTGCTTACTTCCACCGTTTCTTACGTGTCTTATAAT

Y  K  S  R  A  E  A  K  R  M  K  V  A  K  N  A  Q  N  I  N    836
                        EcoRI
                        --

ACCCATCTTCCTCGCAGAATTCACAGAATTTGCAACTTATAAGGAAGGTTACAACGTAT
2881   ------+---------+---------+---------+---------+---------+----  2940
       TGGGTAGAAGGAGCGTCTTAAGTGTCTTAAACGTTGAATATCCTTCCAATGTTGCATA

P  S  S  Q  N  S  Q  N  F  A  T  Y  K  E  G  Y  N  V  Y      856

ATGGCATCGAAAGTGTTAAAATTTAGGGGATGACCTTGAATGATGCCATGAGGAACAAGG
2941   ------+---------+---------+---------+---------+---------+----  3000
       TACCGTAGCTTTCACAATTTTAAATCCCCTACTGGAACTTACTACGGTACTCCTTGTTCC

G  I  E  S  V  K  I  *    (SEQ ID No: 2)

CAAGGCTGTCAATTACAGGAAGTACTGGAGAAAATGGACGTGTTATGACTCCAGAATTTC
3001   ------+---------+---------+---------+---------+---------+----  3060
       GTTCCGACAGTTAATGTCCTTCATGACCTCTTTTACCTGCACAATACTGAGGTCTTAAAG
```

FIG. IF

```
3061 CCAAAGCNGTGCATGCTGTCCCTTACGTGAGTCCTGGCATGGGAATGAATGTCAGTGTGA 3120
     GGTTTCGNCACGTACGACAGGGAATGCACTCAGGACCGTACCCTTACTTACAGTCACACT

3121 CTGATCTCTCGTGATTGATAAGAACCTTTGAGTGCCTTACACAATGGTTTTCTTGTGTG 3180
     GACTAGAGAGCACTAACTATTCTTGGAAAACTCACGGAATGTGTTACCAAAGAACACAC
                                                         EcoRI

3181 TTTATTGTCAAAGTGGTGAGAGGCATCCAGTATCTTGAAGACTTTTCTTTCAGCCAAGAA 3240
     AAATAACAGTTTCACCACTCTCCGTAGGTCATAGAACTTCTGAAAGAAAGTCGGTTCTT

3241 TTCTTAAATATGTGGAGTTCATCTTGAATTGTAAGGAATGATTAATTAAAACACAACATC 3300
     AAGAATTTATACACCTCAAGTAGAACTTAACATTCCTTACTAATTAATTTTGTGTTGTAG

3301 TTTTTCTACTCGAGTTACAGACACAAAGCGTGGTGGACATGCACAGCTAACATGGAAGTACT 3360
     AAAAAGATGAGCTCAATGTCTGTGTTTCCGCACCACCCTGTACGTGTCGATTGTACCTTCATGA

3361 ATAATTACCTGAAGTCTTGTACAGACAACAAACCTGTTTCTGCAG 3407
     TATTAAATGGACTTCAGAAACATGTCTGTTGTTTGGACAAAGACGTC  (SEQ ID No: 1)
```

FIG. 5A-1

EcoRI

```
     1  GAATTCCGTCTCTTCTTTCCCCCTTTCCCTCTGTCTGTGCCTATCCCCGACTTTTGC      60
        CTTAAGGCAGAGAAAGGGGGAAAGGGAGACAGACACGGATAGGGGCTGAAAACG

61  ATCTGACCAAAGGACGAATGAGGGAGACGTTCCTGCAGATCGGGGCAGCAACTTCCTCA   120
        TAGACTGGTTCCTGCTTACTCCCTCTGCAAGGACGTCTAGCCCCGTCGTTGAAAGGAGT

121  GCTGGTCTCTGGGCTCCGGAGCCAGAGAGCGCTGATCCTCCCGTCTCTGCGGCCCATGAAG   180
        CGACCAGAGACCCGAGGCCTCGGTCTCTCGCGACTAGGAGGCGCAGACGCCGGGTACTTC

181  AGAGAGAGAGAGCCGTGATGGGCTAGCGACACAGCACTGAGGAGCCCCGAGAGAGCTCAGCCTT   240
        TCTCTCTCTCGGCACTACCCGATCGCTGTCGTGACTCCTCGGGCTCTCTCGAGTCGGAA

241  GCCAGCCAGCTCCGGCGGTCCCACGCGGTTCCCCTCGAGCTCGTCCGTGGGGAGCGCGCA   300
        CGGTCGGTCGAGGCGCCAGGTGCGCCAGGGTGCGCCAAGGAGCTCGAGGCGAGGCACCCCTCGCGT

301  GCGTGCTTGGAACCGGAGCATCCAGAGAGGATGAGGGCGGGGACCCGGCCCAAGTTGGGTG   360
        CGCACGAACCTTGGCCTCGTAGGTCTCTCCTACTCCGCCCCTGGCCGGGTTCAACCCAC

361  CATCTCTCGGGCTCCGGCAGCGGCTGTATCTCGGCATGAATTAAGAAGCTAGGAAGATG   420
        GTAGAGAGCCCCGAGGCCGTGCGCCAGGCCGACATAGAGCCGTACTTAATTCTTCGATCCTTCTAC
                                                                M     -30
```

FIG.5A-2

```
421 GAGCACGGCACACTCCTCGCCCAGCCCGGGCTCTGGACCAGGACACCAGCTGGGCACTC   480
    ---------+---------+---------+---------+---------+---------+
    CTCGTGCCGTGTGAGGAGCGGGTCGGGCCCGAGACCCTGGTCCCTGTGGTCGACCCGTGAG
-29  E  H  G  T  L  L  A  Q  P  G  L  W  T  R  D  T  S  W  A  L    -10

481 CTCTATTCCTCTGCTATATCCTCCCTCAGACCCGCCCCCCAAGTACTCAGGATCGGAGGG   540
    ---------+---------+---------+---------+---------+---------+
    GAGATAAGGAGACGATATAGGAGGGAGTCTGGGCGGGGGGTTCATGAGTCCTAGCCTCCC
-09  L  Y  F  L  C  Y  I  L  P  Q  T  A  P  Q  V  L  R  I  G  G     11
                                        |_ Mature Amino-Terminal 541 ATTTTTGAAACAGTGGAAAATGAGCCTGTTAATGTTGAAGAATTAGCTTTCAAGTTTGCA   600
    ---------+---------+---------+---------+---------+---------+
    TAAAAACTTTGTCACCTTTTACTCGGACAATTACAACTTCTTAATCGAAAGTTCAAACGT
 12  I  F  E  T  V  E  N  E  P  V  N  V  E  E  L  A  F  K  F  A     31

601 GTCACCAGCATTAACAGAAACAGAAACCCGAACCCTGATGCCTAACACCACATTAACCTATGACATC   660
    ---------+---------+---------+---------+---------+---------+
    CAGTGGTCGTAATTGTCTTTGTCTTTGGCTTGGGACTACGGATTGTGGTGTAATTGGATACTGTAG
 32  V  T  S  I  N  R  N  R  T  L  M  P  N  T  T  L  T  Y  D  I     51

661 CAGAGAATTAACCTTTTTGATAGTTTTGAAGCCTCGGAGAGCATGACCAGCTGGCT   720
    ---------+---------+---------+---------+---------+---------+
    GTCTCTTAATTGGAAAAACTATCAAAACTTCGGAGCCTCTCGTACACTGGTCGACCGA
 52  Q  R  I  N  L  F  D  S  F  E  A  S  R  R  A  C  D  Q  L  A     71

721 CTTGGTGTGGCTGCTGCTCTCTTTGGCCCTTCCCATAGCTCCTCCGTCAGTCTGTGCAGTCT   780
    ---------+---------+---------+---------+---------+---------+
    GAACCACCACCGACGAGAGAAACCGGGTATCGAGGAGGCAGTCAGACACGTCAGA
 72  L  G  V  A  A  L  F  G  P  S  H  S  S  S  V  S  A  V  Q  S     91
```

FIG. 5B-1

```
781  ATTGCAATGCTCTCGAAGTTCCACACATACAGACCCGCTGGAAACACCCCTCGGTGGAC  840
     ----+----|----+----|----+----|----+----|----+----|----+----|
     TAACGTTACGAGAGCTTCAAGGTGTGTATGTCTGGGCGACCTTTGTGGGAGCCACCTG
 92   I  C  N  A  L  E  V  P  H  I  Q  T  R  W  K  H  P  S  V  D   111

841  AACAAAGATTTGTTTTACATCAACCTTTACCCAGATTATGCAGCTATCAGCAGGGCGATC  900
     ----+----|----+----|----+----|----+----|----+----|----+----|
     TTGTTTCTAAACAAAATGTAGTTGGAAATGGGTCTAATACGTCGATAGTCGTCCCGCTAG
112   N  K  D  L  F  Y  I  N  L  Y  P  D  Y  A  A  I  S  R  A  I   130

901  CTGGATCTGGTCCTCTATTACAACTGGAAAACAGTGACAGTGGTGTATGAAGACAGCACA  960
     ----+----|----+----|----+----|----+----|----+----|----+----|
     GACCTAGACCAGGAGATAATGTTGACCTTTTGTCACTGTCACCACATACTTCTGTCGTGT
132   L  D  L  V  L  Y  Y  N  W  K  T  V  T  V  V  Y  E  D  S  T   150

961  GGTCTAATTCGTCTACAAGAGCTCATCAAGCTCCCTCCCAGATATATATTAAAATCAAA  1020
     ----+----|----+----|----+----|----+----|----+----|----+----|
     CCAGATTAAGCAGATGTTCTCGAGTAGTTCGAGGGAGGTCTATATATATAATTTAGTTT
152   G  L  I  R  L  Q  E  L  I  K  A  P  S  R  Y  N  I  K  I  K   170

1021 ATCCGCCAGCTGCCCTGGGAATAAAGATGCCAAGCCTTTACTCAAGGAGATGAAGAAA  1080
     ----+----|----+----|----+----|----+----|----+----|----+----|
     TAGGCGGTCGACGGGAGACCCTTATTTCTACGGTTCGGAAATGAGTTCCTCTACTTCTTT
172   I  R  Q  L  P  S  G  N  K  D  A  K  P  L  L  K  E  M  K  K   190

1081 GGCAAGGAGTTCTATGTGATATTTGATTGTTCACATGAAACAGCCGCTGAAATCCTTAAG  1140
     ----+----|----+----|----+----|----+----|----+----|----+----|
     CCGTTCCTCAAGATACACTATAAACTAACAAGTGTACTTTGTCGGCGACTTTAGGAATTC
192   G  K  E  F  Y  V  I  F  D  C  S  H  E  T  A  A  E  I  L  K   211

1141 CAGATTCGTGTTCATGGGCATGATGACCGAATACTATCACTACTTTTCACAACCCTGGAC  1200
     ----+----|----+----|----+----|----+----|----+----|----+----|
```

FIG. 5B-2

```
212  GTCTAAGACAAGTACCCGTACTACTGGCTTATGATAGTGATGAAAAAGTGTTGGGACCTG  231
     Q  I  L  F  M  G  M  M  T  E  Y  Y  H  Y  F  F  T  T  L  D

1201 TTATTTGCTTTGGATCTGGAACTCTATAGTGGCGTAAACATGACCGGGTTTGGG        1260
     AATAAACGAAACCTAGACCTTGAGATATCCATGTCACCGCATTTGTACTGGCCCAAACCC
232  L  F  A  L  D  L  E  L  Y  R  Y  S  G  V  N  M  T  G  F  G  251

1261 CTGCTTAACATTGACAACCCTCACGTGTCATCCATCATTGAGAAGTGTCCATGGAGAGA   1320
     GACGAATTGTAACTGTTGGGAGTGCACAGTAGGTAGTAACTCTTCACCAGTACCTCTCT
252  L  L  N  I  D  N  P  H  V  S  S  I  I  E  K  W  S  M  E  R  271

1321 CTGCAGGCCCCACCCGGAGACTGGCCCTTTTGGATGGCATGATGACAACTGAAGCG      1380
     GACGTCCGGGGTGGGCCTCTGACCGGGAAAACCTACCTACTACTGTTGACTTCGC
272  L  Q  A  P  P  R  P  E  T  G  L  L  D  G  M  M  T  T  E  A  291

1381 GCTCTGATGTACGATGCTGTGTACATGGTGGCCATTGCCTCGCACCGGGCATCCCAGCTG  1440
     CGAGACTACATGCTACGACACATGTACCACCGGTAACGGAGCGTGGCCGTAGGGTCGAC
292  A  L  M  Y  D  A  V  Y  M  V  A  I  A  S  H  R  A  S  Q  L  311

1441 ACCGTCAGCTCCCTGCAGTGCCATAGACATAAGCCATGGCGCCTCGGACCCAGATTTATG  1500
     TGGCAGTCGAGGGACGTCACGGTATCTGTATTCGGTACCGCGGAGCCTGGGTCTAAATAC
312  T  V  S  S  L  Q  C  H  R  H  K  P  W  R  L  G  P  R  F  M  331

1501 AACCTGATCAAAGAGGCCCGTGGGATGCCTTGACTGGGCATATCACCTTTAATAAAACC   1560
     TTGGACTAGTTTCTCCGGGCACCCTACCGAACTGACCCGTATAGTGGAAATTATTTTGG
332  N  L  I  K  E  A  R  W  D  G  L  T  G  H  I  T  F  N  K  T  351
```

FIG. 5C-1

```
1561 AATGGCTTGAGGAAGGATTTGATCTGGACATTATTAGTCTCAAAGAGGAAGGAACTGAA 1620
     ----+----+----+----+----+----+----+----+----+----+----+----+
     TTACCGAACTCCTTCCTAAACTAGACCTGTAATAATCAGAGTTTCTCCTTCCTTGACTT
352  N  G  L  R  K  D  F  D  L  D  I  I  S  L  K  E  E  G  T  E   371

1621 AAGATTGGGATTTGGAATTCCAACAGTGGGCTTAACATGACGGACAGCAACAAAGACAAG 1680
     ----+----+----+----+----+----+----+----+----+----+----+----+
     TTCTAACCCTAAACCTTAAGGTTGTCACCCGAATTGTACTGCCTGTCGTTGTTTCTGTTC
372  K  I  G  I  W  N  S  N  S  G  L  N  M  T  D  S  N  K  D  K   391

1681 TCCAGCAATATCACTGATTCATTGGCCAACAGAACACTCATTGTCACCACCATTCTGGAA 1740
     ----+----+----+----+----+----+----+----+----+----+----+----+
     AGGTCGTTATAGTGACTAAGTAACCGGTTGTCTTGTGAGTAACAGTGGTGGTAAGACCTT
392  S  S  N  I  T  D  S  L  A  N  R  T  L  I  V  T  T  I  L  E   411

1741 GAACCCTATGTTATGTACAGGAAATCTGATAAGCCTCTATATGGAAATGACAGATTTGAA 1800
     ----+----+----+----+----+----+----+----+----+----+----+----+
     CTTGGGATACAATACATGTCCTTTAGACTATTCGGAGATATACCTTTACTGTCTAAACTT
412  E  P  Y  V  M  Y  R  K  S  D  K  P  L  Y  G  N  D  R  F  E   431

1801 GGATATTGCCTAGACCTGTTGAAGAATTGTCAAACATCCTGGGTTTCATTTATGATGTT 1860
     ----+----+----+----+----+----+----+----+----+----+----+----+
     CCTATAACGGATCTGGACAACTTCTTAACAGTTTGTAGGACCCAAAGTAAATACTACAA
432  G  Y  C  L  D  L  L  K  E  L  S  N  I  L  G  F  I  Y  D  V   451

1861 AAACTAGTTCCCGATGGCAAATATGGGCCCAGAATGACAAAGGGGAGTGGAACGGGGATG 1920
     ----+----+----+----+----+----+----+----+----+----+----+----+
     TTTGATCAAGGGCTACCGTTTATACCCGGGTCTTACTGTTTCCCCTCACCTTGCCCTAC
452  K  L  V  P  D  G  K  Y  G  A  Q  N  D  K  G  E  W  N  G  M   471

1921 GTTAAAGAACTCATAGATCACAGGGCTGACCTGGCAGTGGCTCCTCTTACCATCACCTAC 1980
     ----+----+----+----+----+----+----+----+----+----+----+----+
```

FIG. 5C-2

```
1921  CAATTTCTGAGTATCTAGTGTCCCGACTGGACCGTCACCGAGGAGAATGGTAGTGGATG  1980
 472    V  K  E  L  I  D  H  R  A  D  L  A  V  A  P  L  T  I  T  Y   491

1981  GTGCGGGAGAAAGTCATTGACTTCTCCAAACCCTTCATGACCCTAGGCATCAGCATTCTC  2040
      CACGCCCTCTTTCAGTAACTGAAGAGGTTTGGGAAGTACTGGGATCCGTAGTCGTAAGAG
 492    V  R  E  K  V  I  D  F  S  K  P  F  M  T  L  G  I  S  I  L   511

2041  TACCGGAAGCCCAATGGTACCAATCCAGGCGTTTCTCCTTCCTCAACCCCTGTCTCCA    2100
      ATGGCCTTCGGGTTACCATGGTTAGGTCCGCAAAGAGGAAGGAGTTGGGGACAGAGGT
 512    Y  R  K  P  N  G  T  N  P  G  V  F  S  F  L  N  P  L  S  P   531

2101  GATATTTGGATGTATGTGCTCTTAGCCTGCTTGGGAGTCAGCTGTGTACTCTTTGTGATT  2160
      CTATAAACCTACATACACGAGAATCGGACGAACCCTCAGTGCGACACATGAGAAACACTAA
 532    D  I  W  M  Y  V  L  L  A  C  L  G  V  S  C  V  L  F  V  I   551

2161  GCAAGGTTTACACCCTACGAGTGGTATAACCCCATGCAACCCTGACTCAGACGTg       2220
      CGTTCCAAATGTGGGATGCTCACCATATTGGGGTACGTTGGGACTGAGTCTGCAC
 552    A  R  F  T  P  Y  E  W  Y  N  P  H  P  C  N  P  D  S  D  V   571

2221  GTGGAAAACAATTTACTTTACTAAATAGTTTCTGGTTTGGAGTTGGAGCTCTCATGCAG   2280
      CACCTTTTGTTAAATGAAATGATTTATCAAAGACCAAACCTCAACCTCGAGAGTACGTC
 572    V  E  N  N  F  T  L  L  N  S  F  W  F  G  V  G  A  L  M  Q   591

2281  CAAGGATCAGAGCTGATGCCCAAAGCTCTATCGACGAATAGTTGGAGGATATGGTGG    2340
      GTTCCTAGTCTCGACTACGGGTTTCGAGATAGCTGGTCTTATCAACCTCCCTATACCACC
 592    Q  G  S  E  L  M  P  K  A  L  S  T  R  I  V  G  G  I  W  W   611
```

FIG. 5D-1

```
2341 TTTTCACCCTAATCATCATTTCATCCTACACGGCCAATCTGGCTGCCTTCTTGACAGTA 2400
     AAAAGTGGGATTAGTAGTAGTAAAGTAGGATGTGCCGGTTAGACCGACGGAAGAACTGTCAT
 612 F  F  T  L  I  I  I  S  S  Y  T  A  N  L  A  A  F  L  T  V  631

2401 GAGAGAATGGAATCCCCATAGATTCGGCAGATGATCTGGCAAAGCAAACCAAGATAGAA 2460
     CTCTCTTACCTTAGGGGTATCTAAGCCGTCTACTAGACCGTTTCGTTTGGTTCTATCTT
 632 E  R  M  E  S  P  I  D  S  A  D  D  L  A  K  Q  T  K  I  E  651

2461 TATGGGGCGGTTAGAGATGGATCAACACAATGACCTTCTTCAAGAAATCAAAAATCTCCACC 2520
     ATACCCCGCCAATCTCTACCTAGTTGTTACTGGAAGAAGTTCTTAGTTTTTAGAGGTGG
 652 Y  G  A  V  R  D  G  S  T  M  T  F  F  K  K  S  K  I  S  T  671

2521 TATGAGAAGATGTGGGCTTTCATGAGCAGGAGCAGCAGACCGCCCTGGTAAGAAACAGT 2580
     ATACTCTTCTACACCCGAAAGTACTCGTCCTCGTCGTCTGCGGGACCATTCTTTGTCA
 672 Y  E  K  M  W  A  F  M  S  S  R  Q  Q  T  A  L  V  R  N  S  691

2581 GATGAGGGGATCCAGAGAGTGCTCACCACAGACTACGGCTGATGGAGTCCACCAGC 2640
     CTACTCCCCTAGTCTCTCACGAGTGGTGTCTGATGCCGACGACTACCTCAGGTGGTCG
 692 D  E  G  I  Q  R  V  L  T  T  D  Y  A  L  L  M  E  S  T  S  711

2641 ATTGAGTATGTGACGCAGAGAAACTGCAACCTCACTCAGATCGGGGGCCTCATTGACTCC 2700
     TAACTCATACACTGCGTCTCTTTGACGTTGGAGTGAGTCTAGCCCCGGAGTAACTGAGG
 712 I  E  Y  V  T  Q  R  N  C  N  L  T  Q  I  G  G  L  I  D  S  731

2701 AAAGGTTACGGAGTGGGAACACCTATTGGTTCTCCTTACCGGGATAAAATTACTATTGCT 2760
```

FIG. 5D-2

```
732  TTTCCAATGCCTCACCCTGTGGATAACCAAGAGGAATGGCCCTATTTAATGATAACGA  751
      K  G  Y  V  G  T  P  I  G  S  P  Y  R  D  K  I  T  I  A

2761 ATTCTTCAACTCCAAGAAGAAGGAAGCTGCATATGATGAAAGAGAAGTGGTGGCGTGGG  2820
2821 TAAGAAGTTGAGGTTCTTCTTCCCTTCGACGTATACTACTTTCTCTTCACCACCGCACCC  2880
752   I  L  Q  L  Q  E  E  G  K  L  H  M  M  K  E  K  W  W  R  G  771

2821 AATGGCTGCCCCGAGGAAGACAACAAAGAAGCCAGTGCCCTGGGAGTGGAAAATATTGGA  2880
2881 TTACCGACGGGGCTCCTTCTTGTTGTTTCTTCGGTCACGGGACCCTCACCTTTTATAACCT  2940
772   N  G  C  P  E  E  D  N  K  E  A  S  A  L  G  V  E  N  I  G  791

2881 GGCATCTTCATTGTTCTCGGCTGCCCGACTGGTCCTTTCTGTATTTGTAGCTATTGGAGAA  2940
2941 CCGTAGAAGTAACAAGACCGACGGCCTGACCAGGAAAGACATAAACATCGATAACCTCTT  3000
792   G  I  F  I  V  L  A  A  G  L  V  L  S  V  F  V  A  I  G  E  811

2941 TTCATATACAAATCACGGAAGAATAATGATATTGAACAGTGTCTCTCTTTCAACGCTATC  3000
3001 AAGTATATGTTTAGTGCCTTCTTAGAGTGACTTCTATAACTATAACTTGTCACAGAGAGAAAGTTGCGATAG  3060
812   F  I  Y  K  S  R  K  N  N  D  I  E  Q  C  L  S  F  N  A  I  831

3001 ATGGAAGAACTGGGAATCTCACTGAAGAATCAGAAAAAATAAGAAAAAGTCAAGAACT  3060
3061 TACCTTCTTGACCCTTAGACTGACTTCTTAGTCTTTTTATTCTTTTTCAGTTCTTGA  3120
832   M  E  E  L  G  I  S  L  K  N  Q  K  K  I  K  K  S  R  T  851

3061 AAGGGGAAATCTTCCTTCACAAGTATCCTTACTTGTCATCAGAGACGAACTCAGAGAAAA  3120
     TTCCCCTTTAGAAGGAAGTGTTCATAGGAAGTAGTGTTCTTGCTTGAGTCTCTTTT
852   K  G  K  S  S  F  T  S  I  L  T  C  H  Q  R  R  T  Q  R  K  871
```

FIG. 5E

```
3121  GAGACTGTGGCGTGATCCAAGGAAACGCCTGTAGGAAGAAAAAGGATGCATTCCCTACAG  3180
      ---------+---------+---------+---------+---------+---------+
      CTCTGACACCGCACTAGGTTCCTTTGCGGACATCCTTCTTTTTCCTACGTAAGGGATGTC
 872   E  T  V  A  875

3181  ATTTTGGAGAAAGGATTTCTGAGGAGTTGTGTGATGTGTTTCCATATATCTATATCCAT  3240
      ---------+---------+---------+---------+---------+---------+
      TAAAAACCTCTTTCCTAAAGACTCCTCAACACTACACAAAGGTATATAGATATAGGTA

3241  AACTCTGATTATGAATACAGATATAAGAAATACAAAAGTTTAAAAAGCTCACATAGATAT  3300
      ---------+---------+---------+---------+---------+---------+
      TTGAGACTAATACTTATGTCTATATTCTTTATGTTTCAAATTTTTCGAGTGTATCTATA

3301  GACTTGGGAAGTGACACCAGTTCTCTTTTAAAATAAAATTTGTATGCACAAAAAAAAAAA  3360
      ---------+---------+---------+---------+---------+---------+
      CTGAACCCTTCACTGTGGTCAAGAGAAAATTTATTTTAAACATACGTGTTTTTTTTTTTT

EcoRI
                    --
3361  AAAAAAAAAAAAAAAAAAAAAGGAATTC  3385
      ---------+---------+--------
      TTTTTTTTTTTTTTTTTTTTTCCTTAAG
```

FIG. 6A-1

```
                                                                    60
 1   GAATTCCCTCTCTATGACCATGCCGTGATCGTGTCTGCGGTCACCACTCGACGCATCCTC
     CTTAAGGGAGAGATACTGGTACGGCACTAGCACAGACGCCAGTGGTGAGCTGCGTAGGAG 120
61   ATTTCTACCCGAACCCAGGAGCCGAACGCTAGATCGGGAAGTGGGTGCCGTGCGTGTGG
     TAAAGATGGGCTTGGGTCCTCGGCTTGCGATCTAGCCCCTTCACCCACGGCACGCACACC 180
121  GCACAGAAACACCATGAAGATTATTTTCCCGATTCTAAGTAATCCAGTCTTCAGGCGCAC
     CGTGTCTTTGTGGTACTTCTAATAAAAGGGCTAAGATTCATTAGGTCAGAAGTCCGCGTG
                              M   K   I   I   F   P   I   L   S   N   P   V   F   R   R   T   -20

240
181  CGTTAAACTCCTGCTCTGTTTACTGTGGATTGGATATATTCTCAAGGAACCACACATGTATT
     GCAATTTGAGGACGAGAGACAAATGACACCTAACCTATAAGAGTTCCTTGGTGTGTACATAA
      V   K   L   L   L   C   L   L   W   I   G   Y   S   Q   G   T   T   H   V   L   1
                                                                           Mature N-terminus
                                                                           |--->

300
241  AAGATTGGTGGTATTTTTGAATATGTGGAATCTGGCCCAATGGGAGCTGAGGAACTTGC
     TTCTAACCACCATAAAAACTTATACACCTTAGACCGGGTTACCCTCGACTCCTTGAACG
      R   F   G   G   I   F   E   Y   V   E   S   G   P   M   G   A   E   E   L   A   21
```

FIG. 6A-2

```
     ATTCAGATTTGCTGTGAACACAATTAACAGAAACAGAACATTGCTACCCAATACTACCCT
301  ------------+---------+---------+---------+---------+---------+ 360
     TAAGTCTAAACGACACTTGTGTTAATTGTCTTTGTCTTGTAACGATGGGTTATGATGGGA
       F  R  F  A  V  N  T  I  N  R  N  R  T  L  L  P  N  T  T  L    41

TACCTATGATACCCAGAAGATAAACCTTTATGATAGTTTTGAAGCATCCAAGAAAGCCTG
361  ------------+---------+---------+---------+---------+---------+ 420
     ATGGATACTATGGGTCTTCTATTTGGAAATACTATCAAAACTTCGTAGGTTCTTTCGGAC
       T  Y  D  T  Q  K  I  N  L  Y  D  S  F  E  A  S  K  K  A  C    61

TGATCAGCTGTGTCTCTTGGGGTGGCTGCCATCTTCGGCCCTTCACACAGTCATCAGCAAA
421  ------------+---------+---------+---------+---------+---------+ 480
     ACTAGTCGACAGAGAACCCCACCGACGGTAGACGTTAGAAGCCCGGAAGTGTGTCAGTAGTCGTTT
       D  Q  L  S  L  G  V  A  A  I  F  G  P  S  H  S  S  A  N       81

CGGCAGTGCAGTCCATCTGCAATGCTCTCTGGGAGTTCCCCACATACAGACCCGCTGGAAGCA
481  ------------+---------+---------+---------+---------+---------+ 540
     GCCGTCACGTCAGGTAGACGTTACGAGACCCTCAAGGGGTGTATGTCTGGGCGACCTTCGT
       A  V  Q  S  I  C  N  A  L  G  V  P  H  I  Q  T  R  W  K  H   101

CCAGGTGTCAGACAACAAAGATTCCTTCTATGTCAGTCTCTACCCAGACTTCTCTTCACT
541  ------------+---------+---------+---------+---------+---------+ 600
     GGTCCACAGTCTGTGTTTCTAAGGAAGATACAGTCAGAGATGGGTCTGAAGAGAAGTGA
       Q  V  S  D  N  K  D  S  F  Y  V  S  L  Y  P  D  F  S  S  L   121
```

FIG. 6B-1

```
     CAGCCGTCGCCATTTTAGACCTGGTGCAGTTTTCAAGTGGAAAACCGTCACGGTTGTGTA
601  ------+---------+---------+---------+---------+---------+  660
     GTCGGCACGGTAAAATCTGGACCACGTCAAAAAGTTCACCTTTTGGCAGTGCCAACACAT

S   R   A   I   L   D   L   V   Q   F   F   K   W   K   T   V   V   Y    141

TGATGACAGCACTGGTCTCATTCGTTTGCAAGAGCTCATCAAAGCTCCATCAAGGTATAA
661  ------+---------+---------+---------+---------+---------+  720
     ACTACTGTCGTGACCAGAGTAAGCAAACGTTCTCGAGTAGTTCGAGGTAGTTCCATATT

D   D   S   T   G   L   I   R   L   Q   E   L   I   K   A   P   S   R   Y   N    161

TCTTCGACTCAAAATTCGTCAGTTACCTGCTGATACAAAGGATGCAAAACCCTTACTAAA
721  ------+---------+---------+---------+---------+---------+  780
     AGAAGCTGAGTTTTAAGCAGTCAATGGACGACTATGTTTCCTACGTTTTGGGAATGATTT

L   R   L   K   I   R   Q   L   P   A   D   T   K   D   A   K   P   L   L   K    181

AGAAATGAAAAGAGGCAAGGAGTTTCATGTAATCTTTGATTGTAGCCATGAAATGGCAGC
781  ------+---------+---------+---------+---------+---------+  840
     TCTTTACTTTTCTCCGTTCCTCCCTTCCTCAAAGTACATTAGAAACTAACATCGGTACTTTACCGTCG

E   M   K   R   G   K   E   F   H   V   I   F   D   C   S   H   E   M   A   A    201

AGGCATTTAAAACAGGCTATTAGCTATGGGAATGATGACAGAATACTATCATTATATCTT
841  ------+---------+---------+---------+---------+---------+  900
     TCCGTAAAATTTGTCCGTAATCGATACCCTTACTACTGTCTTATGATAGTAATATAGAA
```

FIG. 6B-2

```
      G  I  L  K  Q  A  L  A  M  G  M  M  T  E  Y  Y  H  Y  I  F     221
      TACCACTCTGGACCTCTCTTGCTCTCTTGATGTTGAGCCCTACCGATACAGTGGTGTTAACAT
 901  ---------+---------+---------+---------+---------+---------+    960
      ATGGTGAGACCTGGAGAAACGAGAACTACAACTCGGATGGCTATGTCACCACAATTGTA
      T  T  L  D  L  F  A  L  D  V  E  P  Y  R  Y  S  G  V  N  M     242

GACAGGGTTCAGAATATTAAATACAGAAAATACCCAAGTCTCCTCCATCATTGAAAAGTG
 961  ---------+---------+---------+---------+---------+---------+   1020
      CTGTCCCAAGTCTTATAATTTATGTCTTTTATGGGTTCAGAGGAGGTAGTAACTTTTCAC
      T  G  F  R  I  L  N  T  E  N  T  Q  V  S  S  I  I  E  K  W     261

GTCGATGGAACGATTGCAGGCACCTCCGAAACCCGATTCAGGTTTGCTGGATGGATTTAT
1021  ---------+---------+---------+---------+---------+---------+   1080
      CAGCTACCTTGCTAACGTCCGTGGAGGCTTTGGGCTAAGTCCAAACGACTACCTAAATA
      S  M  E  R  L  Q  A  P  P  K  P  D  S  G  L  L  D  G  F  M     281

GACGACTGATGCTGCTCTAATGTATGATGCTGTGCATGTGGTCTCTGTGGCCGTTCAACA
1081  ---------+---------+---------+---------+---------+---------+   1140
      CTGCTGACTACGACGAGATTACATACTACGACACGTACACCAGACAGCCGGCAAGTTGT
      T  T  D  A  A  L  M  Y  D  A  V  H  V  V  S  V  A  V  Q  Q     301

GTTTCCCCAGATGACAGTCAGTTCCTTGCAGTTGTAATCGACATAAACCCTGGCGCTTCGG
1141  ---------+---------+---------+---------+---------+---------+   1200
      CAAAGGGGTCTACTGTCAGTCAAGGAACGTCACATTAGCTGTATTTGGGACCGCGAAGCC
      F  P  Q  M  T  V  S  S  L  Q  C  N  R  H  K  P  W  R  F  G     321
```

FIG. 6C-1

```
1201 GACCCGCTTTATGAGTCTAATTAAAGAGGCACATTGGGAAGGCCTCACAGGCAGAATAAC
     ------+---------+---------+---------+---------+---------+ 1260
     CTGGGCGAAATACTCAGATTAATTTCTCCGTGTAACCCTTCCGGAGTGTCCGTCTTATTG

T  R  F  M  S  L  I  K  E  A  H  W  E  G  L  T  G  R  I  T   341

1261 TTTCAACAAAACCAATGGCTTGAGAACAGATTTGATTTGGATGTGATCAGTCTGAAGGA
     ------+---------+---------+---------+---------+---------+ 1320
     AAAGTTGTTTTGGTTACCGAACTCTTGTCTAAACTAAACCTACACTAGTCAGACTTCCT

F  N  K  T  N  G  L  R  T  D  F  D  L  D  V  I  S  L  K  E   361

1321 AGAAGGTCTAGAAAAGATTGGAACGTGGGATCCAGCCAGTGCCTGAATATGACAGAAAG
     ------+---------+---------+---------+---------+---------+ 1380
     TCTTCCAGATCTTTTCTAACCTTGCACCCTAGGTCGGTCACCGGACTTATACTGTCTTTC

E  G  L  E  K  I  G  T  W  D  P  A  S  G  L  N  M  T  E  S   381

1381 TCAAAAGGGAAAGCCAGCGAACATCACAGATTCCTTATCCAATCGTTCTTTGATTGTTAC
     ------+---------+---------+---------+---------+---------+ 1440
     AGTTTTCCCTTTCGGTCGCTTGTAGTGTCTAAGGAATAGGTTAGCAAGAAACTAACAATG

Q  K  G  K  P  A  N  I  T  D  S  L  S  N  R  S  L  I  V  T   401

1441 CACCATTTGGAAGAGCCTTATGTCCTTTTAAGAAGTCTGACAAACCTCTCTATGGTAA
     ------+---------+---------+---------+---------+---------+ 1500
     GTGGTAAACCTTCTCGGAATACAGGAAAATTCTTCAGACTGTTGGAGAGATACCATT

```
1501  TGATCGATTTGAAGGCTATTGCATTGATCTCCTCAGAGAGTTATCTACAATCCTTGGCTT
      ------+---------+---------+---------+---------+---------+  1560
      ACTAGCTAAACTTCCGATAACGTAACTAGAGGAGTCTCTCAATAGATGTTAGGAACCGAA

D   R   F   E   G   Y   C   I   D   L   L   R   E   L   S   T   I   L   G   F   441

1561  TACATATGAAATTAGACTTGTGGAAGATGGGAAATATGGAGCCCAGGATGATGCCAATGG
      ------+---------+---------+---------+---------+---------+  1620
      ATGTATACTTTAATCTGAACACCTTCTACCCTTTATACCTCGGGTCCTACTACGGTTACC

T   Y   E   I   R   L   V   E   D   G   K   Y   G   A   Q   D   D   A   N   G   461

1621  ACAATGGAATGGAATGGTTCGTGAACTAATTGATCATAAAGCTGACCTTGCAGTTGCTCC
      ------+---------+---------+---------+---------+---------+  1680
      TGTTACCTTACCTTACCAAGCACTTGATTAACTAGTATTCGACTGGAACGTCAACGAGG

Q   W   N   G   M   V   R   E   L   I   D   H   K   A   D   L   A   V   A   P   481

1681  ACTGGCTATTACCTATGTTCGAGAGAAGGTCATCGACTTTTCCAAGCCCTTTATGACACT
      ------+---------+---------+---------+---------+---------+  1740
      TGACCGATAATGGATACAAGCTCTCTTCCAGTAGCTGAAAAGGTTCGGGAAATACTGTGA

L   A   I   T   Y   V   R   E   K   V   I   D   F   S   K   P   F   M   T   L   501

1741  TGGAATAAGTATTTGTACCGCAAGCCCAATGGTACAAACCCAGGCGTCTTCTCCTTCCT
      ------+---------+---------+---------+---------+---------+  1800
      ACCTTATTCATAAACATGGCGTTCGGGTTACCATGTTTGGGTCCGCAGAAGAGGAAGGA

```
1801  GAATCCTCTCTCCCCTGATATCTGGATGTATATTCTGCTGGCTTACTTGGGTGTCAGTTG
      ----------+---------+---------+---------+---------+---------+  1860
      CTTAGGAGAGAGGGGACTATAGACCTACATATAAGACGACCGAATGAACCCACAGTCAAC

N  P  L  S  P  D  I  W  M  Y  I  L  L  A  Y  L  G  V  S  C     541

1861  TGTGCTCTTTGTCATAGCCAGGTTTAGTCCTTATGAGTGGTATAATCCACACCCTTGCAA
      ----------+---------+---------+---------+---------+---------+  1920
      ACACGAGAAACAGTATCGGTCCAAATCAGGAATACTCACCATATTAGGTGTGGGAACGTT

V  L  F  V  I  A  R  F  S  P  Y  E  W  Y  N  P  H  P  C  N     561

1921  CCCTGACTCAGACGTGGTGGAAAACAATTTACCTTGCTAAATAGTTTCTGGTTTGGAGT
      ----------+---------+---------+---------+---------+---------+  1980
      GGGACTGAGTCTGCACCACCTTTTGTTAAATGGAACGATTATCAAAGACCAAACCTCA

P  D  S  D  V  V  E  N  N  F  T  L  L  N  S  F  W  F  G  V     581

1981  TGGAGCTCTCATGCAGCAAGGTTCTGAGCTCATGCCCAAAGCACTGTCCACCAGGATAGT
      ----------+---------+---------+---------+---------+---------+  2040
      ACCTCGAGAGTACGTCGTTCCAAGACTCGAGTACGGGTTTCGTGACAGGTGGTCCTATCA

G  A  L  M  Q  Q  G  S  E  L  M  P  K  A  L  S  T  R  I  V     601

2041  GGGAGGCATTTGGTGGTTTTTCACACTTATCATCATTTCTTCGTATACTGCTAACTTAGC
      ----------+---------+---------+---------+---------+---------+  2100
      CCCTCCGTAAACCACCAAAAAGTGTGAATAGTAGTAAAGAAGCATATGACGATTGAATCG
```

FIG. 6D-2

```
        G  G  I  W  W  F  F  T  L  I  I  I  S  S  Y  T  A  N  L  A     621
      CGCCTTTCTGACAGTGGAACGGCATGGAATCCCCTATTGACTCTGCTGATGATTTAGCTAA
2101  ------+---------+---------+---------+---------+---------+     2160
      GCGGAAAGACTGTCACCTTGCCGTACCTTAGGGGATAACTGAGACGACTACTAAATCGATT

A  F  L  T  V  E  R  M  E  S  P  I  D  S  A  D  D  L  A  K     641
      ACAAACCAAGATAGAATATGGAGCAGTAGAGGATGGTGCAACCATGACTTTTTCAAGAA
2161  ------+---------+---------+---------+---------+---------+     2220
      TGTTTGGTTCTATCTTATACCTCGTCATCTCCTACCACGTTGGTACTGAAAAAGTTCTT

Q  T  K  I  E  Y  G  A  V  E  D  G  A  T  M  T  F  F  K  K     661
      ATCAAAAATCTCCACGTATGACAAAATGTGGGCCTTTATGAGTAGCAGAAGGCAGTCAGT
2221  ------+---------+---------+---------+---------+---------+     2280
      TAGTTTTTAGAGGTGCATACTGTTTTACACCCGGAAATACTCATCGTCTTCCGTCAGTCA

S  K  I  S  T  Y  D  K  M  W  A  F  M  S  S  R  R  Q  S  V     681
      GCTGGTCAAAAGTAATGAAGAAGGAATCCAGCGAGTCCTCACCTCTGATTATGCTTTCCT
2281  ------+---------+---------+---------+---------+---------+     2340
      CGACCAGTTTTCATTACTTCTTCCTTAGGTCGCTCAGGAGTGGAGACTAATACGAAAGGA

L  V  K  S  N  E  E  G  I  Q  R  V  L  T  S  D  Y  A  F  L     701
      AATGGAGTCAACAACCATCGAGTTTGTTACCCAGCGGAACTGTAACCTGACACAGATTGG
2341  ------+---------+---------+---------+---------+---------+     2400
      TTACCTCAGTTGTTGGTAGCTCAAACAATGGTCGCCTTGACATTGGACTGTGTCTAACC

```
2401 CGGCCTTATAGACTCTAAAGGTTATGGCGTTGGCACTCCCATGGGTTCTCCATATCGAGA 2460
     ----+----+----+----+----+----+----+----+----+----+----+----+
     GCCGGAATATCTGAGATTTCCAATACCGCAACCGTGAGGGTACCCAAGAGGTATAGCTCT

G   L   I   D   S   K   G   Y   G   V   G   T   P   M   G   S   P   Y   R   D   741

2461 CAAAATTACCATAGCAATTCTCTTCAGCTGCAAGAGGAAGGCAAACTGCATATGATGAAGGA 2520
     ----+----+----+----+----+----+----+----+----+----+----+----+
     GTTTTAATGGTATCGTTAAGAAGTCGACGTTCTCCTTCCGTTTGACGTATACTACTTCCT

K   I   T   I   A   I   L   Q   L   Q   E   E   G   K   L   H   M   M   K   E   761

2521 GAAATGGTGGAGGGCAATGGTGCCCAGAAGAGGAAAGCAAAGAGGCCAGTGCCCTGGG 2580
     ----+----+----+----+----+----+----+----+----+----+----+----+
     CTTTACCACCTCCCCGTTACCACGGGTCTTCTCCTTTCGTTTCTCCGGTCACGGGACCC

K   W   W   R   G   N   G   C   P   E   E   E   S   K   E   A   S   A   L   G   781

2581 GGTTCAGAATATTGGTGGCATCTTCATTGTTCTGGCAGCCGGCTTGGTGCTTTCAGTTTT 2640
     ----+----+----+----+----+----+----+----+----+----+----+----+
     CCAAGTCTTATAACCACCGTAGAAGTAACAAGACCGTCGGCCGAACCACGAAAGTCAAAA

```
2641 TGTGGCAGTGGGAGAATTTTTATACAAATCCAAAAAACGCTCAATTGGAAAGAGGTC 2700
     ---------+---------+---------+---------+---------+---------+
     ACACCGTCACCCTCTTAAAAATATGTTTAGGTTTTTTTGCGAGTTAACCTTTTCTCCAG

V  A  V  G  E  F  F  L  Y  K  S  K  K  N  A  Q  L  E  K  R  S   821

2701 CTTCTGTAGTGCCATGGTAGAAGAATTGAGGATGTCCCTGAAGTGCCAGCGGTCGGTTAAA 2760
     ---------+---------+---------+---------+---------+---------+
     GAAGACATCACGGTACCATCTTCTTAACTCCTACAGGGACTTCACGGTCGCCAGCCAATTT

F  C  S  A  M  V  E  E  L  R  M  S  L  K  C  Q  R  R  L  K   841

2761 ACATAAGCCACAGGCCCCCAGTTATTGTGAAAACAGAAGAAGTTATCAACATGCACACATT 2820
     ---------+---------+---------+---------+---------+---------+
     TGTATTCGGTGTCCGGGGTCAATAACACTTTTGTCTTCTTCAATAGTTGTACGTGTGTAA

H  K  P  Q  A  P  V  I  V  K  T  E  E  V  I  N  M  H  T  F   861

EcoRI
                                                            ----
2821 TAACGACAGAAGGTTGCCAGTAAAGAAAACCATGGCATAAAGCTGGGAGGCCGGAATTC 2878
     ---------+---------+---------+---------+---------+--------
     ATTGCTGTCTTCCAACGGTCCATTTCTTTTGGTACCGTATTTCGACCCTCCGGCCTTAAG

```
ATCTGGATGTATATTCTGCTGGCTTACTTGGGTGTCAGTTGTGTGCTCTTTGTCATAGCC  EAA4 genomic
ATCTGGATGTATATTCTGCTGGCTTACTTGGGTGTCAGTTGTGTGCTCTTTGTCATAGCC  unedited cDNA
 I  W  M  Y  I  L  L  A  Y  L  G  V  S  C  V  L  F  V  I  A
                ATT                              TGC              hemi-edited cDNA
                 I                                C
                GTT                              TAC
                 V                                Y               hemi-edited cDNA
                GTT                              TGC
                 V                                C               edited cDNA
                 ↑                                ↑

ATTTGGATGTATGTGCTCTTAGCCTGCTGGGAGTCAGCTGTTACTCTTTGTGGATTG  EAA3 genomic
                    ↑
```

FIG. 7B

```
TTTACCTTGCTAAATAGTTTCTGGTTTGGAGTTGGAGCTCTCATGCAGCAAG    EAA4 genomic
 F  T  L  L  N  S  F  W  F  G  V  G  A  L  M  Q  Q
                                            CAG          unedited cDNA
                                             Q
                                            CGG          edited cDNA
                                             R TTTACTTTACTAAATAGTTTCTGGTTTGGAGTTGGAGCTCTCATGCAGCAAG    EAA3 genomic
 F  T  L  L  N  S  F  W  F  G  V  G  A  L  M  Q  Q
                                            CAG          unedited cDNA
                                             Q
                                            CGG          edited cDNA
                                             R
```

GLUTAMATE RECEPTOR (OR EAA RECEPTOR) POLYNUCLEOTIDES AND THEIR USES

This application is a continuation-in-part of international patent application PCT/CA94/00705, which is in turn a continuation-in-part of U.S. patent application Ser. No. 08/172,188 filed Dec. 23, 1993, now abandoned.

FIELD OF THE INVENTION

This invention relates to novel CNS receptor polynucleotides and the proteins they encode, and their use in screening potential therapeutic compounds.

BACKGROUND TO THE INVENTION

In the mammalian central nervous system (CNS), the transmission of nerve impulses is controlled by the interaction between a neurotransmitter substance released by the "sending" neuron and a surface receptor on the "receiving" neuron to which the neurotransmitter binds causing excitation thereof. There are a number of neurotransmitters in the CNS, each of which target specific receiving neurons. For example, glutamate, dopamine and serotonin neurotransmitters each target a different family of receptors. Glutamate, which is referred to as an excitatory amino acid (EAA), interacts with receptors variously referred to as glutamate or EAA receptors, while dopamine and serotonin interact specifically with dopamine and serotonin receptors, respectively.

Within each receptor family, the receptors are classified by their ligand-binding or functional characteristics. For example, some EAA receptors are classified according to their differential binding to the agonists, NMDA (N-methyl-D-aspartate), AMPA (alpha-amino-3-hydroxy-5-methyl-isoxazole-4-propionate), and kainate (2-carboxy-4-(1-methylethenyl)-3-pyrrolidineacetate). Thus, NMDA receptors bind glutamate and bind NMDA-with greater affinity than kainate or AMPA, while AMPA and kainate receptors bind glutamate, and bind AMPA and kainate, respectively, with greater affinity than other agonists.

In contrast to dopamine and serotonin receptors, some EAA receptors are functional in an electrophysiological sense as determined by established electrophysiological assays such as that described by Hollman et al. in Nature 342: 643, 1989, or by any other assay appropriate for detecting conductance across a cell membrane. In essence, EAA receptors form ligand-gated ion channels. Thus, in response to binding an appropriate ligand, e.g., glutamate, AMPA, kainate or NMDA, an EAA receptor ion channel will "open" or become more permeable to allow the influx of cation that is required for normal synaptic transmission. In the absence of ligand binding, the ion channels remain "closed" or less permeable to cation, preventing the inward flow of cation required for synaptic transmission.

At least six AMPA-type rodent receptors have been cloned, and named GluR-1 to 6. Expression studies suggest that GluR-2 is the dominant subunit in determining functional properties associated with $Ca^{2+}$ permeability in this rodent receptor family. Mutation studies have shown that this permeability is determined by a single amino acid, arginine (R), in the putative channel-forming transmembrane II (TMII) of rat GluR-2; a glutamine (Q) residue is present in the other AMPA receptors. It was subsequently revealed that the R form of the GluR-2 receptor is generated from the same gene as the Q form by an RNA editing process, indicating that, in rat brain, the occurrence of this "editing" process determines cation flow in GluR-2 channels (Sommer et al, 1991, Cell, 67:11). Reports to date have found almost 100% efficiency of the editing process for rodent GluR-2 with low level expression of unaltered Q forms in the developing central nervous system (Sommer et al, supra; and see Burnashev et al, 1992, Neuron, 8:189). Most recently, the AMPA-type rat receptors GluR-5 and GluR-6 have also been shown to undergo RNA editing (Sommer et al, supra; Burnashev et al, supra; and see Kohler et al, 1993, Neuron, 10:491).

RNA editing is a relatively rare phenomenon, but occurs in various organisms and may involve a number of different mechanisms. The editing of the rodent AMPA receptor, GluR-2, has been demonstrated to require a base paired intron/exon structure.

A nuclear adenosine deaminase specific for double-stranded DNA is postulated to be involved in the base conversion, although direct evidence of the mechanism and any regulation of the process remain to be investigated.

Several human glutamate receptors have been cloned, including those of the AMPA-type such as hGluR1 (Puckett et al, 1991, Proc. Natl. Acad. Sci., 88:7557), hGluR-2, hGluR-3 (Biochem. Biophys. Acta, 1994, 1219:563) and those of the kainate-type, such as humEAA1 (EP 529,994); humEAA2 (EP 529,995); humEAA3 (EP 617,123) and humEAA4 (EP 578,409). The human glutamate receptors are of great medical importance because of their postulated role in the mediation of learning and memory acquisition. In addition, excitatory amino acids can be highly toxic to neurons and dysfunction of this neurotransmitter system has been implicated in several neurological disorders such as Alzheimer's disease, Huntington's chorea, epilepsy, Parkinson's disease, amyotrophic lateral sclerosis, AIDS encephalopathy and dementia complex. To date, the RNA editing phenomenon, an important determinate of the functional properties of CNS receptors and particularly glutamate receptors, has not been observed in humans.

SUMMARY OF THE INVENTION

It has now been discovered that the synthesis of human CNS receptors in vivo is regulated by an editing mechanism. This "editing" results in the expression from a single human CNS receptor gene of structurally distinct forms of the encoded CNS receptor protein, i.e. edited and unedited receptor forms. It is postulated that certain neurodegenerative disease states are associated with an aberrant editing mechanism. The evidence presented here further indicates that this editing mechanism is operative in a tissue-selective manner, and in a developmentally regulated manner. Thus, the expression products of a given CNS receptor-encoding gene are valuable in screening compounds for potential therapeutic utility, and particularly in selecting drug candidates that interact selectively with edited human CNS receptor forms.

Accordingly, the invention provides, in one of its aspects, a method for identifying a human CNS receptor-selective ligand, which comprises:

a) determining the interaction between a candidate ligand and a first human CNS receptor of a type that is subject to editing;

b) determining the interaction between the candidate ligand and a second human CNS receptor which receptor is an editing-altered variant of said first receptor; and either c) selecting that candidate ligand which interacts selectively with one of said receptors, or d) selecting that candidate ligand which interacts substantially equivalently with both of said receptors.

This method of the present invention is performed, in embodiments of the present invention, using first and second human glutamate receptors, and particularly using human glutamate receptors of the AMPA-type or kainate-type.

For use in the method of the present invention, the invention further provides cells that are transformed to express novel forms of edited and unedited human CNS receptors, and particularly edited and unedited forms of human glutamate receptors. For use in constructing such cells, the invention provides, in a related aspect, isolated polynucleotides that encode such receptors.

In a further aspect, the invention provides a method useful to identify agents that modulate the editing of human CNS receptors in vivo, which comprises:

a) obtaining a human neuronal cell line that (1) incorporates DNA coding for the unedited form of an edited human CNS receptor, and that (2) elaborates, upon culturing, the edited form of the receptor;

b) culturing the cell line in the presence of a candidate modulator of said editing; and c) determining the effect of said modulator on the elaboration of said edited form of said receptor.

These and other aspects of the invention are described in greater detail with reference to the accompanying drawings, in which:

BRIEF REFERENCE TO THE DRAWINGS

FIGS. 1A to 1F provide the genomic DNA and protein sequences of the unedited form of the human GluR2B receptor (SEQ ID NO:1 and 2);

Figure 2:
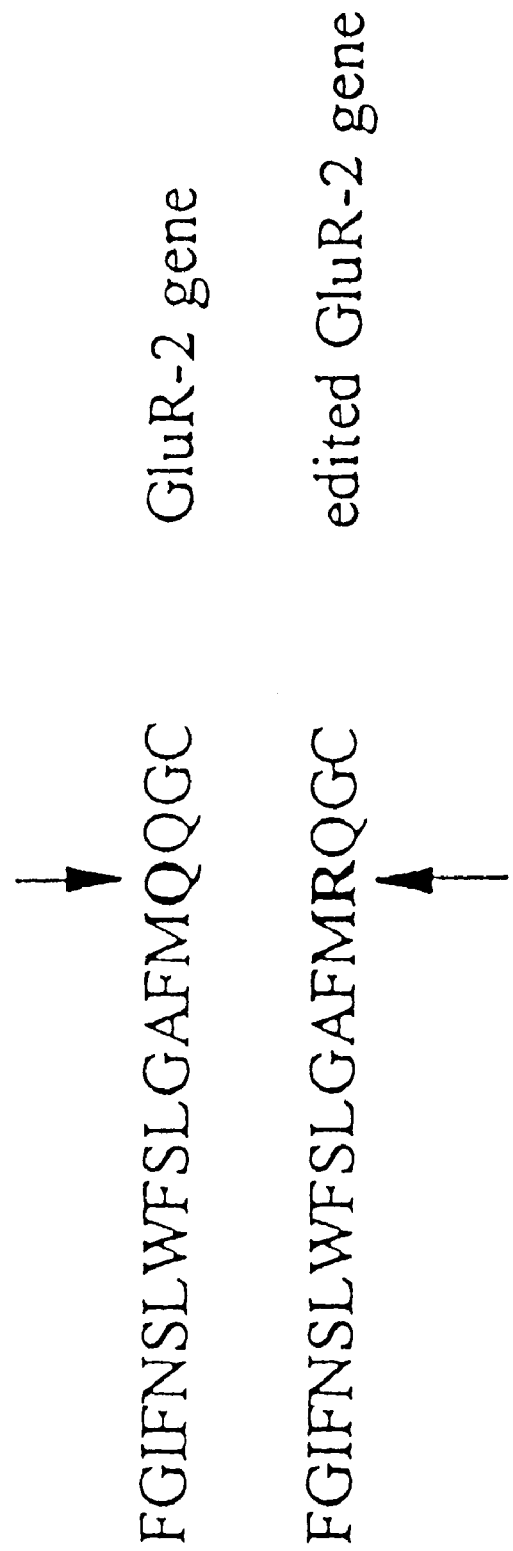
FIG. 2 is a comparison of the partial amino acid sequences of the edited and unedited forms of the GluR2B receptor.

FIGS. 5A to 5E provide the genomic DNA and protein sequences of the unedited form of the human EAA3 receptor (SEQ ID NO:3 and 4);

FIGS. 6A to 6E provide the genomic DNA and protein sequences of the unedited form of human EAA4 receptor (SEQ ID NO:5 and 6);

FIGS. 7A to 7B illustrate editing in human EAA3 and EAA4 receptors: a) comparison of genomic and cDNA nucleotide sequences and amino acid sequences in TMI; b) comparison of genomic and cDNA nucleotide sequences and amino acid sequences in TMII.

DETAILED DESCRIPTION OF THE INVENTION AND ITS PREFERRED EMBODIMENTS

The invention is based on the present discovery that a single gene coding for a human CNS receptor, when expressed in vivo, can yield not only a receptor of the amino acid sequence determined by that gene, but can also yield one or more forms of the receptor that are not encoded by that gene. This editing phenomenon was revealed by comparing the cDNA sequence of a given human receptor with the counterpart genomic DNA sequence for the given receptor. Sequence discrepancies revealed that the cDNA sequence had been altered relative to the genomic sequence, with the result that the cDNA encoded a receptor protein having at least one amino acid substitution relative to the receptor encoded by the genomic DNA. In this way, the editing phenomenon yields receptor forms that differ in terms of receptor protein structure, and in some instances also in terms of receptor protein function.

These different receptor forms are the expression products of polynucleotides characterized herein as "edited" and "unedited". "Unedited" polynucleotides are those having a genomically encoded sequence. Similarly, in "unedited" receptor proteins, each amino acid in the receptor protein sequence has an appropriate source codon within the genomic DNA sequence, i.e., the unedited polynucleotide, from which it is expressed. "Edited" receptor proteins, on the other hand, are expressed from unedited genomic polynucleotides, yet have a receptor protein sequence in which at least one amino acid is not represented in the unedited polynucleotide from which it is expressed. The terms "edited" and "unedited" are also used herein with respect to mRNA, sDNA and cDNA sequences of the respective receptor proteins.

The term "distinct", as it is used herein with respect to edited and unedited CNS receptors, refers to the differences between the edited and unedited receptors, which include at least one of a structural difference, i.e. an amino acid sequence difference, or a functional difference, i.e. a difference in ligand binding or electrophysiological properties which can be determined using assays appropriate for determining ligand/receptor interaction. The term "functionally distinct" indicates that each of the edited and unedited receptor forms reacts differently to a given stimulus. For example, functionally distinct forms of an EAA receptor may be represented by an unedited receptor form which exhibits ligand-gated ion channel activity in response to a given ligand, while the edited form of the receptor does not exhibit channel activity in the presence of that ligand. Functionally distinct forms of a CNS receptor may also have distinct ligand-binding properties.

While not being limited to any single theory with regard to the mechanism of editing, it is believed that the "editing" of a gene is catalyzed by an enzyme at the level of transcription. Thus, the "editing" enzyme, during the transcription of a genomic CNS receptor-encoding DNA, recognizes a nucleotide within the DNA sequence and, instead of incorporating the appropriate corresponding nucleotide into the mRNA, it incorporates a different nucleotide into the mRNA. The editing of CNS receptor polynucleotides does not occur 100% of the time, and thus, it appears that certain conditions or signals dictate when a CNS polynucleotide will be edited and when editing will not occur. As will be described in more detail below, the editing of human CNS genes has also been found to occur tissue specifically, occurring with greater frequency in certain CNS tissues than in others.

The term "genomic polynucleotide" is used herein to refer to a polynucleotide having a nucleotide sequence that corresponds with the coding sequence of the genomic DNA. Thus, a genomic polynucleotide according to the present invention may be genomic DNA, or synthetic or cDNA comprising the exonic coding sequences of the genomic DNA but lacking the non-coding intronic sequences. A genomic polynucleotide may also be RNA which corresponds to the genomic DNA sequence, i.e. in unedited form.

The term "isolated" is used herein with reference to intact polynucleotides to denote polynucleotides, including both DNA and RNA, which are free from polynucleotides encoding other human proteins. With reference to a human CNS receptor protein, the term "isolated" similarly refers to a receptor protein which is free from other human proteins.

Thus, in accordance with one of its aspects, the invention provides a method for identifying a ligand that interacts with the edited and/or unedited forms of a receptor, which comprises determining the interaction between the ligand candidate and a first human CNS receptor that is subject to editing, and between the ligand candidate and a second human CNS receptor that is an editing-altered variant of the first receptor, and then selecting the ligand that interacts selectively with one of said receptor forms, in the case where targetting of a drug to a particular receptor type is desired, or selecting the ligand that interacts with both receptor forms in the case where a drug that acts non-discriminately at the receptor family is desired.

For use in such a screening method, it will be necessary to identify and obtain polynucleotides that encode editing altered receptor forms within a receptor gene family. To determine if a given CNS receptor-encoding gene is subject to editing, the genomic DNA sequence of the receptor should be compared to the nucleic acid and amino acid sequences derived therefrom in vivo, specifically, the mRNA sequence transcribed in vivo from the gene sequence, or its cDNA equivalent, and the protein sequence expressed therefrom. It is important to compare the gene sequence with sequences of the mRNA and protein which are derived from in vivo processing in order to detect editing of the gene. Comparison of the gene sequence with an mRNA or protein sequence which has been artificially produced, i.e. under in vitro conditions, will likely not reflect an edited sequence since editing conditions, for example, the presence of required editing enzymes, are probably not present in vitro unless specifically added.

Whether knowledge of the editing of a known gene or a novel gene is sought, the general Procedure for obtaining the gene and its cDNA equivalent is the same. For example, procedures such as those described by Sun et al., in Proc. Natl. Acad. Sci. USA, 1992, 89:1443, can be used to isolate desired receptor-encoding cDNAs. Typically, in a first step, the desired cDNA sequence is obtained from a human brain cDNA library. For this purpose, it will be necessary to design and then prepare suitable nucleic acid probes with which to isolate cDNA encoding all or part of a CNS receptor. If a novel CNS receptor gene is being sought, the probes can be based on regions of CNS receptors which are believed to be conserved among certain CNS receptor types, for example, among CNS receptors of the kainate type. If a known gene is being sought, the probes used will desirably be complementary to a region of the gene which is unique to that gene. Alternatively, the cDNA sequence, if known, can be prepared using synthetic techniques by preparing and then ligating smaller fragments of the full-length cDNA. Isolation of cDNA which hybridizes to the probes is carried out in a manner well known to those in the art. Although it is possible, full-length receptor cDNAs are not generally isolated using the probes, but rather fragments of the full-length cDNAs are isolated. The full-length cDNAs are prepared by ligation of cDNA fragments, ligation sites being determined by overlapping regions of the cDNA fragments. On preparing a full-length cDNA, it can be sequenced using techniques well-known in the art such as the Sanger sequencing method. The mRNA sequence of the gene will of course correspond to the full-length cDNA. The sequence of the protein expressed therefrom can also be derived from the isolated cDNA sequence.

Having prepared a full-length cDNA, it can be used, in whole or in part, as a probe to isolate the desired corresponding genomic receptor-encoding DNA from a genomic DNA library. Again, this exercise will likely not render a full-length genomic DNA; however, isolated fragments of the genomic DNA can be used to prepare a full-length genomic receptor-encoding DNA. In order to facilitate isolation of a particular genomic DNA, the desired DNA can first be amplified to increase its quantity in relation to the rest of the DNA in the library. This is typically accomplished using the well-established PCR technique. In this case, PCR primers, which are short DNA fragments known to hybridize to the terminal ends of the desired genomic DNA are added to the library and under appropriate PCR conditions, the desired DNA is amplified, thereby facilitating its detection and isolation. Once isolated and/or prepared into its full-length form, the gene can be sequenced, and its sequence can then be compared to that of the isolated cDNA. Any discrepancies between the sequences indicate the occurrence of in vivo sequence editing.

It will be appreciated by those of skill in the art that it may not be necessary to sequence the entire cDNA and genomic DNA polynucleotides in order to determine, or postulate, that editing of the particular gene may have occurred. In one alternative method, only a portion of each of the cDNA and gene is sequenced in the search for sequence discrepancies, or editing. In this regard, it will be necessary to chose a region of the gene in which editing is likely to occur, for example, a region which encodes a functional domain of the receptor protein. The functional receptor domains will of course vary from receptor to receptor. In EAA receptor genes, the regions encoding intracellular transmembrane domains, which are important for ion channel activity, are regions which can be examined for evidence of editing. In the case of dopamine and serotonin receptors, which do not form ion channels, regions of the receptor genes which are believed to encode a ligand binding domain should can be examined for sequence discrepancies. If no editing is found in selected regions of the genomic and cDNA polynucleotides, it will then, of course, be necessary to compare the entire sequences of each in order to conclude that the particular gene is either edited or not.

Another method of identifying if editing has, or may have, occurred is to compare the properties of the receptor proteins expressed from each of the isolated CNS receptor cDNA and gene. For this purpose, the cDNA and genomic DNA are cloned into expression vectors which are used to transform suitable cells, as described in detail below, and the receptor proteins or membrane preparations produced therefrom, are isolated for comparison using the ligand-binding and/or electrophysiological assays also described in detail below. Functional differences between the proteins is also an indicator that editing of that particular CNS receptor protein occurs at some stage prior to its expression.

On postulating that editing of a CNS receptor gene occurs, it will then be necessary to exclude the possibility that multiple genes or alternate exons are responsible for sequence differences between the genomic DNA and protein product, i.e. to confirm that such sequence differences evidence the occurrence of editing. At the outset, genomic DNA encoding the protein must be isolated, using specific DNA probes as described above, from genomic DNA libraries of different regions of the brain. This will ensure that if multiple genes exist, one or more of which are region-specific, their existence will not be overlooked. Further, the method of primer-based PCR amplification can be applied to amplify DNA that may be present in the DNA libraries in only very minute quantities.

On isolation of genomic DNA, one way to confirm that multiple genes, i.e. a gene coding for the unedited form of the protein and a gene coding for the edited form of the protein, do not exist, or that alternatively spliced exons do not account for the different protein forms, is to identify characteristics that would exist in one form of the gene (or coding exon) but would be lacking in the other form of the gene (or coding exon), for example, restriction enzyme sites. Thus, exposing isolates of the genomic DNA to restriction enzymes for which a recognition site is present in the region of concern will yield two fragments on analysis using probe-specific hybridization. On the other hand, exposing genomic DNA isolates to restriction enzymes for which there is no recognition site in the region of concern will yield a single fragment only on analysis using probe-specific hybridization. Inconsistencies from the expected results indicates that a multiple gene or exon may be involved, and the genomic DNA yielding the unexpected results must be fully sequenced in order to identify the reason for the inconsistency.

Information about the characteristics of both the edited and unedited forms of a receptor protein would, of course, only be available if the protein sequences of each of the protein forms were known. In most cases, however, the only information that will be available is a receptor gene sequence and a protein sequence that may or may not correspond to the known gene sequence. Thus, different methods must be used to determine if RNA editing of the gene occurs, or if multiple genes or exons are involved to result in a protein that does not correspond in sequence to the gene believed to encode it. One such method is based on the fact that intronic gene sequences vary from gene to gene despite the fact that the coding (exonic) sequences of two genes may vary only slightly, for example by a single codon. In this method, isolated genomic DNA is subjected to restriction enzyme digestion and is then immobilized on a nitrocellulose filter. A labelled DNA probe directed to the target region, i.e. the region of the gene:protein discrepancy, is used to identify the enzyme-digested DNA fragments. Because the sequence of the genomic DNA is known, the existence of restriction sites in the targeted region and thus, the number of restriction fragments expected from a given enzyme digestion, will be known, and the result of more or less fragments than expected will indicate the existence of multiple genes or alternate codons.

Alternatively, isolated genomic DNA which has been PCR-amplified can be fully sequenced in the search for multiple genes or alternate exons. This method is preferably used to confirm results obtained in other methods, such as those described above, or when such methods do not yield confirmative results. Full sequencing of any isolated genes or gene fragments will confirm their identity. If a gene encoding the "edited" protein is not found on sequencing a substantial number of positive clones from each region of the brain, i.e. 50–100, then the existence of multiple genes and the existence of alternate exons can be excluded as possibilities for the protein sequence discrepancy.

Further, in order to exclude the possibility that the difference between the DNA and protein sequences is not the result of random mutation, i.e. a point mutation or other form of mutation, it is important to determine that it occurs with a frequency greater than that which would be associated with random mutation. In this regard, expression of the edited and unedited forms of the protein with a frequency of greater than 1 in 1000, or 1 in 10,000, would eliminate the concern that either protein was the result of mutation, particularly since mutations in the human CNS are extremely rare.

In a specific embodiment of the present invention, a human EAA receptor, namely the GluR2B receptor, which is described in co-pending U.S. application Ser. No. 07/896, 437 now abandoned, was determined to be subject to editing as described in detail in the specific examples. Briefly, genomic DNA fragments of the GluR2B receptor, and full-length cDNA derived from the amino acid sequence of the receptor protein, were used to probe a genomic DNA library. Full-length genomic DNA, isolated using these probes, was sequenced and its sequence was then compared to the full-length GluR2B cDNA (SEQ ID NO:8) and protein sequences. A comparison of the sequences identified a single codon difference in the coding region of the transmembrane II domain. Specifically, the genomic DNA was found to encode a glutamine at position 587 of the protein sequence, while the cDNA encoded an arginine at position 587. The genomic DNA sequence coding for the GluR2B receptor (SEQ ID NO:1 and 2) is illustrated in FIGS. 1A to 1F, and is different from the cDNA sequence illustrated in U.S. Ser. No. 07/896,437, now abandoned, by the single nucleotide change of G to A at position 2134. The change is also reflected in the protein sequence of the GluR2B receptor at position 587. The change in protein sequence is illustrated in FIG. 2 for greater clarity. Thus, according to one embodiment of the invention, there is provided a polynucleotide that codes for the Q-587 form of the human GluR2 receptor, particularly of the human GluR2B receptor. There is further provided a transformed cell having incorporated expressibly therein a polynucleotide encoding the Q-587 form of the human GluR2 receptor. Also provided is the Q-587 form of the human GluR2 receptor (SEQ ID NO:2), per se.

To confirm that multiple GluR2 receptor-encoding genes do not exist, i.e. one gene encoding the unedited Q-587 form of GluR2B (SEQ ID NO:2) and another gene encoding the R-587 form of GluR2B (SEQ ID NO:8), or that multiple exons coding for these edited and unedited forms do not exist, genomic GluR2B DNA (SEQ ID NO:1) was subjected to restriction enzyme digestion. Specifically, a genomic DNA sample was digested with a restriction enzyme (BglII) known to have a recognition site in the exon containing the codon that is subject to "editing", while other genomic DNA samples were digested with restriction enzymes (EcoRI, HindIII and PstI) which did not have recognition sites in the edited exon. Following enzyme digestion, the DNA and its fragments were resolved using gel electrophoresis, and the fragments containing the "edited" exon were identified using a labelled probe specific for the exon. As was expected, two DNA fragments resulted from the BglII digestion. The appearance of three or more bands following a BglII enzyme digestion would have indicated either the presence of two genes in which the intronic sequences differed, or two exons both including the BglII restriction site but having different sequences. A single band resulted in each of the EcoRI, HindIII and PstI DNA digestions. Again, the appearance of more than one band in these cases would have indicated either the presence of two genes or exons as described above.

Finally, to confirm that the sequence difference between the genomic GluR2B DNA (SEQ ID NO:1) and the GluR2B receptor (SEQ ID NO:8) was not the result of random mutation, several GluR2B genomic and cDNA clones were sequenced to determine the frequency of the sequence change. For this purpose, various types of brain tissue were probed, as described above. The results clearly indicated that mutation was not the cause of the sequence changes that occurred between GluR2B DNA and the expressed GluR2B protein (SEQ ID NO:8). The "editing" of GluR2B occurred with different frequencies in different tissues, for example GluR2B of the hippocampus, cerebellum and temporal cortex was 100t edited (i.e. contained the arginine at position 587), while GluR2B of the substantia nigra was 71% edited, GluR2B of the corpus striatum was 89% edited and GluR2B of fetal brain tissue was 96% edited.

In other embodiments of the present invention, human EAA3 and EAA4 receptors of the kainate family, described in EP 617,123 and EP 578,409 respectively, incorporated herein by reference, have been determined to be subject to editing. Using similar techniques that were used to determine editing in the GluR2B receptor, human EAA3 (SEQ ID NO:3) and EAA4 (SEQ ID NO:5) genomic DNA were observed to encode receptors having different amino acid sequences than their corresponding cDNA. Specifically, EAA3 genomic DNA (SEQ ID NO:3) encodes a glutamine (Q) residue at position 591 of the mature receptor protein while cDNA derived from various regions of the brain has been observed to encode arginine (R) at position 591. On the other hand, EAA4 genomic DNA (SEQ ID NO:5) was found to be edited at three sites; isoleucine at position 532 of the mature protein replaced with valine, tyrosine at position 536 replaced with cysteine and glutamine at position 586 replaced with arginine. The genomic sequences of EAA3 (SEQ ID NO:3) and EAA4 (SEQ ID NO:5) are illustrated in FIGS. 5A to 5E and FIGS. 6A to 6E respectively. The changes in protein sequence at each of these sites are the result of a single nucleotide substitution, adenosine→guanosine (A→G) as illustrated in FIGS. 7A and 7B.

Thus, in embodiments of the invention, there are provided the following human CNS receptor proteins, as well as polynucleotides encoding them, and transformed cells that expressibly incorporate such polynucleotides: (1) the R-591 (SEQ ID NO:10) and Q-591 (SEQ ID NO:4) forms of the human EAA3 receptor; (2) a form of the human EAA4 receptor protein having a novel combination of one or more of the following amino acid identifiers: Ile-532, Val-532, Tyr-536, Cys-536, Gln-586 and Arg-586 (SEQ ID NO:14).

The glutamine to arginine (Q/R) replacement in both EAA3 and EAA4 occur in the transmembrane II (TMII) region of the receptor protein. The additional I/V$^{532}$ and Y/C$^{536}$ editing sites in EAA4 occur in the TMI region adding further complexity by enabling up to eight isoforms of EAA4 to be generated. Hence RNA editing of EAA4 results in a mosaic of receptors which may regulate glutamate activated Ca$^{2+}$ influx in the brain. The frequency of edited codons was examined in tissue from various regions of the brain and found to be differentially represented. Of the eight possible isoforms, five were observed in the various regions; specifically I.C.R, V.C.R, I.Y.Q, V.C.Q, and I.Y.R. As was the case for human GluR2, the relative frequency of the edited/unedited codons observed was also differentially regulated in an age specific manner. EAA4 cDNA clones isolated from human fetal brain (17–18 weeks gestation) revealed a relatively low editing efficiency. The majority of EAA4 cDNAs amplified from the cerebellum of a 2 year old female were of the hemi-edited I.C.R type. This variant was also the predominant type found in corpus striatum cDNAs. While not being bound by theory it is believed that in individuals of the same age, different editing states can exist in distinct neuronal populations. Thus the I.C.R form could have a role in the kainate receptor channel complexes in a specific neuronal tissue such as the cerebellum or corpus striatum while being rare in the brain as a whole. Hippocampus derived cDNAs revealed a distinctly different expression pattern of edited EAA4 with the majority of cDNAs examined being fully edited V.C.R. Editing in substantia nigra resulted in an approximately equal ratio of unedited I.Y.Q to fully edited V.C.R cDNA while no editing was observed in temporal cortex.

Examination of Q/R editing frequency in EAA3 has also revealed a non-uniform distribution in human brain. Again fetal tissue harbours a higher ratio of unedited Q forms than is generally observed in adult brain. The cerebellar and temporal cortical tissues used in this study were isolated from the same 2 year old female and indicate a significant (p<0.05) reduction of EAA3 editing in the cerebellum. Hippocampal tissue isolated from another individual of the same age (female, 2 years) indicates editing at a similar level to that of temporal cortex but again different to that of the cerebellum (p<0.05). Editing efficiencies were also found to be high for substantia nigra (60 years) and corpus striatum (57 and 63 years).

Having identified and confirmed a CNS receptor gene that is subject to editing, it is desirable to construct by application of genetic engineering techniques cells that produce forms of the receptor that are to be targetted in drug screening, e.g., one or more of the edited forms and/or the unedited form. According to one embodiment of the invention, the construction of such engineered cells, including both prokaryotic and eukaryotic cells, is achieved by introducing into a host cell a recombinant DNA construct in which DNA coding for a secretable form of the receptors, i.e. a form bearing its native signal peptide or a functional, heterologous equivalent thereof, is linked operably with expression controlling elements that are functional in the selected host to drive expression of the receptor-encoding DNA, and thus elaborate the desired receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The "unedited" receptor-encoding DNA can either be genomic in nature or, alternatively, can be derived from the protein sequence, i.e. cDNA. On the other hand, the "edited" receptor-encoding DNA can only be used in a cDNA form, as it does not exist in genomic form.

The particular cell type selected to serve as host for production of a human receptor can be any of several cell types currently available in the art. It is, however, important that the cell type selected for production of receptor to be used in ligand screening assays will not cause editing of the receptor-encoding DNA to be expressed. According to one embodiment of the present invention, the cell line selected to serve as host for the production of a CNS receptor is a mammalian cell other than a human neuronal cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2).

A variety of gene expression systems have been adapted for use with these hosts and are now commercially available. Any one of these systems can be selected to drive expression of the human CNS receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the receptor in secretable form is linked with expression controlling DNA sequences recognized by the host, and which include a region 5' of the receptor-encoding DNA to drive expression, and a 3' region to terminate expression. The plasmidic vector harbouring the recombinant DNA expression construct typically incorporates such other functional components as an origin of replication, usually virally-derived, to permit replication of the plasmid in the expression host and desirably also for plasmid amplification in a bacterial host, such as E.coli. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metallothionein gene promoter, and other steroid-inducible promoters.

The receptor-encoding DNA is incorporated for expression into any suitable expression vector, and host cells are transfected therewith using conventional procedures, such as DNA-mediated transformation, electroporation, or particle gun transformation. In this regard, it will be appreciated that the receptor-encoding DNA may be replaced with a synonymous codon equivalent of the isolated genomic sequence. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the E. coli gpt gene which confers resistance to mycophenolic acid, the neo gene from transposon Tn5 which confers resistance to the antibiotic G418 and to neomycin, the dhfr sequence from murine cells or E. coli which changes the phenotype of DHFR− cells into DHFR+ cells, and the tk gene of herpes simplex virus, which makes TK− cells phenotypically TK+ cells. Both transient expression and stable expression can provide transformed cell lines, and membrane preparations derived therefrom, for use in ligand screening assays.

For use in ligand screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e. ligand binding experiments, frozen intact cells are homogenized while in cold water suspension and a membrane pellet is collected after centrifugation. The pellet is then washed in cold water, and dialyzed to remove endogenous ligands, such as glutamate in the case of EAA receptors, that would otherwise compete for binding in the assays. The dialyzed membranes may then be used as such, or after storage in lyophilized form, in the ligand binding assays. Alternatively, intact, fresh cells harvested about two days after transient transfection, or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding interaction between a ligand candidate and a human CNS receptor is evaluated typically using a predetermined amount of cell-derived membrane (measured for example by protein determination), generally from about 25 µg to 100 µg. Generally, competitive binding assays will be useful to evaluate the affinity of a ligand candidate relative to an endogenous ligand, such as glutamate, serotonin or dopamine, depending on the type of receptor involved. This competitive binding assay can be performed by incubating the membrane preparation with radiolabelled endogenous ligand in the presence of unlabelled ligand candidate added at varying concentrations. Following incubation, either displaced or bound radiolabelled ligand can be recovered and measured, to determine the relative binding affinities of the ligand candidate and endogenous ligand for the particular receptor used as substrate. In this way, the affinities of various ligand candidates for the human CNS receptors of the present invention can be measured.

As an alternative to using cells that express receptor-encoding DNA, ligand/receptor interaaction may also be determined electrophysiologically, e.g., using cells for example Xenopus oocytes, that yield functional membrane-bound receptor following introduction by injection either of receptor-encoding messenger RNA into the oocyte cytoplasm, or of receptor-encoding DNA into the oocyte nucleus. To generate the messenger RNA of cytoplasmic delivery, the receptor-encoding DNA is typically subcloned first into a plasmidic vector adjacent a suitable promoter region, such as the T3 or T7 bacteriophage promoters, to enable transcription into RNA message. RNA is then transcribed from the inserted gene in vitro, collected and then injected into Xenopus oocytes. Following the injection of nL volumes of an RNA solution, the oocytes are left to incubate for up to several days, and are then tested for the ability to respond to a ligand candidate supplied in a bathing solution. In the case of EAA receptors, which act in part by operating a membrane channel through which cations may selectively pass, the functioning of the receptor in response to a particular ligand candidate in the bathing solution may typically be measured as an electrical current utilizing microelectrodes inserted into the cell, in the established manner.

Having expressed the edited and unedited forms of a receptor, it is desirable to distinguish the edited form of the receptor from its unedited counterpart. It is contemplated that certain neurodegenerative disease states may be associated with a dysfunctional editing mechanism. The functional differences between the edited and unedited forms of a receptor, thus, are valuable in screening compounds for potential therapeutic utility, e.g. to prevent over-activity of a particular function, such as channel activity, or to enhance a retarded receptor function. In this regard, a compound which is selective for either the edited or unedited form of the receptor is desirable.

The edited and unedited receptor forms may be differentiated in terms of ligand binding characteristics, as described above, i.e. a ligand that binds to one form may be found to have little or no affinity for the other form. Thus, one method for determining selectivity of the edited and unedited forms of the receptor involves conducting comparative binding assays. Specifically, a cell encoding the edited form of the receptor is incubated with a test compound under appropriate conditions in the presence of an endogenous ligand, and the ligand binding affinity of that compound for that form of the receptor is determined relative to the endogenous ligand. This affinity is compared to the ligand binding affinity of the compound for the unedited form of the receptor determined in the same manner. Of course, the effects on receptor function of differential ligand binding characteristics should be considered in the instance that a compound exhibits a strong affinity for one receptor form while exhibiting a relatively weak affinity for the other receptor form.

Alternatively, the edited and unedited forms of a receptor may be distinguished on the basis of electrophysiological function, particularly where EAA receptors are concerned. Electrophysiological function is determined by measuring the ligand-induced electrical current across a receptor-encoding cell, or a membrane preparation thereof, using a channel activity assay such as that described by Verdoorn et al. in Mol. Pharmacol., 1988, 34:298. Briefly, the cell or membrane preparation is incubated in the presence of an endogenous ligand, for example glutamate, and the resulting electrical current is measured. It will be appreciated that the ligand preferentially bound by the receptor is the most suitable ligand with which to conduct these functional studies, e.g. kainate is the most suitable ligand for receptors that preferentially bind kainate, while AMPA is the most suitable ligand for receptors that preferentially bind AMPA. Differences in the electrophysiological function of the edited and unedited forms of the receptor can then be determined. As noted above, the effect of differentially binding test compounds on electrophysiological function can also be determined.

With reference to the GluR2B receptor embodiment of the present invention, the functional differences between the unedited and edited forms of the receptor can be determined as described above. The ligand used to induce current flow in the GluR2B receptor is preferably AMPA. In the presence of AMPA, the unedited form of the receptor elicits an electrical current as it forms a ligand-gated ion channel which is permeable to divalent cations, and notably, permeable to calcium, while the edited form of the receptor does not elicit a current as it does form an ion channel which is permeable to divalent cations.

In another embodiment of the present invention, DNA oligonucleotide probes are provided which facilitate the identification of genomic DNA encoding the unedited form of a protein, and to distinguish the cDNA version of edited mRNA from the cDNA version of unedited mRNA. The probes, comprising at least about 17 nucleotides, will correspond to the unedited region in the "unedited" genomic DNA, or to the edited region in the cDNA version of the "edited" mRNA sequence. As will be appreciated, a number of methods for using probes according to the present invention exist to successfully identify the target DNA sequence. In one method, for example, the probe is used as a hybridization probe in the usual manner. Thus, isolated immobilized DNA is combined with the probe under hybridization conditions, and the probe hybridizes to DNA having a corresponding sequence. Generally, in order to identify DNA/probe hybridization, the probe is labelled, e.g. by conjugation to a reporter molecule, such as a radiolabel, an enzyme label, a luminescent label or the like, using linker technology established for this purpose, or the probe incorporates in its structure a label such as a radioisotope of a molecule, e.g. $^3$H and $^{13}$C. To distinguish between the edited and unedited cDNA forms, high stringency conditions, and usually probes that are sequence complements of the target region, must be used due to the highly homologous nature of the two receptor forms.

Another method for using probes according to the present invention is in the well-known PCR amplification procedure. In this method, a probe is prepared which incorporates the "unedited" codon at its 3' terminal end. The probe is incubated under PCR conditions with a genomic nucleic acid mixture, and if a sequence complementary to the probe is present, that sequence will be amplified. If, however, only a sequence encoding the "edited" version is present, the mismatched codon sequences will prevent PCR amplification from occurring.

In another of its aspects, the invention provides an in vitro method for identifying agents that modulate the editing of human CNS receptors in vivo, which comprises:

a) obtaining a human neuronal cell line that (1) incorporates DNA coding for the unedited form of an edited human CNS receptor, and (2) elaborates, upon culturing, the edited form of the receptor;

b) culturing the cell line in the presence of a candidate modulator of said editing; and c) determining the effect of said modulator on the elaboration of said edited form of said receptor.

Particularly suitable as host cells for the construction of such cell lines are the human neuronal cell lines designated IMR-32 (ATCC CCL 127), SK-N-MC (ATCC HTB 10) and SK-N-SH (ATCC HTB 11). In one embodiment of the invention, the selected host is transformed to incorporate expressibly therein a polynucleotide that encodes the unedited form of the human GluR2B receptor (SEQ ID NO:2), or the unedited form of the human EAA3 (SEQ ID NO:4) or human EAA4 (SEQ ID NO:6) receptor. Confirmation that the transformants express the edited form of the encoded receptor upon culturing can be obtained by constructing a cDNA library from message recovered from cells cultured under the conditions to be used during the assay, with editing being revealed by appropriate sequence alteration in cDNA encoding the chosen receptor target. With editing activity confirmed in the constructed host, the assay can then proceed simply by incubating the host in the presence of a chosen modulator of editing activity, and then again constructing a cDNA library from the RNA transcripts elaborated during culturing. Changes in the cDNA sequence at the predicted editing site reveal, correspondingly, an effect of the chosen modulator on the CNS receptor editing process.

Specific embodiments of the present invention are described in the following specific examples which are not to be construed as limiting.

EXAMPLE 1

Isolation of Genomic and cDNA Encoding GluR2B

The following PCR primers were used to amplify both genomic and cDNA sequences of GluR2B:

PCR-1: 5'AACCTTGGCGAAATATCGCATCC3' (SEQ ID NO:15)

PCR-2: 5'GAGCCTCGGGATATCTATCATG3' (SEQ ID NO:16)

PCR-3: 5'ACACACCTCCAACAATGCGCCC3' (SEQ ID NO:17)

Figure 3:
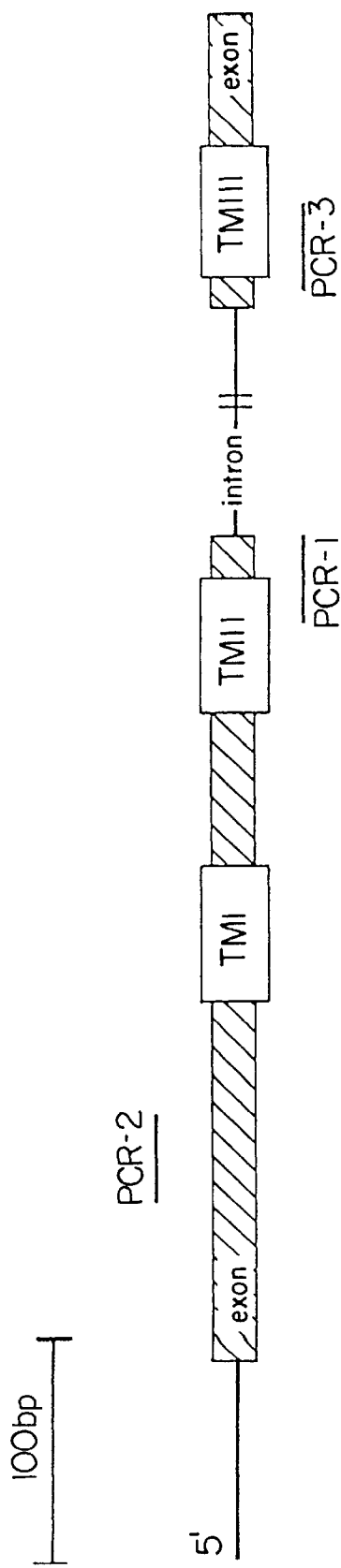
FIG. 3 illustrates the exon of the GluR2B gene which is subject to editing, and the primers used in genomic DNA isolation.

These primers were derived from coding regions of the cDNA sequence of GluR2B and are depicted in FIG. 3. The PCR-1 and PCR-2 primers, which encode respectively a region of the DNA 5' to transmembrane domain I (TMI) and a region 3' of transmembrane domain II (TMII), both of which are in a single exon, were used to amplify GluR2B genomic DNA (obtained from Clontech). The PCR-2 primer combined with the PCR-3 primer, which encodes a region in an adjacent codon, were used to amplify GluR2B cDNA (human ZAP cDNA libraries obtained from Stratagene). The fact that the PCR-3 primer corresponded to a region in a neighbouring exon ensured that only cDNA's were being examined and not contaminating fragments of genomic DNA (which would be much larger in size due to the presence of intron DNA between the two exons).

The DNA amplification reaction mixtures of both genomic and cDNAs contained: 100–500 ng DNA, 30 pmol of each primer, 5 units Taq polymerase (obtained from Promega), 0.2 mM of each dNTP (in 10 mM KCl, 10 mM ammonium sulphate, 20 mM Tris-HCl, pH 8.8, 2 mM magnesium sulphate, 0.1% Triton). The conditions for the first 35 amplification cycles were as follows: 94° C. for 30 seconds, 55–61° C. for 45 seconds and 72° C. for 2 minutes. This was followed by a 10 minute incubation at 72° C.

The amplified DNA was separated using gel electrophoresis, and the desired DNA fragments, i.e. a 294 bp fragment from the genomic DNA and a 326 bp fragment from the cDNA, were purified from the gel and subcloned into plasmid pT7blue (obtained from Novagen) for screening and sequencing.

A comparison of the genomic and cDNA sequences identified a single nucleotide difference in the coding region of the transmembrane II domain at position 2134. Specifically, the genomic DNA included a G thereby encoding a glutamine, while the cDNA included an A thereby encoding an arginine.

EXAMPLE 2

Frequency of RNA Editing of GluR2B

The frequency of editing was determined using the plasmid DNA isolated according to Example 1. At the outset, the presence of the GluR2 insert (either genomic or cDNA) was confirmed by digestion with BglII. Linearization of the plasmid DNA indicates the presence of the GluR2 insert. The linearized plasmids were then tested for the presence or absence of editing. This was determined by BbvI digestion, the recognition sequence for which is present in the unedited sequence. Thus, digestion of the unedited DNA with BbvI yields two fragments, while digestion of the edited DNA with BbvI yields a single fragment. The frequencies of edited vs. unedited GluR2B were as follows:

EXAMPLE 3

Confirmation of RNA Editing of GluR2B Gene

Initially, a Southern blot analysis was conducted in order to determine if two distinct GluR2B genes existed. Aliquots of human genomic DNA (8 µg) were individually digested with EcoRI, HindIII, PstI and BglII restriction enzymes (obtained from New England Biolabs). The digested DNA was then run on a 0.7% agarose gel, transferred to a nylon membrane and UV crosslinked. The immobilized DNA was hybridized to a purified TMI/TMII exon probe (i.e. the PCR-1/PCR-2 amplification product from Example 1) and radiolabelled with [$\alpha^{32}$P]dCTP using the random priming method (Amersham). Hybridization was carried out in 6× SSC (saline sodium citrate), 509% formamide, 5× Denhardt's solution, 0.5% SDS and 100 µg/ml sonicated salmon sperm DNA, at 42° C. for 16 hours. The filters were washed with increasing stringencies up to 0.5× SSC/0.5% SDS, at 60° C. for 20 minutes, before exposure to x-ray film at −80° C. for 48 hours. The EcoRI, HindIII and PstI digests produced single bands upon hybridization with the TMI/TMII probe. This result was indicative of the existence of a single GluR2B gene which was known not to possess recognition sites in the TMI/TMII region for the EcoRI, HindIII and PstI enzymes.

Figure 4:
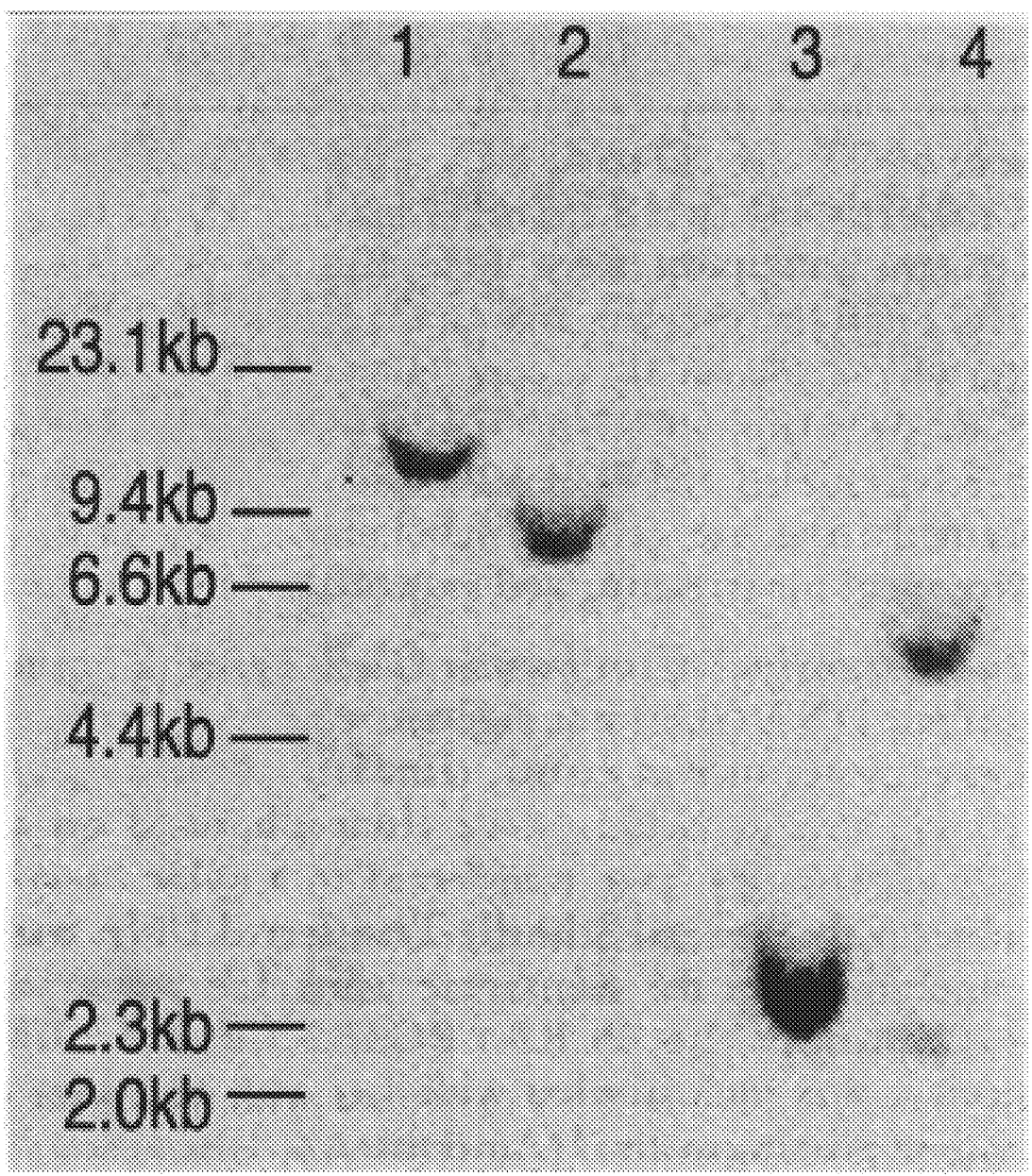
FIG. 4 illustrates the results of an enzymatic digestion of human genomic GluR2B DNA.

It was then necessary to determine if multiple exons were involved in the expression of the two forms of the GluR2B receptor. This was accomplished by digesting the genomic DNA with the BglII restriction enzyme. The TMI/TMII exon includes a BglII recognition site. Thus, a single exon would yield 2 bands, whereas multiple related exons would yield 3 or more bands. Only 2 bands of 5.5 kb and 2.2 kb were observed, confirming that the different forms of GluR2B are not as a result of multiple exons. The results of the analysis are illustrated in FIG. 4.

EXAMPLE 4

Expression of Unedited GluR2B Receptor

For transient expression in mammalian cells, genomic and cDNA coding for the human GluR2B receptor is incorporated into the mammalian expression vector pcDNA1, which is available commercially from Invitrogen Corporation (San Diego, Calif., USA; catalogue number V490-20). This is a multifunctional 4.2 kb plasmid vector designed for DNA expression in eukaryotic systems. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

| | Human GluR-2 | | | Human GluR-4 | | |
|---|---|---|---|---|---|---|
| TISSUE | Q (CAG) | R (CGG) | % EDITED | Q (CAG) | R (CGG) | % EDITED |
| GENOMIC DNA | 30 | 0 | 0 | 36 | 0 | 0 |
| CEREBELLUM | 0 | 37 | 100 | 35 | 0 | 0 |
| FETAL BRAIN | 2 | 51 | 96 | 33 | 0 | 0 |
| HIPPOCAMPUS | 0 | 43 | 100 | 38 | 0 | 0 |
| SUBSTANTIA NIGRA | 15 | 36 | 71 | 36 | 0 | 0 |
| TEMPORAL CORTEX | 0 | 43 | 100 | 28 | 0 | 0 |

To facilitate incorporation of GluR2B receptor-encoding cDNA into an expression vector, a NotI site is introduced onto the 5' flank of the Bluescript-SK cDNA insert, and the DNA insert is then released as a 3.4 kb HindIII/NotI fragment, which is then incorporated at the HindIII/NotI sites in the pcDNAI polylinker. Sequencing across the junctions is performed to confirm proper insert orientation in pcDNA1. The resulting plasmid is then introduced for transient expression into a selected mammalian cell host, in this case cells of the COS-1 lineage (available from the American Type Culture Collection, Rockville, Md. under ATCC CRL 1650). The cells are transfected with approximately 8 ug DNA per $10^6$ COS cells by DEAE-mediated DNA transfection and treated with chloroquine according to the procedures described by Maniatis et al, supra. Briefly, COS-1 cells are plated at a density of $5 \times 10^6$ cells/dish and then grown for 24 hours in FBS-supplemented DMEM/F12 medium. Medium is then removed and the cells are washed in PBS and then in medium. There is then applied on the cells 10 ml of a transfection solution containing DEAE dextran (0.4 mg/ml), 100 uM chloroquine, 10% NuSerum, DNA (0.4 mg/ml) in DMEM/F12 medium. After incubation for 3 hours at 37° C., cells are washed in PBS and medium as just described and are then shocked for 1 minute with 10% DMSO in DMEM/F12 medium. Cells are grown for 2–3 days in 10% FBS-supplemented medium, and at the end of the incubation, the dishes are placed on ice, washed with ice cold PBS and then removed by scraping. Cells are harvested by centrifugation at 1000 rpm for 10 minutes and the cellular pellet is frozen in liquid nitrogen, for subsequent use in ligand binding assays.

In a like manner, stably transfected cell lines can also prepared using two different cell types as host: CHO K1 and CHO Pro5. To construct these cell lines, the DNA is incorporated into the mammalian expression vector pRC/CMV (Invitrogen), which enables stable expression. The cDNA is inserted such that it is under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Maniatis et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and the cells are shocked with medium containing 15% glycerol. Three minutes later, the cells are washed with medium and incubated for 24 hours under normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 5

Ligand Binding Assay

Transfected cells in the frozen state are resuspended in ice-cold distilled water using a hand homogenizer, sonicated for 5 seconds, and then centrifuged for 20 minutes at 50,000 g. The supernatant is discarded and the membrane pellet stored frozen at −70° C.

COS cell membrane pellets are suspended in ice cold 50 mM Tris-HCl (pH 7.55, 5° C.) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation is used as a tissue source for the binding experiments described below.

Binding assays are performed using an amount of COS-derived membrane equivalent to from 25–100 µg as judged by protein determination and a selected radiolabelled ligand. In particular, for AMPA-binding assays, incubation mixtures consisted of 25–100 µg tissue protein and D,L-alpha-[5-methyl-$^3$H]amino-3-hydroxy-5-methylisoxazole-4-propionic acid ($^3$H-AMPA, 27.6 Ci/mmole, 10 nM final) with 0.1M KSCN and 2.5 mM $CaCl_2$ in the 1 ml final volume. Non-specific binding is determined in the presence of 1 mM L-glutamate. Samples are incubated on ice for 60 minutes in plastic minivials, and bound and free ligand are separated by centrifugation for 30 minutes at 50,000 g. Pellets are washed twice in 4 ml of the cold incubation buffer, then 5 ml of Beckman Ready-Protein Plus scintillation cocktail is added for counting.

EXAMPLE 6

Isolation of Genomic and cDNA Encoding GluR4

The procedure similar to that outlined in Example 1 was carried for another human CNS receptor, namely the GluR4 receptor, which is described in co-pending U.S. application Ser. No. 07/924,553. PCR primers for the same regions as those used for GluR2B were prepared and used to amplify GluR4 genomic DNA (obtained from Clontech) and cDNA (in human ZAP cDNA libraries obtained from Stratagene).

The isolated GluR4 genomic DNA and cDNA were compared for sequence discrepancies and none were found indicating that editing does not occur in the GluR4 human CNS receptor.

EXAMPLE 7

Isolation of Genomic and cDNA Encoding EAA3 and EAA4

The following PCR primers were used to amplify both genomic and cDNA sequences of EAA3:
PCR5-2  5'-CTTGCAATCACAAAGAGTACACAG-3' (SEQ ID NO:18)
PCR5-3  5'-CTGGTCGATAGAGCTTTGGG-3' (SEQ ID NO:19)
PCR5-26  5'-CTCCAAACCCTTCATGACCC-3' (SEQ ID NO:20)
5int-1  5'-GGGAAAATAGCAGGCTGGAATCGTATACCTTG-3' (SEQ ID NO:21)
5int-3  5'-CCCTACGAGTGGTATAACCCC-3' (SEQ ID NO:22)
PCR6-1  5'-GCTGACCTTGCAGTTGCTCC-3' (SEQ ID NO:23)
PCR6-2  5'-CCTGGCTATGACAAAGAGCAC-3' (SEQ ID NO:24)
PCR6-3  5'-CTGGTGGACAGTGCTTTGGG-3' (SEQ ID NO:25)
6int-1  5'-GGCAAAATGGGCAACCGGTGTACCTTG-3' (SEQ ID NO:26)

6int-3 5'-CCACACCCTTGCAACCCTGA-3' (SEQ ID NO:27)

Amplification—Using the mouse genomic structure and the human cDNA sequences, the above primers were designed to amplify both genomic and cDNA sequences of EAA3 and EAA4. The combinations PCR5-3/PCR5-26 and PCR6-1/PCR6-3 were used to amplify EAA3, EAA4, and EAA5 cDNAs respectively. These primers originate from separate exons thus ensuring only cDNAs were being examined and not potential genomic DNA contamination in the cDNA libraries. Genomic DNAs were examined by using the primer combinations 5-2/5-26 and 5int-3/5int-1 (EAA3); and PCR6-1/PCR6-2 and 6int-3/6int-1(EAA4). Human cDNAs were isolated from the bacteriophage lambda (λZAP) libraries of human cerebellum (female, 2 years), hippocampus (female, 2 years), temporal cortex (female, 2 years), substantia nigra (male and female 60 years), corpus striatum (caudate and putamen, males, 57 years) and fetal brain (female 17–18 weeks gestation) cDNAs (Stratagene Cloning Systems Inc., La Jolla, Calif. USA.; Cat.#935201, 936205, 935205, 936210, 936213 and 936206 respectively). DNA from these libraries was isolated essentially following the Qiagen Inc. (Chatsworth, Calif. USA) phage DNA preparation protocol. Human genomic DNA was obtained from Clontech Laboratories Inc. (Palto Alto, Calif. USA). The primer combinations were used to amplify EAA3 and EAA4 using either genomic or cDNA as a template, as previously described. PCR products of the correct sizes [PCR5-2/PCR5-26 (142bp), PCR5-3/PCR5-26 (315bp), 5int-3/5int-1 (138bp), PCR6-1/PCR6-3 (474bp), PCR6-1/PCR6-2 (221bp) and 6int-3/6int-1 (127bp)] were purified from an agarose gel and subcloned into pT7blue (Novagen Inc., Madison, Wis. USA) for screening and DNA sequencing.

Southern blot analysis—8 μg of human genomic DNA digested with single restriction enzymes (HindIII, PstI, BamHI and EcoRV) were electrophoresed on a 0.7% agarose gel, then transferred to a nylon membrane (Schleicher and Schuell Inc., Keene N.H. USA). The DNA was immobilized on the membrane using UV radiation covalent crosslinking. Purified PCR6-1/PCR6-2 (EAA4, TMI), 6int-3/6int-1 (EAA4, TMII) and 5int-3/5int-1 (EAA3, TMII) PCR amplification products were separately radiolabelled with [α-$^{32}$P]dCTP by the random priming method (Amersham Corp. Arlington Heights Ill. USA) and used to probe the genomic DNA. Hybridizations were carried out in 6× standard saline citrate (1× SSC is 0.15M NaCl, 0.015M Na.citrate, pH 7.6), 50% formamide, 5× Denhardt's solution, 0.5% SDS and 100 μg/ml sonicated salmon sperm DNA at 42° C. for 16 hours. The filters were washed with increasing stringencies up to 1× SSC/0.5%SDS, 60° C., for 20 min, before exposure to x-ray film at −80° C. for 72 hours.

EXAMPLE 8

Confirmation of RNA Editing of EAA3 (SEQ ID NO:3) and EAA4 (SEQ ID NO:5) Genes

RNA editing assay—Plasmid DNA was isolated and initially screened by restriction endonuclease digestion (FIG. 8). The occurrence of an internal restriction site [BstXI (EAA3), EcoRV (EAA4) or BamHI (EAA5)] was indicative of a correct sequence. The presence or absence of editing at the TMII Q/R site was determined by BbvI digestion. BbvI has the recognition sequence $^5$'GCAGC(N)$_8$ . . . $^3$', and as such will cleave the unedited sequence (GCAGC) and leave intact the altered form (GCGGC). A clear difference in the resulting restriction pattern of Q vs R forms provided a convenient method to categorize the clones. The TMI I/V and Y/C editing sites were confirmed by DNA sequencing, as were the smaller genomic fragments and a representative sample of TMII sites.

| | | | SOURCE OF cDNA | | | |
|---|---|---|---|---|---|---|
| EDITING STATUS | CORPUS STRIATUM | CEREBELLUM | FETAL BRAIN | HIPPO-CAMPUS | SUBSTANTIA NIGRA | TEMPORAL CORTEX |
| EAA4 | | | | | | |
| I.Y.Q | 4 | 2 | 25 | 6 | 36 | 11 |
| V.Y.Q | 0 | 0 | 0 | 0 | 0 | 0 |
| I.C.Q | 0 | 0 | 0 | 0 | 0 | 0 |
| V.C.Q | 1 | 0 | 0 | 1 | 0 | 0 |
| I.Y.R | 0 | 0 | 3 | 0 | 1 | 0 |
| V.Y.R | 0 | 0 | 0 | 0 | 0 | 0 |
| I.C.R | 19 | 24 | 1 | 0 | 0 | 0 |
| V.C.R | 0 | 3 | 2 | 14 | 31 | 0 |
| EAA3 | | | | | | |
| (Q) | 0 | 12 | 8 | 2 | 3 | 0 |
| (R) | 31 | 27 | 15 | 21 | 29 | 22 |

The table above reveals the relative frequency of TMI and TMII editing in EAA3 and EAA4 cDNAs amplified from different cDNA sources. The number of cDNA clones evaluated are listed according to their editing status and the tissue source.

EXAMPLE 9

Isolation of Genomic and cDNA Encoding EAA5

The procedure similar to that outlined in Example 7 was carried for another human CNS receptor, namely the EAA5 receptor, which is described in co-pending U.S. application Ser. No. 07/945,210, incorporated herein by reference. PCR primers for the same regions as those used for EAA4 were prepared and used to amplify EAA5 genomic DNA (obtained from Clontech) and cDNA (in human ZAP cDNA libraries obtained from Stratagene).

PCR7-2 5'-AATGATGCGTGTGGACAGGGC-3', (SEQ ID NO:28)

PCR7-3 5'-CCCCTGACCATCACCCATGT-3', (SEQ ID NO:29)

PCR7-6 5'-CTGGCTCCGAGGTGGTGGAA-3', (SEQ ID NO:30)
PCR7-15 5'-CCTTTGGGCATCAGCACAGAC-3', (SEQ ID NO:31)
PCR7-16 5'-CTGGCGATGACGAAGAGGAC-3', (SEQ ID NO:32)

The isolated EAA5 genomic DNA and cDNA were compared for sequence discrepancies expected in the TMI/II regions, and none were found indicating that editing does not occur in the EAA5 human CNS receptor. However, further analysis revealed two variations of EAA5 cDNA which result in amino acid substitutions in the predicted extracellular amino-terminal region: Ser-310→Ala and Arg-352→Gln. These variations can be attributed to RNA editing involving T→G and G→A substitutions.

What is claimed is:

1. An isolated unedited form of human EAA4 receptor subunit (SEQ ID NO:6).

2. An isolated hemi-edited form of human EAA4 receptor subunit (SEQ ID NO:6) comprising an isoleucine at position 536, a tyrosine at position 540 and an arginine at position 590.

3. An isolated hemi-edited form of human EAA4 receptor subunit (SEQ ID NO:6) comprising an isoleucine at position 536, a cysteine at position 540 and a glutamine at position 590.

4. An isolated hemi-edited form of human EAA4 receptor subunit (SEQ ID NO:6) comprising an isoleucine at position 536, a cysteine at position 540 and an arginine at position 590.

5. An isolated hemi-edited form of human EAA4 receptor subunit (SEQ ID NO:6) comprising a valine at position 536, a tyrosine at position 540 and a glutamine at position 590.

6. An isolated hemi-edited form of human EAA4 receptor subunit (SEQ ID NO:6) comprising a valine at position 536, a tyrosine at position 540 and an arginine at position 590.

7. An isolated hemi-edited form of human EAA4 receptor subunit (SEQ ID NO:6) comprising a valine at position 536, a cysteine at position 540 and a glutamine at position 590.

8. An isolated polynucleotide encoding an unedited form of human EAA4 receptor subunit (SEQ ID NO:6).

9. An isolated polynucleotide encoding a hemi-edited form of human EAA4 receptor subunit (SEQ ID NO:6) comprising an isoleucine at position 536, a tyrosine at position 540 and an arginine at position 590.

10. An isolated polynucleotide encoding a hemi-edited form of human EAA4 receptor subunit (SEQ ID NO:6) comprising an isoleucine at position 536, a cysteine at position 540 and a glutamine at position 590.

11. An isolated polynucleotide encoding a hemi-edited form of human EAA4 receptor subunit (SEQ ID NO:6) comprising an isoleucine at position 536, a cysteine at position 540 and an arginine at position 590.

12. An isolated polynucleotide encoding a hemi-edited form of human EAA4 receptor subunit (SEQ ID NO:6) comprising a valine at position 536, a tyrosine at position 540 and a glutamine at position 590.

13. An isolated polynucleotide encoding a hemi-edited form of human EAA4 receptor subunit (SEQ ID NO:6) comprising a valine at position 536, a tyrosine at position 540 and an arginine at position 590.

14. An isolated polynucleotide encoding a hemi-edited form of human EAA4 receptor subunit (SEQ ID NO:6) comprising a valine at position 536, a cysteine at position 540 and a glutamine at position 590.

15. A cell comprising a polynucleotide according to any one of claims 8 to 14 incorporated expressibly therein.

16. A method for identifying agents that modulate the editing of a human ionotropic glutamate receptor subunit in vivo, comprising;
   a) producing a human neuronal cell line comprising a polynucleotide according to any one of claims 8 to 14 incorporated expressibly therein, and that elaborates, upon culturing, the edited form of human EAA4 (SEQ ID NO:14);
   b) culturing the cell line in the presence of a candidate modulator of said editing; and
   c) determining the effects of said modulator on the elaboration of said edited form.

17. A method for identifying agents that modulate the editing of a human ionotropic glutamate receptor subunit in vivo as claimed in claim 16, wherein the human neuronal cell line comprises a polynucleotide encoding an unedited form of human EAA4 receptor subunit (SEQ ID NO:6) and elaborates, upon culturing, the edited form of human EAA4 (SEQ ID NO:14).

18. A method for identifying agents that modulate the editing of a human ionotropic glutamate receptor subunit in vivo as claimed in claim 16, wherein the human neuronal cell line comprises a polynucleotide encoding a hemi-edited form of human EAA4 receptor subunit (SEQ ID NO:6) comprising an isoleucine at position 536, a tyrosine at position 540 and an arginine at position 590 and elaborates, upon culturing, the edited form of human EAA4 (SEQ ID NO:14).

19. A method for identifying agents that modulate the editing of a human ionotropic glutamate receptor subunit in vivo as claimed in claim 16, wherein the human neuronal cell line comprises a polynucleotide encoding a hemi-edited form of human EAA4 receptor subunit (SEQ ID NO:6) comprising an isoleucine at position 536, a cysteine at position 540 and a glutamine at position 590 and elaborates, upon culturing, the edited form of human EAA4 (SEQ ID NO:14).

20. A method for identifying agents that modulate the editing of a human ionotropic glutamate receptor subunit in vivo as claimed in claim 16, wherein the human neuronal cell line comprises a polynucleotide encoding a hemi-edited form of human EAA4 receptor subunit (SEQ ID NO:6) comprising an isoleucine at position 536, a cysteine at position 540 and an arginine at position 590 and elaborates, upon culturing, the edited form of human EAA4 (SEQ ID NO:14).

21. A method for identifying agents that modulate the editing of a human ionotropic glutamate receptor subunit in vivo as claimed in claim 16, wherein the human neuronal cell line comprises a polynucleotide encoding a hemi-edited form of human EAA4 receptor subunit (SEQ ID NO:6) comprising a valine at position 536, a tyrosine at position 540 and a glutamine at position 590 and elaborates, upon culturing, the edited form of human EAA4 (SEQ ID NO:14).

22. A method for identifying agents that modulate the editing of a human ionotropic glutamate receptor subunit in vivo as claimed in claim 16, wherein the human neuronal cell line comprises a polynucleotide encoding a hemi-edited form of human EAA4 receptor subunit (SEQ ID NO:6) comprising a valine at position 536, a tyrosine at position 540 and an arginine at position 590 and elaborates, upon culturing, the edited form of human EAA4 (SEQ ID NO:14).

23. A method for identifying agents that modulate the editing of a human ionotropic glutamate receptor subunit in vivo as claimed in claim 16, wherein the human neuronal cell line comprises a polynucleotide encoding a hemi-edited form of human EAA4 receptor subunit (SEQ ID NO:6) comprising a valine at position 536, a cysteine at position 540 and a glutamine at position 590 and elaborates, upon culturing, the edited form of human EAA4 (SEQ ID NO:14).

24. A method for identifying a human ionotropic glutamate receptor ligand, which comprises:
   a) incubating a candidate ligand with a first ionotropic glutamate receptor comprising a subunit type selected from the group consisting of an unedited form of human EAA4 receptor subunit (SEQ ID NO:6), a hemi-edited form of human EAA4 receptor subunit (SEQ ID NO:6) comprising an isoleucine at position 536, a tyrosine at position 540 and an arginine at position 590, a hemi-edited form of human EAA4 receptor subunit (SEQ ID NO:6) comprising an isoleucine at position 536, a cysteine at position 540 and a glutamine at position 590, a hemi-edited form of human EAA4 receptor subunit (SEQ ID NO:6) comprising an isoleucine at position 536, a cysteine at position 540 and an arginine at position 590, a hemi-edited form of human EAA4 receptor subunit (SEQ ID NO:6) comprising a valine at position 536, a tyrosine at position 540 and a glutamine at position 590, a hemi-edited form of human EAA4 receptor subunit (SEQ ID NO:6) comprising a valine at position 536, a tyrosine at position 540 and an arginine at position 590, and a hemi-edited form of human EAA4 receptor subunit (SEQ ID NO:6) comprising a valine at position 536, a cysteine at position 540 and a glutamine at position 590, and determining the interaction between said first ionotropic glutamate receptor and said candidate ligand;
   b) incubating a candidate ligand with a second ionotropic glutamate receptor lacking one of the subunit types that was present in the first ionotropic glutamate receptor, and determining the interaction between said second ionotropic glutamate receptor and said candidate ligand; and either
   c) comparing the results of a) and b) and selecting a candidate ligand which interacts selectively with one of said receptor subunits; or
   d) selecting a candidate ligand which interacts substantially equivalently with both of said receptor subunits.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 3407 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 315..2966

(ix) FEATURE:
      (A) NAME/KEY: sig_peptide
      (B) LOCATION: 315..374

(ix) FEATURE:
      (A) NAME/KEY: mat_peptide
      (B) LOCATION: 375..2966

(xi) SEQUENCE DESCRIPTION: SEQ ID NO:1:

```
GAATTCCGTG AGTGCATGGG AGGGTGCTGA ATATTCCGAG ACACTGGGAC CACAGCGGCA         60

GCTCCGCTGA AAACTGCATT CAGCCAGTCC TCCGGACTTC TGGAGCGGGG ACAGGGCGCA        120

GGGCATCAGC AGCCACCAGC AGGACCTGGG AAATAGGGAT TCTTCTGCCT CCACTTCAGG        180

TTTTAGCAGC TTGGTGCTAA ATTGCTGTCT CAAAATGCAG AGGATCTAAT TTGCAGAGGA        240

AAACAGCCAA AGAAGGAAGA GGAGGAAAAG GAAAAAAAAA GGGGTATATT GTGGATGCTC        300

TACTTTTCTT GGAA ATG CAA AAG ATT ATG CAT ATT TCT GTC CTC CTT TCT         350
             Met Gln Lys Ile Met His Ile Ser Val Leu Leu Ser
             -20             -15                 -10

CCT GTT TTA TGG GGA CTG ATT TTT GGT GTC TCT TCT AAC AGC ATA CAG         398
Pro Val Leu Trp Gly Leu Ile Phe Gly Val Ser Ser Asn Ser Ile Gln
         -5                 1               5

ATA GGG GGG CTA TTT CCT AGG GGC GCC GAT CAA GAA TAC AGT GCA TTT         446
Ile Gly Gly Leu Phe Pro Arg Gly Ala Asp Gln Glu Tyr Ser Ala Phe
     10                 15                  20

CGA GTA GGG ATG GTT CAG TTT TCC ACT TCG GAG TTC AGA CTG ACA CCC         494
Arg Val Gly Met Val Gln Phe Ser Thr Ser Glu Phe Arg Leu Thr Pro
25                  30                  35                  40

CAC ATC GAC AAT TTG GAG GTG GCA AAC AGC TTC GCA GTC ACT AAT GCT         542
His Ile Asp Asn Leu Glu Val Ala Asn Ser Phe Ala Val Thr Asn Ala
                45                  50                  55

TTC TGC TCC CAG TTT TCG AGA GGA GTC TAT GCT ATT TTT GGA TTT TAT         590
Phe Cys Ser Gln Phe Ser Arg Gly Val Tyr Ala Ile Phe Gly Phe Tyr
             60                  65                  70
```

-continued

| | |
|---|---|
| GAC AAG AAG TCT GTA AAT ACC ATC ACA TCA TTT TGC GGA ACA CTC CAC<br>Asp Lys Lys Ser Val Asn Thr Ile Thr Ser Phe Cys Gly Thr Leu His<br>        75                   80                   85 | 638 |
| GTC TCC TTC ATC ACT CCC AGC TTC CCA ACA GAT GGC ACA CAT CCA TTT<br>Val Ser Phe Ile Thr Pro Ser Phe Pro Thr Asp Gly Thr His Pro Phe<br>     90                       95                  100 | 686 |
| GTC ATT CAG ATG AGA CCC GAC CTC AAA GGA GCT CTC CTT AGC TTG ATT<br>Val Ile Gln Met Arg Pro Asp Leu Lys Gly Ala Leu Leu Ser Leu Ile<br>105                  110                115                120 | 734 |
| GAA TAC TAT CAA TGG GAC AAG TTT GCA TAC CTC TAT GAC AGT GAC AGA<br>Glu Tyr Tyr Gln Trp Asp Lys Phe Ala Tyr Leu Tyr Asp Ser Asp Arg<br>               125                   130                 135 | 782 |
| GGC TTA TCA ACA CTG CAA GCT GTG CTG GAT TCT GCT GCT GAA AAG AAA<br>Gly Leu Ser Thr Leu Gln Ala Val Leu Asp Ser Ala Ala Glu Lys Lys<br>          140                  145                150 | 830 |
| TGG CAA GTG ACT GCT ATC AAT GTG GGA AAC ATT AAC AAT GAC AAG AAA<br>Trp Gln Val Thr Ala Ile Asn Val Gly Asn Ile Asn Asn Asp Lys Lys<br>        155                  160                165 | 878 |
| GAT GAG ATG TAC CGA TCA CTT TTT CAA GAT CTG GAG TTA AAA AAG GAA<br>Asp Glu Met Tyr Arg Ser Leu Phe Gln Asp Leu Glu Leu Lys Lys Glu<br>170                  175                180 | 926 |
| CGG CGT GTA ATT CTG GAC TGT GAA AGG GAT AAA GTA AAC GAC ATT GTA<br>Arg Arg Val Ile Leu Asp Cys Glu Arg Asp Lys Val Asn Asp Ile Val<br>185                  190                195                200 | 974 |
| GAC CAG GTT ATT ACC ATT GGA AAA CAC GTT AAA GGG TAC CAC TAC ATC<br>Asp Gln Val Ile Thr Ile Gly Lys His Val Lys Gly Tyr His Tyr Ile<br>               205                   210                 215 | 1022 |
| ATT GCA AAT CTG GGA TTT ACT GAT GGA GAC CTA TTA AAA ATC CAG TTT<br>Ile Ala Asn Leu Gly Phe Thr Asp Gly Asp Leu Leu Lys Ile Gln Phe<br>              220                   225                230 | 1070 |
| GGA GGT GCA AAT GTC TCT GGA TTT CAG ATA GTG GAC TAT GAT GAT TCG<br>Gly Gly Ala Asn Val Ser Gly Phe Gln Ile Val Asp Tyr Asp Asp Ser<br>          235                  240                245 | 1118 |
| TTG GTA TCT AAA TTT ATA GAA AGA TGG TCA ACA CTG GAA GAA AAA GAA<br>Leu Val Ser Lys Phe Ile Glu Arg Trp Ser Thr Leu Glu Glu Lys Glu<br>        250                  255                260 | 1166 |
| TAC CCT GGA GCT CAC ACA ACA ACA ATT AAG TAT ACT TCT GCT CTG ACC<br>Tyr Pro Gly Ala His Thr Thr Thr Ile Lys Tyr Thr Ser Ala Leu Thr<br>265                  270                275                280 | 1214 |
| TAT GAT GCC GTT CAA GTG ATG ACT GAA GCC TTC CGC AAC CTA AGG AAG<br>Tyr Asp Ala Val Gln Val Met Thr Glu Ala Phe Arg Asn Leu Arg Lys<br>               285                   290                 295 | 1262 |
| CAA AGA ATT GAA ATC TCC CGA AGG GGG AAT GCA GGA GAC TGT CTG GCA<br>Gln Arg Ile Glu Ile Ser Arg Arg Gly Asn Ala Gly Asp Cys Leu Ala<br>              300                   305                310 | 1310 |
| AAC CCA GCA GTG CCC TGG GGA CAA GGT GTA GAA ATA GAA AGG GCC CTC<br>Asn Pro Ala Val Pro Trp Gly Gln Gly Val Glu Ile Glu Arg Ala Leu<br>        315                  320                325 | 1358 |
| AAA CAG GTT CAG GTT GAA GGT CTC TCA GGA AAT ATA AAG TTT GAC CAG<br>Lys Gln Val Gln Val Glu Gly Leu Ser Gly Asn Ile Lys Phe Asp Gln<br>330                  335                340 | 1406 |
| AAT GGA AAA AGA ATA AAC TAT ACA ATT AAC ATC ATG GAG CTC AAA ACT<br>Asn Gly Lys Arg Ile Asn Tyr Thr Ile Asn Ile Met Glu Leu Lys Thr<br>345                  350                355                360 | 1454 |
| AAT GGG CCC CGG AAG ATT GGC TAC TGG AGT GAA GTG GAC AAA ATG GTT<br>Asn Gly Pro Arg Lys Ile Gly Tyr Trp Ser Glu Val Asp Lys Met Val<br>               365                   370                 375 | 1502 |
| GTT ACC CTT ACT GAG CTC CCT TCT GGA AAT GAC ACC TCT GGG CTT GAG<br>Val Thr Leu Thr Glu Leu Pro Ser Gly Asn Asp Thr Ser Gly Leu Glu<br>          380                  385                390 | 1550 |

```
AAT AAG ACT GTT GTT GTC ACC ACA ATT TTG GAA TCT CCG TAT GTT ATG    1598
Asn Lys Thr Val Val Val Thr Thr Ile Leu Glu Ser Pro Tyr Val Met
        395             400             405

ATG AAG AAA AAT CAT GAA ATG CTT GAA GGC AAT GAG CGC TAT GAG GGC    1646
Met Lys Lys Asn His Glu Met Leu Glu Gly Asn Glu Arg Tyr Glu Gly
    410             415             420

TAC TGT GTT GAC CTG GCT GCA GAA ATC GCC AAA CAT TGT GGG TTC AAG    1694
Tyr Cys Val Asp Leu Ala Ala Glu Ile Ala Lys His Cys Gly Phe Lys
425             430             435             440

TAC AAG TTG ACA ATT GTT GGT GAT GGC AAG TAT GGG GCC AGG GAT GCA    1742
Tyr Lys Leu Thr Ile Val Gly Asp Gly Lys Tyr Gly Ala Arg Asp Ala
            445             450             455

GAC ACG AAA ATT TGG AAT GGG ATG GTT GGA GAA CTT GTA TAT GGG AAA    1790
Asp Thr Lys Ile Trp Asn Gly Met Val Gly Glu Leu Val Tyr Gly Lys
        460             465             470

GCT GAT ATT GCA ATT GCT CCA TTA ACT ATT ACC CTT GTG AGA GAA GAG    1838
Ala Asp Ile Ala Ile Ala Pro Leu Thr Ile Thr Leu Val Arg Glu Glu
    475             480             485

GTG ATT GAC TTC TCA AAG CCC TTC ATG AGC CTC GGG ATA TCT ATC ATG    1886
Val Ile Asp Phe Ser Lys Pro Phe Met Ser Leu Gly Ile Ser Ile Met
490             495             500

ATC AAG AAG CCT CAG AAG TCC AAA CCA GGA GTG TTT TCC TTT CTT GAT    1934
Ile Lys Lys Pro Gln Lys Ser Lys Pro Gly Val Phe Ser Phe Leu Asp
505             510             515             520

CCT TTA GCC TAT GAG ATC TGG ATG TGC ATT GTT TTT GCC TAC ATT GGG    1982
Pro Leu Ala Tyr Glu Ile Trp Met Cys Ile Val Phe Ala Tyr Ile Gly
            525             530             535

GTC AGT GTA GTT TTA TTC CTG GTC AGC AGA TTT AGC CCC TAC GAG TGG    2030
Val Ser Val Val Leu Phe Leu Val Ser Arg Phe Ser Pro Tyr Glu Trp
        540             545             550

CAC ACT GAG GAG TTT GAA GAT GGA AGA GAA ACA CAA AGT AGT GAA TCA    2078
His Thr Glu Glu Phe Glu Asp Gly Arg Glu Thr Gln Ser Ser Glu Ser
    555             560             565

ACT AAT GAA TTT GGG ATT TTT AAT AGT CTC TGG TTT TCC TTG GGT GCC    2126
Thr Asn Glu Phe Gly Ile Phe Asn Ser Leu Trp Phe Ser Leu Gly Ala
570             575             580

TTT ATG CAG CAA GGA TGC GAT ATT TCG CCA AGA TCC CTC TCT GGG CGC    2174
Phe Met Gln Gln Gly Cys Asp Ile Ser Pro Arg Ser Leu Ser Gly Arg
585             590             595             600

ATT GTT GGA GGT GTG TGG TGG TTC TTT ACC CTG ATC ATA ATC TCC TCC    2222
Ile Val Gly Gly Val Trp Trp Phe Phe Thr Leu Ile Ile Ile Ser Ser
            605             610             615

TAC ACG GCT AAC TTA GCT GCC TTC CTG ACT GTA GAG AGG ATG GTG TCT    2270
Tyr Thr Ala Asn Leu Ala Ala Phe Leu Thr Val Glu Arg Met Val Ser
        620             625             630

CCC ATC GAA AGT GCT GAG GAT CTT TCT AAG CAA ACA GAA ATT GCT TAT    2318
Pro Ile Glu Ser Ala Glu Asp Leu Ser Lys Gln Thr Glu Ile Ala Tyr
    635             640             645

GGA ACA TTA GAC TCT GGC TCC ACT AAA GAG TTT TTC AGG AGA TCT AAA    2366
Gly Thr Leu Asp Ser Gly Ser Thr Lys Glu Phe Phe Arg Arg Ser Lys
650             655             660

ATT GCA GTG TTT GAT AAA ATG TGG ACC TAC ATG CGG AGT GCG GAG CCC    2414
Ile Ala Val Phe Asp Lys Met Trp Thr Tyr Met Arg Ser Ala Glu Pro
665             670             675             680

TCT GTG TTT GTG AGG ACT ACG GCC GAA GGG GTG GCT AGA GTG CGG AAG    2462
Ser Val Phe Val Arg Thr Thr Ala Glu Gly Val Ala Arg Val Arg Lys
            685             690             695

TCC AAA GGG AAA TAT GCC TAC TTG TTG GAG TCC ACG ATG AAC GAG TAC    2510
Ser Lys Gly Lys Tyr Ala Tyr Leu Leu Glu Ser Thr Met Asn Glu Tyr
        700             705             710
```

```
ATT GAG CAA AGG AAG CCT TGC GAC ACC ATG AAA GTT GGT GGA AAC CTG    2558
Ile Glu Gln Arg Lys Pro Cys Asp Thr Met Lys Val Gly Gly Asn Leu
            715                 720                 725

GAT TCC AAA GGC TAT GGC ATC GCA ACA CCT AAA GGA TCC TCA TTA GGA    2606
Asp Ser Lys Gly Tyr Gly Ile Ala Thr Pro Lys Gly Ser Ser Leu Gly
730                 735                 740

ACC CCA GTA AAT CTT GCA GTA TTG AAA CTC AGT GAG CAA GGC GTC TTA    2654
Thr Pro Val Asn Leu Ala Val Leu Lys Leu Ser Glu Gln Gly Val Leu
745                 750                 755                 760

GAC AAG CTG AAA AAC AAA TGG TGG TAC GAT AAA GGT GAA TGT GGA GCC    2702
Asp Lys Leu Lys Asn Lys Trp Trp Tyr Asp Lys Gly Glu Cys Gly Ala
            765                 770                 775

AAG GAC TCT GGA AGT AAG GAA AAG ACC AGT GCC CTC AGT CTG AGC AAC    2750
Lys Asp Ser Gly Ser Lys Glu Lys Thr Ser Ala Leu Ser Leu Ser Asn
            780                 785                 790

GTT GCT GGA GTA TTC TAC ATC CTT GTC GGG GGC CTT GGT TTG GCA ATG    2798
Val Ala Gly Val Phe Tyr Ile Leu Val Gly Gly Leu Gly Leu Ala Met
            795                 800                 805

CTG GTG GCT TTG ATT GAG TTC TGT TAC AAG TCA AGG GCC GAG GCG AAA    2846
Leu Val Ala Leu Ile Glu Phe Cys Tyr Lys Ser Arg Ala Glu Ala Lys
810                 815                 820

CGA ATG AAG GTG GCA AAG AAT GCA CAG AAT ATT AAC CCA TCT TCC TCG    2894
Arg Met Lys Val Ala Lys Asn Ala Gln Asn Ile Asn Pro Ser Ser Ser
825                 830                 835                 840

CAG AAT TCA CAG AAT TTT GCA ACT TAT AAG GAA GGT TAC AAC GTA TAT    2942
Gln Asn Ser Gln Asn Phe Ala Thr Tyr Lys Glu Gly Tyr Asn Val Tyr
            845                 850                 855

GGC ATC GAA AGT GTT AAA ATT TAGGGGATGA CCTTGAATGA TGCCATGAGG       2993
Gly Ile Glu Ser Val Lys Ile
            860

AACAAGGCAA GGCTGTCAAT TACAGGAAGT ACTGGAGAAA ATGGACGTGT TATGACTCCA  3053

GAATTTCCCA AAGCNGTGCA TGCTGTCCCT TACGTGAGTC CTGGCATGGG AATGAATGTC  3113

AGTGTGACTG ATCTCTCGTG ATTGATAAGA ACCTTTTGAG TGCCTTACAC AATGGTTTTC  3173

TTGTGTGTTT ATTGTCAAAG TGGTGAGAGG CATCCAGTAT CTTGAAGACT TTTCTTTCAG  3233

CCAAGAATTC TTAAATATGT GGAGTTCATC TTGAATTGTA AGGAATGATT AATTAAAACA  3293

CAACATCTTT TTCTACTCGA GTTACAGACA AAGCGTGGTG GACATGCACA GCTAACATGG  3353

AAGTACTATA ATTTACCTGA AGTCTTTGTA CAGACAACAA ACCTGTTTCT GCAG         3407

(2) INFORMATION FOR SEQ ID NO:2:

(i) SEQUENCE CHARACTERISTICS:
        (A) LENGTH: 883 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Lys Ile Met His Ile Ser Val Leu Leu Ser Pro Val Leu Trp
-20                 -15                 -10                 -5

Gly Leu Ile Phe Gly Val Ser Ser Asn Ser Ile Gln Ile Gly Gly Leu
                    1               5                   10

Phe Pro Arg Gly Ala Asp Gln Glu Tyr Ser Ala Phe Arg Val Gly Met
            15                  20                  25

Val Gln Phe Ser Thr Ser Glu Phe Arg Leu Thr Pro His Ile Asp Asn
        30                  35                  40
```

-continued

```
Leu Glu Val Ala Asn Ser Phe Ala Val Thr Asn Ala Phe Cys Ser Gln
 45                  50                  55                  60

Phe Ser Arg Gly Val Tyr Ala Ile Phe Gly Phe Tyr Asp Lys Lys Ser
                 65                  70                  75

Val Asn Thr Ile Thr Ser Phe Cys Gly Thr Leu His Val Ser Phe Ile
             80                  85                  90

Thr Pro Ser Phe Pro Thr Asp Gly Thr His Pro Phe Val Ile Gln Met
         95                 100                 105

Arg Pro Asp Leu Lys Gly Ala Leu Leu Ser Leu Ile Glu Tyr Tyr Gln
    110                 115                 120

Trp Asp Lys Phe Ala Tyr Leu Tyr Asp Ser Asp Arg Gly Leu Ser Thr
125                 130                 135                 140

Leu Gln Ala Val Leu Asp Ser Ala Ala Glu Lys Lys Trp Gln Val Thr
                145                 150                 155

Ala Ile Asn Val Gly Asn Ile Asn Asn Asp Lys Lys Asp Glu Met Tyr
            160                 165                 170

Arg Ser Leu Phe Gln Asp Leu Glu Leu Lys Lys Glu Arg Arg Val Ile
        175                 180                 185

Leu Asp Cys Glu Arg Asp Lys Val Asn Asp Ile Val Asp Gln Val Ile
    190                 195                 200

Thr Ile Gly Lys His Val Lys Gly Tyr His Tyr Ile Ile Ala Asn Leu
205                 210                 215                 220

Gly Phe Thr Asp Gly Asp Leu Leu Lys Ile Gln Phe Gly Gly Ala Asn
                225                 230                 235

Val Ser Gly Phe Gln Ile Val Asp Tyr Asp Asp Ser Leu Val Ser Lys
            240                 245                 250

Phe Ile Glu Arg Trp Ser Thr Leu Glu Glu Lys Glu Tyr Pro Gly Ala
        255                 260                 265

His Thr Thr Thr Ile Lys Tyr Thr Ser Ala Leu Thr Tyr Asp Ala Val
    270                 275                 280

Gln Val Met Thr Glu Ala Phe Arg Asn Leu Arg Lys Gln Arg Ile Glu
285                 290                 295                 300

Ile Ser Arg Arg Gly Asn Ala Gly Asp Cys Leu Ala Asn Pro Ala Val
                305                 310                 315

Pro Trp Gly Gln Gly Val Glu Ile Glu Arg Ala Leu Lys Gln Val Gln
            320                 325                 330

Val Glu Gly Leu Ser Gly Asn Ile Lys Phe Asp Gln Asn Gly Lys Arg
        335                 340                 345

Ile Asn Tyr Thr Ile Asn Ile Met Glu Leu Lys Thr Asn Gly Pro Arg
    350                 355                 360

Lys Ile Gly Tyr Trp Ser Glu Val Asp Lys Met Val Val Thr Leu Thr
365                 370                 375                 380

Glu Leu Pro Ser Gly Asn Asp Thr Ser Gly Leu Glu Asn Lys Thr Val
                385                 390                 395

Val Val Thr Thr Ile Leu Glu Ser Pro Tyr Val Met Met Lys Lys Asn
            400                 405                 410

His Glu Met Leu Glu Gly Asn Glu Arg Tyr Glu Gly Tyr Cys Val Asp
        415                 420                 425

Leu Ala Ala Glu Ile Ala Lys His Cys Gly Phe Lys Tyr Lys Leu Thr
    430                 435                 440

Ile Val Gly Asp Gly Lys Tyr Gly Ala Arg Asp Ala Asp Thr Lys Ile
445                 450                 455                 460
```

```
Trp Asn Gly Met Val Gly Glu Leu Val Tyr Gly Lys Ala Asp Ile Ala
            465                 470                 475
Ile Ala Pro Leu Thr Ile Thr Leu Val Arg Glu Glu Val Ile Asp Phe
            480                 485                 490
Ser Lys Pro Phe Met Ser Leu Gly Ile Ser Ile Met Ile Lys Lys Pro
            495                 500                 505
Gln Lys Ser Lys Pro Gly Val Phe Ser Phe Leu Asp Pro Leu Ala Tyr
510                 515                 520
Glu Ile Trp Met Cys Ile Val Phe Ala Tyr Ile Gly Val Ser Val Val
525                 530                 535                 540
Leu Phe Leu Val Ser Arg Phe Ser Pro Tyr Glu Trp His Thr Glu Glu
            545                 550                 555
Phe Glu Asp Gly Arg Glu Thr Gln Ser Ser Glu Ser Thr Asn Glu Phe
            560                 565                 570
Gly Ile Phe Asn Ser Leu Trp Phe Ser Leu Gly Ala Phe Met Gln Gln
            575                 580                 585
Gly Cys Asp Ile Ser Pro Arg Ser Leu Ser Gly Arg Ile Val Gly Gly
            590                 595                 600
Val Trp Trp Phe Phe Thr Leu Ile Ile Ile Ser Ser Tyr Thr Ala Asn
605                 610                 615                 620
Leu Ala Ala Phe Leu Thr Val Glu Arg Met Val Ser Pro Ile Glu Ser
            625                 630                 635
Ala Glu Asp Leu Ser Lys Gln Thr Glu Ile Ala Tyr Gly Thr Leu Asp
            640                 645                 650
Ser Gly Ser Thr Lys Glu Phe Phe Arg Arg Ser Lys Ile Ala Val Phe
            655                 660                 665
Asp Lys Met Trp Thr Tyr Met Arg Ser Ala Glu Pro Ser Val Phe Val
            670                 675                 680
Arg Thr Thr Ala Glu Gly Val Ala Arg Val Arg Lys Ser Lys Gly Lys
685                 690                 695                 700
Tyr Ala Tyr Leu Leu Glu Ser Thr Met Asn Glu Tyr Ile Glu Gln Arg
            705                 710                 715
Lys Pro Cys Asp Thr Met Lys Val Gly Gly Asn Leu Asp Ser Lys Gly
            720                 725                 730
Tyr Gly Ile Ala Thr Pro Lys Gly Ser Ser Leu Gly Thr Pro Val Asn
            735                 740                 745
Leu Ala Val Leu Lys Leu Ser Glu Gln Gly Val Leu Asp Lys Leu Lys
            750                 755                 760
Asn Lys Trp Trp Tyr Asp Lys Gly Glu Cys Gly Ala Lys Asp Ser Gly
765                 770                 775                 780
Ser Lys Glu Lys Thr Ser Ala Leu Ser Leu Ser Asn Val Ala Gly Val
            785                 790                 795
Phe Tyr Ile Leu Val Gly Gly Leu Gly Leu Ala Met Leu Val Ala Leu
            800                 805                 810
Ile Glu Phe Cys Tyr Lys Ser Arg Ala Glu Ala Lys Arg Met Lys Val
            815                 820                 825
Ala Lys Asn Ala Gln Asn Ile Asn Pro Ser Ser Ser Gln Asn Ser Gln
            830                 835                 840
Asn Phe Ala Thr Tyr Lys Glu Gly Tyr Asn Val Tyr Gly Ile Glu Ser
845                 850                 855                 860
Val Lys Ile
```

(2) INFORMATION FOR SEQ ID NO:3:

(i) SEQUENCE CHARACTERISTICS:
        (A) LENGTH: 3385 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 418..3132

(ix) FEATURE:
        (A) NAME/KEY: mat_peptide
        (B) LOCATION: 508..3132

(ix) FEATURE:
        (A) NAME/KEY: sig_peptide
        (B) LOCATION: 418..507

(xi) SEQUENCE DESCRIPTION: SEQ ID NO:3:

```
GAATTCCGTC TTCTTTCCCC CTTTTCCCTC CTCTGTCTGT GCCTATCCCC CGACTTTTGC        60

ATCTGACCAA AGGACGAATG AGGGAGACGT TCCTGCAGAT CGGGGCAGCA ACTTTCCTCA       120

GCTGGTCTCT GGGCTCCGGA GCCAGAGAGC GCTGATCCTC CGCGTCTGCG GCCCATGAAG       180

AGAGAGAGAG CCGTGATGGG CTAGCGACAG CACTGAGGAG CCCCGAGAGA GCTCAGCCTT       240

GCCAGCCAGC TCCGCGGTCC CACGCGGGTT CCCTCGAGCT CGCTCCGTGG GGAGCGCGCA       300

GCGTGCTTGG AACCGGAGCA TCCAGAGAGG ATGAGGCGGG GACCCGGCCC AAGTTGGGTG       360

CATCTCTCGG GCGTCCGGCA GCGGCTGTAT CTCGGCATGA ATTAAGAAGC TAGGAAG         417
```

```
ATG GAG CAC GGC ACA CTC CTC GCC CAG CCC GGG CTC TGG ACC AGG GAC        465
Met Glu His Gly Thr Leu Leu Ala Gln Pro Gly Leu Trp Thr Arg Asp
-30             -25                 -20                 -15

ACC AGC TGG GCA CTC CTC TAT TTC CTC TGC TAT ATC CTC CCT CAG ACC        513
Thr Ser Trp Ala Leu Leu Tyr Phe Leu Cys Tyr Ile Leu Pro Gln Thr
            -10                  -5                   1

GCC CCG CAA GTA CTC AGG ATC GGA GGG ATT TTT GAA ACA GTG GAA AAT        561
Ala Pro Gln Val Leu Arg Ile Gly Gly Ile Phe Glu Thr Val Glu Asn
         5                  10                  15

GAG CCT GTT AAT GTT GAA GAA TTA GCT TTC AAG TTT GCA GTC ACC AGC        609
Glu Pro Val Asn Val Glu Glu Leu Ala Phe Lys Phe Ala Val Thr Ser
     20                  25                  30

ATT AAC AGA AAC CGA ACC CTG ATG CCT AAC ACC ACA TTA ACC TAT GAC        657
Ile Asn Arg Asn Arg Thr Leu Met Pro Asn Thr Thr Leu Thr Tyr Asp
 35                  40                  45                  50

ATC CAG AGA ATT AAC CTT TTT GAT AGT TTT GAA GCC TCG CGG AGA GCA        705
Ile Gln Arg Ile Asn Leu Phe Asp Ser Phe Glu Ala Ser Arg Arg Ala
                 55                  60                  65

TGT GAC CAG CTG GCT CTT GGT GTG GCT GCT CTC TTT GGC CCT TCC CAT        753
Cys Asp Gln Leu Ala Leu Gly Val Ala Ala Leu Phe Gly Pro Ser His
             70                  75                  80

AGC TCC TCC GTC AGT GCT GTG CAG TCT ATT TGC AAT GCT CTC GAA GTT        801
Ser Ser Ser Val Ser Ala Val Gln Ser Ile Cys Asn Ala Leu Glu Val
         85                  90                  95

CCA CAC ATA CAG ACC CGC TGG AAA CAC CCC TCG GTG GAC AAC AAA GAT        849
Pro His Ile Gln Thr Arg Trp Lys His Pro Ser Val Asp Asn Lys Asp
    100                 105                 110

TTG TTT TAC ATC AAC CTT TAC CCA GAT TAT GCA GCT ATC AGC AGG GCG        897
Leu Phe Tyr Ile Asn Leu Tyr Pro Asp Tyr Ala Ala Ile Ser Arg Ala
115                 120                 125                 130
```

```
ATC CTG GAT CTG GTC CTC TAT TAC AAC TGG AAA ACA GTG ACA GTG GTG       945
Ile Leu Asp Leu Val Leu Tyr Tyr Asn Trp Lys Thr Val Thr Val Val
                135                 140                 145

TAT GAA GAC AGC ACA GGT CTA ATT CGT CTA CAA GAG CTC ATC AAA GCT       993
Tyr Glu Asp Ser Thr Gly Leu Ile Arg Leu Gln Glu Leu Ile Lys Ala
            150                 155                 160

CCC TCC AGA TAT AAT ATT AAA ATC AAA ATC CGC CAG CTG CCC TCT GGG      1041
Pro Ser Arg Tyr Asn Ile Lys Ile Lys Ile Arg Gln Leu Pro Ser Gly
        165                 170                 175

AAT AAA GAT GCC AAG CCT TTA CTC AAG GAG ATG AAG AAA GGC AAG GAG      1089
Asn Lys Asp Ala Lys Pro Leu Leu Lys Glu Met Lys Lys Gly Lys Glu
    180                 185                 190

TTC TAT GTG ATA TTT GAT TGT TCA CAT GAA ACA GCC GCT GAA ATC CTT      1137
Phe Tyr Val Ile Phe Asp Cys Ser His Glu Thr Ala Ala Glu Ile Leu
195                 200                 205                 210

AAG CAG ATT CTG TTC ATG GGC ATG ATG ACC GAA TAC TAT CAC TAC TTT      1185
Lys Gln Ile Leu Phe Met Gly Met Met Thr Glu Tyr Tyr His Tyr Phe
                215                 220                 225

TTC ACA ACC CTG GAC TTA TTT GCT TTG GAT CTG GAA CTC TAT AGG TAC      1233
Phe Thr Thr Leu Asp Leu Phe Ala Leu Asp Leu Glu Leu Tyr Arg Tyr
            230                 235                 240

AGT GGC GTA AAC ATG ACC GGG TTT GGG CTG CTT AAC ATT GAC AAC CCT      1281
Ser Gly Val Asn Met Thr Gly Phe Gly Leu Leu Asn Ile Asp Asn Pro
        245                 250                 255

CAC GTG TCA TCC ATC ATT GAG AAG TGG TCC ATG GAG AGA CTG CAG GCC      1329
His Val Ser Ser Ile Ile Glu Lys Trp Ser Met Glu Arg Leu Gln Ala
    260                 265                 270

CCA CCC AGG CCC GAG ACT GGC CTT TTG GAT GGC ATG ATG ACA ACT GAA      1377
Pro Pro Arg Pro Glu Thr Gly Leu Leu Asp Gly Met Met Thr Thr Glu
275                 280                 285                 290

GCG GCT CTG ATG TAC GAT GCT GTG TAC ATG GTG GCC ATT GCC TCG CAC      1425
Ala Ala Leu Met Tyr Asp Ala Val Tyr Met Val Ala Ile Ala Ser His
                295                 300                 305

CGG GCA TCC CAG CTG ACC GTC AGC TCC CTG CAG TGC CAT AGA CAT AAG      1473
Arg Ala Ser Gln Leu Thr Val Ser Ser Leu Gln Cys His Arg His Lys
            310                 315                 320

CCA TGG CGC CTC GGA CCC AGA TTT ATG AAC CTG ATC AAA GAG GCC CGG      1521
Pro Trp Arg Leu Gly Pro Arg Phe Met Asn Leu Ile Lys Glu Ala Arg
        325                 330                 335

TGG GAT GGC TTG ACT GGG CAT ATC ACC TTT AAT AAA ACC AAT GGC TTG      1569
Trp Asp Gly Leu Thr Gly His Ile Thr Phe Asn Lys Thr Asn Gly Leu
    340                 345                 350

AGG AAG GAT TTT GAT CTG GAC ATT ATT AGT CTC AAA GAG GAA GGA ACT      1617
Arg Lys Asp Phe Asp Leu Asp Ile Ile Ser Leu Lys Glu Glu Gly Thr
355                 360                 365                 370

GAA AAG ATT GGG ATT TGG AAT TCC AAC AGT GGG CTT AAC ATG ACG GAC      1665
Glu Lys Ile Gly Ile Trp Asn Ser Asn Ser Gly Leu Asn Met Thr Asp
                375                 380                 385

AGC AAC AAA GAC AAG TCC AGC AAT ATC ACT GAT TCA TTG GCC AAC AGA      1713
Ser Asn Lys Asp Lys Ser Ser Asn Ile Thr Asp Ser Leu Ala Asn Arg
            390                 395                 400

ACA CTC ATT GTC ACC ACC ATT CTG GAA GAA CCC TAT GTT ATG TAC AGG      1761
Thr Leu Ile Val Thr Thr Ile Leu Glu Glu Pro Tyr Val Met Tyr Arg
        405                 410                 415

AAA TCT GAT AAG CCT CTA TAT GGA AAT GAC AGA TTT GAA GGA TAT TGC      1809
Lys Ser Asp Lys Pro Leu Tyr Gly Asn Asp Arg Phe Glu Gly Tyr Cys
    420                 425                 430

CTA GAC CTG TTG AAA GAA TTG TCA AAC ATC CTG GGT TTC ATT TAT GAT      1857
Leu Asp Leu Leu Lys Glu Leu Ser Asn Ile Leu Gly Phe Ile Tyr Asp
435                 440                 445                 450
```

-continued

```
GTT AAA CTA GTT CCC GAT GGC AAA TAT GGG GCC CAG AAT GAC AAA GGG      1905
Val Lys Leu Val Pro Asp Gly Lys Tyr Gly Ala Gln Asn Asp Lys Gly
                455                 460                 465

GAG TGG AAC GGG ATG GTT AAA GAA CTC ATA GAT CAC AGG GCT GAC CTG      1953
Glu Trp Asn Gly Met Val Lys Glu Leu Ile Asp His Arg Ala Asp Leu
            470                 475                 480

GCA GTG GCT CCT CTT ACC ATC ACC TAC GTG CGG GAG AAA GTC ATT GAC      2001
Ala Val Ala Pro Leu Thr Ile Thr Tyr Val Arg Glu Lys Val Ile Asp
                485                 490                 495

TTC TCC AAA CCC TTC ATG ACC CTA GGC ATC AGC ATT CTC TAC CGG AAG      2049
Phe Ser Lys Pro Phe Met Thr Leu Gly Ile Ser Ile Leu Tyr Arg Lys
            500                 505                 510

CCC AAT GGT ACC AAT CCA GGC GTT TTC TCC TTC CTC AAC CCC CTG TCT      2097
Pro Asn Gly Thr Asn Pro Gly Val Phe Ser Phe Leu Asn Pro Leu Ser
515                 520                 525                 530

CCA GAT ATT TGG ATG TAT GTG CTC TTA GCC TGC TTG GGA GTC AGC TGT      2145
Pro Asp Ile Trp Met Tyr Val Leu Leu Ala Cys Leu Gly Val Ser Cys
            535                 540                 545

GTA CTC TTT GTG ATT GCA AGG TTT ACA CCC TAC GAG TGG TAT AAC CCC      2193
Val Leu Phe Val Ile Ala Arg Phe Thr Pro Tyr Glu Trp Tyr Asn Pro
                550                 555                 560

CAC CCA TGC AAC CCT GAC TCA GAC GTG GTG GAA AAC AAT TTT ACT TTA      2241
His Pro Cys Asn Pro Asp Ser Asp Val Val Glu Asn Asn Phe Thr Leu
            565                 570                 575

CTA AAT AGT TTC TGG TTT GGA GTT GGA GCT CTC ATG CAG CAA GGA TCA      2289
Leu Asn Ser Phe Trp Phe Gly Val Gly Ala Leu Met Gln Gln Gly Ser
580                 585                 590

GAG CTG ATG CCC AAA GCT CTA TCG ACC AGA ATA GTT GGA GGG ATA TGG      2337
Glu Leu Met Pro Lys Ala Leu Ser Thr Arg Ile Val Gly Gly Ile Trp
595                 600                 605                 610

TGG TTT TTC ACC CTA ATC ATC ATT TCA TCC TAC ACG GCC AAT CTG GCT      2385
Trp Phe Phe Thr Leu Ile Ile Ile Ser Ser Tyr Thr Ala Asn Leu Ala
                615                 620                 625

GCC TTC TTG ACA GTA GAG AGA ATG GAA TCC CCC ATA GAT TCG GCA GAT      2433
Ala Phe Leu Thr Val Glu Arg Met Glu Ser Pro Ile Asp Ser Ala Asp
            630                 635                 640

GAT CTG GCA AAG CAA ACC AAG ATA GAA TAT GGG GCG GTT AGA GAT GGA      2481
Asp Leu Ala Lys Gln Thr Lys Ile Glu Tyr Gly Ala Val Arg Asp Gly
                645                 650                 655

TCA ACA ATG ACC TTC TTC AAG AAA TCA AAA ATC TCC ACC TAT GAG AAG      2529
Ser Thr Met Thr Phe Phe Lys Lys Ser Lys Ile Ser Thr Tyr Glu Lys
660                 665                 670

ATG TGG GCT TTC ATG AGC AGC AGG CAG CAG ACC GCC CTG GTA AGA AAC      2577
Met Trp Ala Phe Met Ser Ser Arg Gln Gln Thr Ala Leu Val Arg Asn
675                 680                 685                 690

AGT GAT GAG GGG ATC CAG AGA GTG CTC ACC ACA GAC TAC GCG CTG CTG      2625
Ser Asp Glu Gly Ile Gln Arg Val Leu Thr Thr Asp Tyr Ala Leu Leu
                695                 700                 705

ATG GAG TCC ACC AGC ATT GAG TAT GTG ACG CAG AGA AAC TGC AAC CTC      2673
Met Glu Ser Thr Ser Ile Glu Tyr Val Thr Gln Arg Asn Cys Asn Leu
            710                 715                 720

ACT CAG ATC GGG GGC CTC ATT GAC TCC AAA GGT TAC GGA GTG GGA ACA      2721
Thr Gln Ile Gly Gly Leu Ile Asp Ser Lys Gly Tyr Gly Val Gly Thr
                725                 730                 735

CCT ATT GGT TCT CCT TAC CGG GAT AAA ATT ACT ATT GCT ATT CTT CAA      2769
Pro Ile Gly Ser Pro Tyr Arg Asp Lys Ile Thr Ile Ala Ile Leu Gln
740                 745                 750

CTC CAA GAA GAA GGG AAG CTG CAT ATG ATG AAA GAG AAG TGG TGG CGT      2817
Leu Gln Glu Glu Gly Lys Leu His Met Met Lys Glu Lys Trp Trp Arg
755                 760                 765                 770
```

```
GGG AAT GGC TGC CCC GAG GAA GAC AAC AAA GAA GCC AGT GCC CTG GGA      2865
Gly Asn Gly Cys Pro Glu Glu Asp Asn Lys Glu Ala Ser Ala Leu Gly
                775                 780                 785

GTG GAA AAT ATT GGA GGC ATC TTC ATT GTT CTG GCT GCC GGA CTG GTC      2913
Val Glu Asn Ile Gly Gly Ile Phe Ile Val Leu Ala Ala Gly Leu Val
                790                 795                 800

CTT TCT GTA TTT GTA GCT ATT GGA GAA TTC ATA TAC AAA TCA CGG AAG      2961
Leu Ser Val Phe Val Ala Ile Gly Glu Phe Ile Tyr Lys Ser Arg Lys
                805                 810                 815

AAT AAT GAT ATT GAA CAG TGT CTC TCT TTC AAC GCT ATC ATG GAA GAA      3009
Asn Asn Asp Ile Glu Gln Cys Leu Ser Phe Asn Ala Ile Met Glu Glu
                820                 825                 830

CTG GGA ATC TCA CTG AAG AAT CAG AAA AAA ATA AAG AAA AAG TCA AGA      3057
Leu Gly Ile Ser Leu Lys Asn Gln Lys Lys Ile Lys Lys Lys Ser Arg
835                 840                 845                 850

ACT AAG GGG AAA TCT TCC TTC ACA AGT ATC CTT ACT TGT CAT CAG AGA      3105
Thr Lys Gly Lys Ser Ser Phe Thr Ser Ile Leu Thr Cys His Gln Arg
                855                 860                 865

CGA ACT CAG AGA AAA GAG ACT GTG GCG TGATCCAAGG AAACGCCTGT            3152
Arg Thr Gln Arg Lys Glu Thr Val Ala
                870             875

AGGAAGAAAA AGGATGCATT CCCTACAGAT TTTTGGAGAA AGGATTTCTG AGGAGTTGTG    3212

TGATGTGTTT CCATATATCT ATATCCATAA CTCTGATTAT GAATACAGAT ATAAGAAATA    3272

CAAAAGTTTA AAAAGCTCAC ATAGATATGA CTTGGGAAGT GACACCAGTT CTTTTAAAAT    3332

AAATTTGTAT GCACAAAAAA AAAAAAAAAA AAAAAAAAAA AAAAAGGAA TTC            3385

(2) INFORMATION FOR SEQ ID NO:4:

(i) SEQUENCE CHARACTERISTICS:
        (A) LENGTH: 905 amino acids
        (B) TYPE: amino acid
        (D) TOPOLOGY: linear (ii) MOLECULE TYPE: protein (xi) SEQUENCE DESCRIPTION: SEQ ID NO:4:

Met Glu His Gly Thr Leu Leu Ala Gln Pro Gly Leu Trp Thr Arg Asp
-30                 -25                 -20                 -15

Thr Ser Trp Ala Leu Leu Tyr Phe Leu Cys Tyr Ile Leu Pro Gln Thr
                -10                 -5                   1

Ala Pro Gln Val Leu Arg Ile Gly Gly Ile Phe Glu Thr Val Glu Asn
                5                   10                  15

Glu Pro Val Asn Val Glu Glu Leu Ala Phe Lys Phe Ala Val Thr Ser
        20                  25                  30

Ile Asn Arg Asn Arg Thr Leu Met Pro Asn Thr Thr Leu Thr Tyr Asp
35                  40                  45                  50

Ile Gln Arg Ile Asn Leu Phe Asp Ser Phe Glu Ala Ser Arg Arg Ala
                55                  60                  65

Cys Asp Gln Leu Ala Leu Gly Val Ala Ala Leu Phe Gly Pro Ser His
                70                  75                  80

Ser Ser Ser Val Ser Ala Val Gln Ser Ile Cys Asn Ala Leu Glu Val
        85                  90                  95

Pro His Ile Gln Thr Arg Trp Lys His Pro Ser Val Asp Asn Lys Asp
        100                 105                 110

Leu Phe Tyr Ile Asn Leu Tyr Pro Asp Tyr Ala Ala Ile Ser Arg Ala
115                 120                 125                 130
```

-continued

```
Ile Leu Asp Leu Val Leu Tyr Tyr Asn Trp Lys Thr Val Thr Val Val
            135                 140                 145

Tyr Glu Asp Ser Thr Gly Leu Ile Arg Leu Gln Glu Leu Ile Lys Ala
        150                 155                 160

Pro Ser Arg Tyr Asn Ile Lys Ile Lys Ile Arg Gln Leu Pro Ser Gly
        165                 170                 175

Asn Lys Asp Ala Lys Pro Leu Leu Lys Glu Met Lys Lys Gly Lys Glu
    180                 185                 190

Phe Tyr Val Ile Phe Asp Cys Ser His Glu Thr Ala Ala Glu Ile Leu
195                 200                 205                 210

Lys Gln Ile Leu Phe Met Gly Met Met Thr Glu Tyr Tyr His Tyr Phe
            215                 220                 225

Phe Thr Thr Leu Asp Leu Phe Ala Leu Asp Leu Glu Leu Tyr Arg Tyr
            230                 235                 240

Ser Gly Val Asn Met Thr Gly Phe Gly Leu Leu Asn Ile Asp Asn Pro
        245                 250                 255

His Val Ser Ser Ile Ile Glu Lys Trp Ser Met Glu Arg Leu Gln Ala
    260                 265                 270

Pro Pro Arg Pro Glu Thr Gly Leu Leu Asp Gly Met Met Thr Thr Glu
275                 280                 285                 290

Ala Ala Leu Met Tyr Asp Ala Val Tyr Met Val Ala Ile Ala Ser His
            295                 300                 305

Arg Ala Ser Gln Leu Thr Val Ser Ser Leu Gln Cys His Arg His Lys
            310                 315                 320

Pro Trp Arg Leu Gly Pro Arg Phe Met Asn Leu Ile Lys Glu Ala Arg
        325                 330                 335

Trp Asp Gly Leu Thr Gly His Ile Thr Phe Asn Lys Thr Asn Gly Leu
    340                 345                 350

Arg Lys Asp Phe Asp Leu Asp Ile Ile Ser Leu Lys Glu Glu Gly Thr
355                 360                 365                 370

Glu Lys Ile Gly Ile Trp Asn Ser Asn Ser Gly Leu Asn Met Thr Asp
            375                 380                 385

Ser Asn Lys Asp Lys Ser Ser Asn Ile Thr Asp Ser Leu Ala Asn Arg
        390                 395                 400

Thr Leu Ile Val Thr Thr Ile Leu Glu Glu Pro Tyr Val Met Tyr Arg
        405                 410                 415

Lys Ser Asp Lys Pro Leu Tyr Gly Asn Asp Arg Phe Glu Gly Tyr Cys
    420                 425                 430

Leu Asp Leu Leu Lys Glu Leu Ser Asn Ile Leu Gly Phe Ile Tyr Asp
435                 440                 445                 450

Val Lys Leu Val Pro Asp Gly Lys Tyr Gly Ala Gln Asn Asp Lys Gly
            455                 460                 465

Glu Trp Asn Gly Met Val Lys Glu Leu Ile Asp His Arg Ala Asp Leu
            470                 475                 480

Ala Val Ala Pro Leu Thr Ile Thr Tyr Val Arg Glu Lys Val Ile Asp
            485                 490                 495

Phe Ser Lys Pro Phe Met Thr Leu Gly Ile Ser Ile Leu Tyr Arg Lys
        500                 505                 510

Pro Asn Gly Thr Asn Pro Gly Val Phe Ser Phe Leu Asn Pro Leu Ser
515                 520                 525                 530

Pro Asp Ile Trp Met Tyr Val Leu Leu Ala Cys Leu Gly Val Ser Cys
            535                 540                 545
```

Val Leu Phe Val Ile Ala Arg Phe Thr Pro Tyr Glu Trp Tyr Asn Pro
        550                 555                 560

His Pro Cys Asn Pro Asp Ser Asp Val Val Glu Asn Asn Phe Thr Leu
            565                 570                 575

Leu Asn Ser Phe Trp Phe Gly Val Gly Ala Leu Met Gln Gln Gly Ser
        580                 585                 590

Glu Leu Met Pro Lys Ala Leu Ser Thr Arg Ile Val Gly Gly Ile Trp
595                 600                 605                 610

Trp Phe Phe Thr Leu Ile Ile Ile Ser Ser Tyr Thr Ala Asn Leu Ala
                615                 620                 625

Ala Phe Leu Thr Val Glu Arg Met Glu Ser Pro Ile Asp Ser Ala Asp
            630                 635                 640

Asp Leu Ala Lys Gln Thr Lys Ile Glu Tyr Gly Ala Val Arg Asp Gly
        645                 650                 655

Ser Thr Met Thr Phe Phe Lys Lys Ser Lys Ile Ser Thr Tyr Glu Lys
        660                 665                 670

Met Trp Ala Phe Met Ser Ser Arg Gln Gln Thr Ala Leu Val Arg Asn
675                 680                 685                 690

Ser Asp Glu Gly Ile Gln Arg Val Leu Thr Thr Asp Tyr Ala Leu Leu
                695                 700                 705

Met Glu Ser Thr Ser Ile Glu Tyr Val Thr Gln Arg Asn Cys Asn Leu
            710                 715                 720

Thr Gln Ile Gly Gly Leu Ile Asp Ser Lys Gly Tyr Gly Val Gly Thr
        725                 730                 735

Pro Ile Gly Ser Pro Tyr Arg Asp Lys Ile Thr Ile Ala Ile Leu Gln
        740                 745                 750

Leu Gln Glu Glu Gly Lys Leu His Met Met Lys Glu Lys Trp Trp Arg
755                 760                 765                 770

Gly Asn Gly Cys Pro Glu Glu Asp Asn Lys Glu Ala Ser Ala Leu Gly
                775                 780                 785

Val Glu Asn Ile Gly Gly Ile Phe Ile Val Leu Ala Ala Gly Leu Val
            790                 795                 800

Leu Ser Val Phe Val Ala Ile Gly Glu Phe Ile Tyr Lys Ser Arg Lys
        805                 810                 815

Asn Asn Asp Ile Glu Gln Cys Leu Ser Phe Asn Ala Ile Met Glu Glu
        820                 825                 830

Leu Gly Ile Ser Leu Lys Asn Gln Lys Lys Ile Lys Lys Lys Ser Arg
835                 840                 845                 850

Thr Lys Gly Lys Ser Ser Phe Thr Ser Ile Leu Thr Cys His Gln Arg
                855                 860                 865

Arg Thr Gln Arg Lys Glu Thr Val Ala
            870                 875

(2) INFORMATION FOR SEQ ID NO:5:

(i) SEQUENCE CHARACTERISTICS:
        (A) LENGTH: 2878 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig_peptide
        (B) LOCATION: 134..226

-continued

```
    (ix) FEATURE:
         (A) NAME/KEY: mat_peptide
         (B) LOCATION: 227..2860

(ix) FEATURE:
         (A) NAME/KEY: CDS
         (B) LOCATION: 134..2860

(xi) SEQUENCE DESCRIPTION: SEQ ID NO:5:

GAATTCCCTC TCTATGACCA TGCCGTGATC GTGTCTGCGG TCACCACTCG ACGCATCCTC        60

ATTTCTACCC GAACCCAGGA GCCGAACGCT AGATCGGGGA AGTGGGTGCC GTGCGTGTGG       120

GCACAGAAAC ACC ATG AAG ATT ATT TTC CCG ATT CTA AGT AAT CCA GTC         169
            Met Lys Ile Ile Phe Pro Ile Leu Ser Asn Pro Val
            -31 -30             -25                 -20

TTC AGG CGC ACC GTT AAA CTC CTG CTC TGT TTA CTG TGG ATT GGA TAT        217
Phe Arg Arg Thr Val Lys Leu Leu Leu Cys Leu Leu Trp Ile Gly Tyr
            -15             -10                  -5

TCT CAA GGA ACC ACA CAT GTA TTA AGA TTT GGT GGT ATT TTT GAA TAT        265
Ser Gln Gly Thr Thr His Val Leu Arg Phe Gly Gly Ile Phe Glu Tyr
         1               5                  10

GTG GAA TCT GGC CCA ATG GGA GCT GAG GAA CTT GCA TTC AGA TTT GCT        313
Val Glu Ser Gly Pro Met Gly Ala Glu Glu Leu Ala Phe Arg Phe Ala
 15              20                  25

GTG AAC ACA ATT AAC AGA AAC AGA ACA TTG CTA CCC AAT ACT ACC CTT        361
Val Asn Thr Ile Asn Arg Asn Arg Thr Leu Leu Pro Asn Thr Thr Leu
 30              35                  40                  45

ACC TAT GAT ACC CAG AAG ATA AAC CTT TAT GAT AGT TTT GAA GCA TCC        409
Thr Tyr Asp Thr Gln Lys Ile Asn Leu Tyr Asp Ser Phe Glu Ala Ser
                 50                  55                  60

AAG AAA GCC TGT GAT CAG CTG TCT CTT GGG GTG GCT GCC ATC TTC GGG        457
Lys Lys Ala Cys Asp Gln Leu Ser Leu Gly Val Ala Ala Ile Phe Gly
             65                  70                  75

CCT TCA CAC AGC TCA TCA GCA AAC GCA GTG CAG TCC ATC TGC AAT GCT        505
Pro Ser His Ser Ser Ser Ala Asn Ala Val Gln Ser Ile Cys Asn Ala
                 80                  85                  90

CTG GGA GTT CCC CAC ATA CAG ACC CGC TGG AAG CAC CAG GTG TCA GAC        553
Leu Gly Val Pro His Ile Gln Thr Arg Trp Lys His Gln Val Ser Asp
         95                 100                 105

AAC AAA GAT TCC TTC TAT GTC AGT CTC TAC CCA GAC TTC TCT TCA CTC        601
Asn Lys Asp Ser Phe Tyr Val Ser Leu Tyr Pro Asp Phe Ser Ser Leu
110                 115                 120                 125

AGC CGT GCC ATT TTA GAC CTG GTG CAG TTT TTC AAG TGG AAA ACC GTC        649
Ser Arg Ala Ile Leu Asp Leu Val Gln Phe Phe Lys Trp Lys Thr Val
                130                 135                 140

ACG GTT GTG TAT GAT GAC AGC ACT GGT CTC ATT CGT TTG CAA GAG CTC        697
Thr Val Val Tyr Asp Asp Ser Thr Gly Leu Ile Arg Leu Gln Glu Leu
            145                 150                 155

ATC AAA GCT CCA TCA AGG TAT AAT CTT CGA CTC AAA ATT CGT CAG TTA        745
Ile Lys Ala Pro Ser Arg Tyr Asn Leu Arg Leu Lys Ile Arg Gln Leu
                160                 165                 170

CCT GCT GAT ACA AAG GAT GCA AAA CCC TTA CTA AAA GAA ATG AAA AGA        793
Pro Ala Asp Thr Lys Asp Ala Lys Pro Leu Leu Lys Glu Met Lys Arg
175                 180                 185

GGC AAG GAG TTT CAT GTA ATC TTT GAT TGT AGC CAT GAA ATG GCA GCA        841
Gly Lys Glu Phe His Val Ile Phe Asp Cys Ser His Glu Met Ala Ala
190                 195                 200                 205

GGC ATT TTA AAA CAG GCA TTA GCT ATG GGA ATG ATG ACA GAA TAC TAT        889
Gly Ile Leu Lys Gln Ala Leu Ala Met Gly Met Met Thr Glu Tyr Tyr
                210                 215                 220
```

```
CAT TAT ATC TTT ACC ACT CTG GAC CTC TTT GCT CTT GAT GTT GAG CCC        937
His Tyr Ile Phe Thr Thr Leu Asp Leu Phe Ala Leu Asp Val Glu Pro
        225                 230                 235

TAC CGA TAC AGT GGT GTT AAC ATG ACA GGG TTC AGA ATA TTA AAT ACA        985
Tyr Arg Tyr Ser Gly Val Asn Met Thr Gly Phe Arg Ile Leu Asn Thr
    240                 245                 250

GAA AAT ACC CAA GTC TCC TCC ATC ATT GAA AAG TGG TCG ATG GAA CGA       1033
Glu Asn Thr Gln Val Ser Ser Ile Ile Glu Lys Trp Ser Met Glu Arg
255                 260                 265

TTG CAG GCA CCT CCG AAA CCC GAT TCA GGT TTG CTG GAT GGA TTT ATG       1081
Leu Gln Ala Pro Pro Lys Pro Asp Ser Gly Leu Leu Asp Gly Phe Met
270                 275                 280                 285

ACG ACT GAT GCT GCT CTA ATG TAT GAT GCT GTG CAT GTG GTG TCT GTG       1129
Thr Thr Asp Ala Ala Leu Met Tyr Asp Ala Val His Val Val Ser Val
                290                 295                 300

GCC GTT CAA CAG TTT CCC CAG ATG ACA GTC AGT TCC TTG CAG TGT AAT       1177
Ala Val Gln Gln Phe Pro Gln Met Thr Val Ser Ser Leu Gln Cys Asn
            305                 310                 315

CGA CAT AAA CCC TGG CGC TTC GGG ACC CGC TTT ATG AGT CTA ATT AAA       1225
Arg His Lys Pro Trp Arg Phe Gly Thr Arg Phe Met Ser Leu Ile Lys
        320                 325                 330

GAG GCA CAT TGG GAA GGC CTC ACA GGC AGA ATA ACT TTC AAC AAA ACC       1273
Glu Ala His Trp Glu Gly Leu Thr Gly Arg Ile Thr Phe Asn Lys Thr
    335                 340                 345

AAT GGC TTG AGA ACA GAT TTT GAT TTG GAT GTG ATC AGT CTG AAG GAA       1321
Asn Gly Leu Arg Thr Asp Phe Asp Leu Asp Val Ile Ser Leu Lys Glu
350                 355                 360                 365

GAA GGT CTA GAA AAG ATT GGA ACG TGG GAT CCA GCC AGT GGC CTG AAT       1369
Glu Gly Leu Glu Lys Ile Gly Thr Trp Asp Pro Ala Ser Gly Leu Asn
                370                 375                 380

ATG ACA GAA AGT CAA AAG GGA AAG CCA GCG AAC ATC ACA GAT TCC TTA       1417
Met Thr Glu Ser Gln Lys Gly Lys Pro Ala Asn Ile Thr Asp Ser Leu
            385                 390                 395

TCC AAT CGT TCT TTG ATT GTT ACC ACC ATT TTG GAA GAG CCT TAT GTC       1465
Ser Asn Arg Ser Leu Ile Val Thr Thr Ile Leu Glu Glu Pro Tyr Val
        400                 405                 410

CTT TTT AAG AAG TCT GAC AAA CCT CTC TAT GGT AAT GAT CGA TTT GAA       1513
Leu Phe Lys Lys Ser Asp Lys Pro Leu Tyr Gly Asn Asp Arg Phe Glu
    415                 420                 425

GGC TAT TGC ATT GAT CTC CTC AGA GAG TTA TCT ACA ATC CTT GGC TTT       1561
Gly Tyr Cys Ile Asp Leu Leu Arg Glu Leu Ser Thr Ile Leu Gly Phe
430                 435                 440                 445

ACA TAT GAA ATT AGA CTT GTG GAA GAT GGG AAA TAT GGA GCC CAG GAT       1609
Thr Tyr Glu Ile Arg Leu Val Glu Asp Gly Lys Tyr Gly Ala Gln Asp
                450                 455                 460

GAT GCC AAT GGA CAA TGG AAT GGA ATG GTT CGT GAA CTA ATT GAT CAT       1657
Asp Ala Asn Gly Gln Trp Asn Gly Met Val Arg Glu Leu Ile Asp His
            465                 470                 475

AAA GCT GAC CTT GCA GTT GCT CCA CTG GCT ATT ACC TAT GTT CGA GAG       1705
Lys Ala Asp Leu Ala Val Ala Pro Leu Ala Ile Thr Tyr Val Arg Glu
        480                 485                 490

AAG GTC ATC GAC TTT TCC AAG CCC TTT ATG ACA CTT GGA ATA AGT ATT       1753
Lys Val Ile Asp Phe Ser Lys Pro Phe Met Thr Leu Gly Ile Ser Ile
    495                 500                 505

TTG TAC CGC AAG CCC AAT GGT ACA AAC CCA GGC GTC TTC TCC TTC CTG       1801
Leu Tyr Arg Lys Pro Asn Gly Thr Asn Pro Gly Val Phe Ser Phe Leu
510                 515                 520                 525

AAT CCT CTC TCC CCT GAT ATC TGG ATG TAT ATT CTG CTG GCT TAC TTG       1849
Asn Pro Leu Ser Pro Asp Ile Trp Met Tyr Ile Leu Leu Ala Tyr Leu
                530                 535                 540
```

```
GGT GTC AGT TGT GTG CTC TTT GTC ATA GCC AGG TTT AGT CCT TAT GAG     1897
Gly Val Ser Cys Val Leu Phe Val Ile Ala Arg Phe Ser Pro Tyr Glu
        545                 550                 555

TGG TAT AAT CCA CAC CCT TGC AAC CCT GAC TCA GAC GTG GTG GAA AAC     1945
Trp Tyr Asn Pro His Pro Cys Asn Pro Asp Ser Asp Val Val Glu Asn
        560                 565                 570

AAT TTT ACC TTG CTA AAT AGT TTC TGG TTT GGA GTT GGA GCT CTC ATG     1993
Asn Phe Thr Leu Leu Asn Ser Phe Trp Phe Gly Val Gly Ala Leu Met
575                 580                 585

CAG CAA GGT TCT GAG CTC ATG CCC AAA GCA CTG TCC ACC AGG ATA GTG     2041
Gln Gln Gly Ser Glu Leu Met Pro Lys Ala Leu Ser Thr Arg Ile Val
590                 595                 600                 605

GGA GGC ATT TGG TGG TTT TTC ACA CTT ATC ATC ATT TCT TCG TAT ACT     2089
Gly Gly Ile Trp Trp Phe Phe Thr Leu Ile Ile Ile Ser Ser Tyr Thr
            610                 615                 620

GCT AAC TTA GCC GCC TTT CTG ACA GTG GAA CGC ATG GAA TCC CCT ATT     2137
Ala Asn Leu Ala Ala Phe Leu Thr Val Glu Arg Met Glu Ser Pro Ile
                625                 630                 635

GAC TCT GCT GAT GAT TTA GCT AAA CAA ACC AAG ATA GAA TAT GGA GCA     2185
Asp Ser Ala Asp Asp Leu Ala Lys Gln Thr Lys Ile Glu Tyr Gly Ala
                    640                 645                 650

GTA GAG GAT GGT GCA ACC ATG ACT TTT TTC AAG AAA TCA AAA ATC TCC     2233
Val Glu Asp Gly Ala Thr Met Thr Phe Phe Lys Lys Ser Lys Ile Ser
655                 660                 665

ACG TAT GAC AAA ATG TGG GCC TTT ATG AGT AGC AGA AGG CAG TCA GTG     2281
Thr Tyr Asp Lys Met Trp Ala Phe Met Ser Ser Arg Arg Gln Ser Val
670                 675                 680                 685

CTG GTC AAA AGT AAT GAA GAA GGA ATC CAG CGA GTC CTC ACC TCT GAT     2329
Leu Val Lys Ser Asn Glu Glu Gly Ile Gln Arg Val Leu Thr Ser Asp
                690                 695                 700

TAT GCT TTC CTA ATG GAG TCA ACA ACC ATC GAG TTT GTT ACC CAG CGG     2377
Tyr Ala Phe Leu Met Glu Ser Thr Thr Ile Glu Phe Val Thr Gln Arg
                    705                 710                 715

AAC TGT AAC CTG ACA CAG ATT GGC GGC CTT ATA GAC TCT AAA GGT TAT     2425
Asn Cys Asn Leu Thr Gln Ile Gly Gly Leu Ile Asp Ser Lys Gly Tyr
                720                 725                 730

GGC GTT GGC ACT CCC ATG GGT TCT CCA TAT CGA GAC AAA ATT ACC ATA     2473
Gly Val Gly Thr Pro Met Gly Ser Pro Tyr Arg Asp Lys Ile Thr Ile
735                 740                 745

GCA ATT CTT CAG CTG CAA GAG GAA GGC AAA CTG CAT ATG ATG AAG GAG     2521
Ala Ile Leu Gln Leu Gln Glu Glu Gly Lys Leu His Met Met Lys Glu
750                 755                 760                 765

AAA TGG TGG AGG GGC AAT GGT TGC CCA GAA GAG GAA AGC AAA GAG GCC     2569
Lys Trp Trp Arg Gly Asn Gly Cys Pro Glu Glu Glu Ser Lys Glu Ala
                770                 775                 780

AGT GCC CTG GGG GTT CAG AAT ATT GGT GGC ATC TTC ATT GTT CTG GCA     2617
Ser Ala Leu Gly Val Gln Asn Ile Gly Gly Ile Phe Ile Val Leu Ala
                785                 790                 795

GCC GGC TTG GTG CTT TCA GTT TTT GTG GCA GTG GGA GAA TTT TTA TAC     2665
Ala Gly Leu Val Leu Ser Val Phe Val Ala Val Gly Glu Phe Leu Tyr
            800                 805                 810

AAA TCC AAA AAA AAC GCT CAA TTG GAA AAG AGG TCC TTC TGT AGT GCC     2713
Lys Ser Lys Lys Asn Ala Gln Leu Glu Lys Arg Ser Phe Cys Ser Ala
815                 820                 825

ATG GTA GAA GAA TTG AGG ATG TCC CTG AAG TGC CAG CGT CGG TTA AAA     2761
Met Val Glu Glu Leu Arg Met Ser Leu Lys Cys Gln Arg Arg Leu Lys
830                 835                 840                 845

CAT AAG CCA CAG GCC CCA GTT ATT GTG AAA ACA GAA GAA GTT ATC AAC     2809
His Lys Pro Gln Ala Pro Val Ile Val Lys Thr Glu Glu Val Ile Asn
                850                 855                 860
```

```
ATG CAC ACA TTT AAC GAC AGA AGG TTG CCA GGT AAA GAA ACC ATG GCA        2857
Met His Thr Phe Asn Asp Arg Arg Leu Pro Gly Lys Glu Thr Met Ala
        865                 870                 875

TAAAGCTGGG AGGCGGAATT C                                                 2878
```

(2) INFORMATION FOR SEQ ID NO:6:

(i) SEQUENCE CHARACTERISTICS:
        (A) LENGTH: 908 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Ile Ile Phe Pro Ile Leu Ser Asn Pro Val Phe Arg Arg Thr
-31 -30                 -25                 -20

Val Lys Leu Leu Leu Cys Leu Leu Trp Ile Gly Tyr Ser Gln Gly Thr
-15                 -10                  -5                   1

Thr His Val Leu Arg Phe Gly Gly Ile Phe Glu Tyr Val Glu Ser Gly
                  5                  10                  15

Pro Met Gly Ala Glu Glu Leu Ala Phe Arg Phe Ala Val Asn Thr Ile
             20                  25                  30

Asn Arg Asn Arg Thr Leu Leu Pro Asn Thr Thr Leu Thr Tyr Asp Thr
         35                  40                  45

Gln Lys Ile Asn Leu Tyr Asp Ser Phe Glu Ala Ser Lys Lys Ala Cys
 50                  55                  60                  65

Asp Gln Leu Ser Leu Gly Val Ala Ala Ile Phe Gly Pro Ser His Ser
                  70                  75                  80

Ser Ser Ala Asn Ala Val Gln Ser Ile Cys Asn Ala Leu Gly Val Pro
             85                  90                  95

His Ile Gln Thr Arg Trp Lys His Gln Val Ser Asp Asn Lys Asp Ser
            100                 105                 110

Phe Tyr Val Ser Leu Tyr Pro Asp Phe Ser Ser Leu Ser Arg Ala Ile
            115                 120                 125

Leu Asp Leu Val Gln Phe Phe Lys Trp Lys Thr Val Thr Val Val Tyr
130                 135                 140                 145

Asp Asp Ser Thr Gly Leu Ile Arg Leu Gln Glu Leu Ile Lys Ala Pro
                150                 155                 160

Ser Arg Tyr Asn Leu Arg Leu Lys Ile Arg Gln Leu Pro Ala Asp Thr
                165                 170                 175

Lys Asp Ala Lys Pro Leu Leu Lys Glu Met Lys Arg Gly Lys Glu Phe
            180                 185                 190

His Val Ile Phe Asp Cys Ser His Glu Met Ala Ala Gly Ile Leu Lys
            195                 200                 205

Gln Ala Leu Ala Met Gly Met Met Thr Glu Tyr Tyr His Tyr Ile Phe
210                 215                 220                 225

Thr Thr Leu Asp Leu Phe Ala Leu Asp Val Glu Pro Tyr Arg Tyr Ser
                230                 235                 240

Gly Val Asn Met Thr Gly Phe Arg Ile Leu Asn Thr Glu Asn Thr Gln
                245                 250                 255

Val Ser Ser Ile Ile Glu Lys Trp Ser Met Glu Arg Leu Gln Ala Pro
            260                 265                 270

Pro Lys Pro Asp Ser Gly Leu Leu Asp Gly Phe Met Thr Thr Asp Ala
            275                 280                 285
```

```
Ala Leu Met Tyr Asp Ala Val His Val Val Ser Val Ala Val Gln Gln
290                 295                 300                 305

Phe Pro Gln Met Thr Val Ser Ser Leu Gln Cys Asn Arg His Lys Pro
            310                 315                 320

Trp Arg Phe Gly Thr Arg Phe Met Ser Leu Ile Lys Glu Ala His Trp
                325                 330                 335

Glu Gly Leu Thr Gly Arg Ile Thr Phe Asn Lys Thr Asn Gly Leu Arg
            340                 345                 350

Thr Asp Phe Asp Leu Asp Val Ile Ser Leu Lys Glu Glu Gly Leu Glu
        355                 360                 365

Lys Ile Gly Thr Trp Asp Pro Ala Ser Gly Leu Asn Met Thr Glu Ser
370                 375                 380                 385

Gln Lys Gly Lys Pro Ala Asn Ile Thr Asp Ser Leu Ser Asn Arg Ser
                390                 395                 400

Leu Ile Val Thr Thr Ile Leu Glu Glu Pro Tyr Val Leu Phe Lys Lys
            405                 410                 415

Ser Asp Lys Pro Leu Tyr Gly Asn Asp Arg Phe Glu Gly Tyr Cys Ile
        420                 425                 430

Asp Leu Leu Arg Glu Leu Ser Thr Ile Leu Gly Phe Thr Tyr Glu Ile
        435                 440                 445

Arg Leu Val Glu Asp Gly Lys Tyr Gly Ala Gln Asp Asp Ala Asn Gly
450                 455                 460                 465

Gln Trp Asn Gly Met Val Arg Glu Leu Ile Asp His Lys Ala Asp Leu
                470                 475                 480

Ala Val Ala Pro Leu Ala Ile Thr Tyr Val Arg Glu Lys Val Ile Asp
            485                 490                 495

Phe Ser Lys Pro Phe Met Thr Leu Gly Ile Ser Ile Leu Tyr Arg Lys
        500                 505                 510

Pro Asn Gly Thr Asn Pro Gly Val Phe Ser Phe Leu Asn Pro Leu Ser
        515                 520                 525

Pro Asp Ile Trp Met Tyr Ile Leu Leu Ala Tyr Leu Gly Val Ser Cys
530                 535                 540                 545

Val Leu Phe Val Ile Ala Arg Phe Ser Pro Tyr Glu Trp Tyr Asn Pro
                550                 555                 560

His Pro Cys Asn Pro Asp Ser Asp Val Val Glu Asn Asn Phe Thr Leu
            565                 570                 575

Leu Asn Ser Phe Trp Phe Gly Val Gly Ala Leu Met Gln Gln Gly Ser
        580                 585                 590

Glu Leu Met Pro Lys Ala Leu Ser Thr Arg Ile Val Gly Gly Ile Trp
        595                 600                 605

Trp Phe Phe Thr Leu Ile Ile Ile Ser Ser Tyr Thr Ala Asn Leu Ala
610                 615                 620                 625

Ala Phe Leu Thr Val Glu Arg Met Glu Ser Pro Ile Asp Ser Ala Asp
                630                 635                 640

Asp Leu Ala Lys Gln Thr Lys Ile Glu Tyr Gly Ala Val Glu Asp Gly
            645                 650                 655

Ala Thr Met Thr Phe Phe Lys Lys Ser Lys Ile Ser Thr Tyr Asp Lys
        660                 665                 670

Met Trp Ala Phe Met Ser Ser Arg Arg Gln Ser Val Leu Val Lys Ser
        675                 680                 685

Asn Glu Glu Gly Ile Gln Arg Val Leu Thr Ser Asp Tyr Ala Phe Leu
690                 695                 700                 705
```

```
Met Glu Ser Thr Thr Ile Glu Phe Val Thr Gln Arg Asn Cys Asn Leu
                710                 715                 720
Thr Gln Ile Gly Gly Leu Ile Asp Ser Lys Gly Tyr Gly Val Gly Thr
            725                 730                 735
Pro Met Gly Ser Pro Tyr Arg Asp Lys Ile Thr Ile Ala Ile Leu Gln
        740                 745                 750
Leu Gln Glu Glu Gly Lys Leu His Met Met Lys Glu Lys Trp Trp Arg
    755                 760                 765
Gly Asn Gly Cys Pro Glu Glu Ser Lys Glu Ala Ser Ala Leu Gly
770                 775                 780                 785
Val Gln Asn Ile Gly Gly Ile Phe Ile Val Leu Ala Ala Gly Leu Val
            790                 795                 800
Leu Ser Val Phe Val Ala Val Gly Glu Phe Leu Tyr Lys Ser Lys Lys
        805                 810                 815
Asn Ala Gln Leu Glu Lys Arg Ser Phe Cys Ser Ala Met Val Glu Glu
    820                 825                 830
Leu Arg Met Ser Leu Lys Cys Gln Arg Arg Leu Lys His Lys Pro Gln
835                 840                 845
Ala Pro Val Ile Val Lys Thr Glu Glu Val Ile Asn Met His Thr Phe
850                 855                 860                 865
Asn Asp Arg Arg Leu Pro Gly Lys Glu Thr Met Ala
            870                 875
```

(2) INFORMATION FOR SEQ ID NO:7:

(i) SEQUENCE CHARACTERISTICS:
        (A) LENGTH: 3407 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 315..2966

(ix) FEATURE:
        (A) NAME/KEY: sig_peptide
        (B) LOCATION: 315..374

(ix) FEATURE:
        (A) NAME/KEY: mat_peptide
        (B) LOCATION: 375..2966

(xi) SEQUENCE DESCRIPTION: SEQ ID NO:7:

```
GAATTCCGTG AGTGCATGGG AGGGTGCTGA ATATTCCGAG ACACTGGGAC CACAGCGGCA      60

GCTCCGCTGA AAACTGCATT CAGCCAGTCC TCCGGACTTC TGGAGCGGGG ACAGGGCGCA     120

GGGCATCAGC AGCCACCAGC AGGACCTGGG AAATAGGGAT TCTTCTGCCT CCACTTCAGG     180

TTTTAGCAGC TTGGTGCTAA ATTGCTGTCT CAAAATGCAG AGGATCTAAT TTGCAGAGGA     240

AAACAGCCAA AGAAGGAAGA GGAGGAAAAG GAAAAAAAAA GGGGTATATT GTGGATGCTC     300

TACTTTTCTT GGAA ATG CAA AAG ATT ATG CAT ATT TCT GTC CTC CTT TCT      350
             Met Gln Lys Ile Met His Ile Ser Val Leu Leu Ser
                 -20             -15             -10

CCT GTT TTA TGG GGA CTG ATT TTT GGT GTC TCT TCT AAC AGC ATA CAG       398
Pro Val Leu Trp Gly Leu Ile Phe Gly Val Ser Ser Asn Ser Ile Gln
            -5               1                5

ATA GGG GGG CTA TTT CCT AGG GGC GCC GAT CAA GAA TAC AGT GCA TTT       446
Ile Gly Gly Leu Phe Pro Arg Gly Ala Asp Gln Glu Tyr Ser Ala Phe
     10              15              20
```

```
CGA GTA GGG ATG GTT CAG TTT TCC ACT TCG GAG TTC AGA CTG ACA CCC      494
Arg Val Gly Met Val Gln Phe Ser Thr Ser Glu Phe Arg Leu Thr Pro
 25              30                  35                  40

CAC ATC GAC AAT TTG GAG GTG GCA AAC AGC TTC GCA GTC ACT AAT GCT      542
His Ile Asp Asn Leu Glu Val Ala Asn Ser Phe Ala Val Thr Asn Ala
                 45                  50                  55

TTC TGC TCC CAG TTT TCG AGA GGA GTC TAT GCT ATT TTT GGA TTT TAT      590
Phe Cys Ser Gln Phe Ser Arg Gly Val Tyr Ala Ile Phe Gly Phe Tyr
             60                  65                  70

GAC AAG AAG TCT GTA AAT ACC ATC ACA TCA TTT TGC GGA ACA CTC CAC      638
Asp Lys Lys Ser Val Asn Thr Ile Thr Ser Phe Cys Gly Thr Leu His
         75                  80                  85

GTC TCC TTC ATC ACT CCC AGC TTC CCA ACA GAT GGC ACA CAT CCA TTT      686
Val Ser Phe Ile Thr Pro Ser Phe Pro Thr Asp Gly Thr His Pro Phe
     90                  95                 100

GTC ATT CAG ATG AGA CCC GAC CTC AAA GGA GCT CTC CTT AGC TTG ATT      734
Val Ile Gln Met Arg Pro Asp Leu Lys Gly Ala Leu Leu Ser Leu Ile
105                 110                 115                 120

GAA TAC TAT CAA TGG GAC AAG TTT GCA TAC CTC TAT GAC AGT GAC AGA      782
Glu Tyr Tyr Gln Trp Asp Lys Phe Ala Tyr Leu Tyr Asp Ser Asp Arg
                125                 130                 135

GGC TTA TCA ACA CTG CAA GCT GTG CTG GAT TCT GCT GCT GAA AAG AAA      830
Gly Leu Ser Thr Leu Gln Ala Val Leu Asp Ser Ala Ala Glu Lys Lys
            140                 145                 150

TGG CAA GTG ACT GCT ATC AAT GTG GGA AAC ATT AAC AAT GAC AAG AAA      878
Trp Gln Val Thr Ala Ile Asn Val Gly Asn Ile Asn Asn Asp Lys Lys
        155                 160                 165

GAT GAG ATG TAC CGA TCA CTT TTT CAA GAT CTG GAG TTA AAA AAG GAA      926
Asp Glu Met Tyr Arg Ser Leu Phe Gln Asp Leu Glu Leu Lys Lys Glu
    170                 175                 180

CGG CGT GTA ATT CTG GAC TGT GAA AGG GAT AAA GTA AAC GAC ATT GTA      974
Arg Arg Val Ile Leu Asp Cys Glu Arg Asp Lys Val Asn Asp Ile Val
185                 190                 195                 200

GAC CAG GTT ATT ACC ATT GGA AAA CAC GTT AAA GGG TAC CAC TAC ATC     1022
Asp Gln Val Ile Thr Ile Gly Lys His Val Lys Gly Tyr His Tyr Ile
                205                 210                 215

ATT GCA AAT CTG GGA TTT ACT GAT GGA GAC CTA TTA AAA ATC CAG TTT     1070
Ile Ala Asn Leu Gly Phe Thr Asp Gly Asp Leu Leu Lys Ile Gln Phe
            220                 225                 230

GGA GGT GCA AAT GTC TCT GGA TTT CAG ATA GTG GAC TAT GAT GAT TCG     1118
Gly Gly Ala Asn Val Ser Gly Phe Gln Ile Val Asp Tyr Asp Asp Ser
        235                 240                 245

TTG GTA TCT AAA TTT ATA GAA AGA TGG TCA ACA CTG GAA GAA AAA GAA     1166
Leu Val Ser Lys Phe Ile Glu Arg Trp Ser Thr Leu Glu Glu Lys Glu
    250                 255                 260

TAC CCT GGA GCT CAC ACA ACA ACA ATT AAG TAT ACT TCT GCT CTG ACC     1214
Tyr Pro Gly Ala His Thr Thr Thr Ile Lys Tyr Thr Ser Ala Leu Thr
265                 270                 275                 280

TAT GAT GCC GTT CAA GTG ATG ACT GAA GCC TTC CGC AAC CTA AGG AAG     1262
Tyr Asp Ala Val Gln Val Met Thr Glu Ala Phe Arg Asn Leu Arg Lys
                285                 290                 295

CAA AGA ATT GAA ATC TCC CGA AGG GGG AAT GCA GGA GAC TGT CTG GCA     1310
Gln Arg Ile Glu Ile Ser Arg Arg Gly Asn Ala Gly Asp Cys Leu Ala
            300                 305                 310

AAC CCA GCA GTG CCC TGG GGA CAA GGT GTA GAA ATA GAA AGG GCC CTC     1358
Asn Pro Ala Val Pro Trp Gly Gln Gly Val Glu Ile Glu Arg Ala Leu
        315                 320                 325

AAA CAG GTT CAG GTT GAA GGT CTC TCA GGA AAT ATA AAG TTT GAC CAG     1406
Lys Gln Val Gln Val Glu Gly Leu Ser Gly Asn Ile Lys Phe Asp Gln
    330                 335                 340
```

-continued

| | | |
|---|---|---|
| AAT GGA AAA AGA ATA AAC TAT ACA ATT AAC ATC ATG GAG CTC AAA ACT<br>Asn Gly Lys Arg Ile Asn Tyr Thr Ile Asn Ile Met Glu Leu Lys Thr<br>345                    350                    355                    360 | 1454 |
| AAT GGG CCC CGG AAG ATT GGC TAC TGG AGT GAA GTG GAC AAA ATG GTT<br>Asn Gly Pro Arg Lys Ile Gly Tyr Trp Ser Glu Val Asp Lys Met Val<br>                    365                    370                    375 | 1502 |
| GTT ACC CTT ACT GAG CTC CCT TCT GGA AAT GAC ACC TCT GGG CTT GAG<br>Val Thr Leu Thr Glu Leu Pro Ser Gly Asn Asp Thr Ser Gly Leu Glu<br>        380                    385                    390 | 1550 |
| AAT AAG ACT GTT GTT GTC ACC ACA ATT TTG GAA TCT CCG TAT GTT ATG<br>Asn Lys Thr Val Val Val Thr Thr Ile Leu Glu Ser Pro Tyr Val Met<br>        395                    400                    405 | 1598 |
| ATG AAG AAA AAT CAT GAA ATG CTT GAA GGC AAT GAG CGC TAT GAG GGC<br>Met Lys Lys Asn His Glu Met Leu Glu Gly Asn Glu Arg Tyr Glu Gly<br>410                    415                    420 | 1646 |
| TAC TGT GTT GAC CTG GCT GCA GAA ATC GCC AAA CAT TGT GGG TTC AAG<br>Tyr Cys Val Asp Leu Ala Ala Glu Ile Ala Lys His Cys Gly Phe Lys<br>425                    430                    435                    440 | 1694 |
| TAC AAG TTG ACA ATT GTT GGT GAT GGC AAG TAT GGG GCC AGG GAT GCA<br>Tyr Lys Leu Thr Ile Val Gly Asp Gly Lys Tyr Gly Ala Arg Asp Ala<br>                    445                    450                    455 | 1742 |
| GAC ACG AAA ATT TGG AAT GGG ATG GTT GGA GAA CTT GTA TAT GGG AAA<br>Asp Thr Lys Ile Trp Asn Gly Met Val Gly Glu Leu Val Tyr Gly Lys<br>                460                    465                    470 | 1790 |
| GCT GAT ATT GCA ATT GCT CCA TTA ACT ATT ACC CTT GTG AGA GAA GAG<br>Ala Asp Ile Ala Ile Ala Pro Leu Thr Ile Thr Leu Val Arg Glu Glu<br>475                      480                    485 | 1838 |
| GTG ATT GAC TTC TCA AAG CCC TTC ATG AGC CTC GGG ATA TCT ATC ATG<br>Val Ile Asp Phe Ser Lys Pro Phe Met Ser Leu Gly Ile Ser Ile Met<br>490                    495                    500 | 1886 |
| ATC AAG AAG CCT CAG AAG TCC AAA CCA GGA GTG TTT TCC TTT CTT GAT<br>Ile Lys Lys Pro Gln Lys Ser Lys Pro Gly Val Phe Ser Phe Leu Asp<br>505                    510                    515                    520 | 1934 |
| CCT TTA GCC TAT GAG ATC TGG ATG TGC ATT GTT TTT GCC TAC ATT GGG<br>Pro Leu Ala Tyr Glu Ile Trp Met Cys Ile Val Phe Ala Tyr Ile Gly<br>                    525                    530                    535 | 1982 |
| GTC AGT GTA GTT TTA TTC CTG GTC AGC AGA TTT AGC CCC TAC GAG TGG<br>Val Ser Val Val Leu Phe Leu Val Ser Arg Phe Ser Pro Tyr Glu Trp<br>                540                    545                    550 | 2030 |
| CAC ACT GAG GAG TTT GAA GAT GGA AGA GAA ACA CAA AGT AGT GAA TCA<br>His Thr Glu Glu Phe Glu Asp Gly Arg Glu Thr Gln Ser Ser Glu Ser<br>        555                    560                    565 | 2078 |
| ACT AAT GAA TTT GGG ATT TTT AAT AGT CTC TGG TTT TCC TTG GGT GCC<br>Thr Asn Glu Phe Gly Ile Phe Asn Ser Leu Trp Phe Ser Leu Gly Ala<br>        570                    575                    580 | 2126 |
| TTT ATG CGG CAA GGA TGC GAT ATT TCG CCA AGA TCC CTC TCT GGG CGC<br>Phe Met Arg Gln Gly Cys Asp Ile Ser Pro Arg Ser Leu Ser Gly Arg<br>585                    590                    595                    600 | 2174 |
| ATT GTT GGA GGT GTG TGG TGG TTC TTT ACC CTG ATC ATA ATC TCC TCC<br>Ile Val Gly Gly Val Trp Trp Phe Phe Thr Leu Ile Ile Ile Ser Ser<br>                    605                    610                    615 | 2222 |
| TAC ACG GCT AAC TTA GCT GCC TTC CTG ACT GTA GAG AGG ATG GTG TCT<br>Tyr Thr Ala Asn Leu Ala Ala Phe Leu Thr Val Glu Arg Met Val Ser<br>        620                    625                    630 | 2270 |
| CCC ATC GAA AGT GCT GAG GAT CTT TCT AAG CAA ACA GAA ATT GCT TAT<br>Pro Ile Glu Ser Ala Glu Asp Leu Ser Lys Gln Thr Glu Ile Ala Tyr<br>        635                    640                    645 | 2318 |
| GGA ACA TTA GAC TCT GGC TCC ACT AAA GAG TTT TTC AGG AGA TCT AAA<br>Gly Thr Leu Asp Ser Gly Ser Thr Lys Glu Phe Phe Arg Arg Ser Lys<br>650                    655                    660 | 2366 |

```
ATT GCA GTG TTT GAT AAA ATG TGG ACC TAC ATG CGG AGT GCG GAG CCC      2414
Ile Ala Val Phe Asp Lys Met Trp Thr Tyr Met Arg Ser Ala Glu Pro
665                 670                 675                 680

TCT GTG TTT GTG AGG ACT ACG GCC GAA GGG GTG GCT AGA GTG CGG AAG      2462
Ser Val Phe Val Arg Thr Thr Ala Glu Gly Val Ala Arg Val Arg Lys
                685                 690                 695

TCC AAA GGG AAA TAT GCC TAC TTG TTG GAG TCC ACG ATG AAC GAG TAC      2510
Ser Lys Gly Lys Tyr Ala Tyr Leu Leu Glu Ser Thr Met Asn Glu Tyr
            700                 705                 710

ATT GAG CAA AGG AAG CCT TGC GAC ACC ATG AAA GTT GGT GGA AAC CTG      2558
Ile Glu Gln Arg Lys Pro Cys Asp Thr Met Lys Val Gly Gly Asn Leu
        715                 720                 725

GAT TCC AAA GGC TAT GGC ATC GCA ACA CCT AAA GGA TCC TCA TTA GGA      2606
Asp Ser Lys Gly Tyr Gly Ile Ala Thr Pro Lys Gly Ser Ser Leu Gly
    730                 735                 740

ACC CCA GTA AAT CTT GCA GTA TTG AAA CTC AGT GAG CAA GGC GTC TTA      2654
Thr Pro Val Asn Leu Ala Val Leu Lys Leu Ser Glu Gln Gly Val Leu
745                 750                 755                 760

GAC AAG CTG AAA AAC AAA TGG TGG TAC GAT AAA GGT GAA TGT GGA GCC      2702
Asp Lys Leu Lys Asn Lys Trp Trp Tyr Asp Lys Gly Glu Cys Gly Ala
                765                 770                 775

AAG GAC TCT GGA AGT AAG GAA AAG ACC AGT GCC CTC AGT CTG AGC AAC      2750
Lys Asp Ser Gly Ser Lys Glu Lys Thr Ser Ala Leu Ser Leu Ser Asn
            780                 785                 790

GTT GCT GGA GTA TTC TAC ATC CTT GTC GGG GGC CTT GGT TTG GCA ATG      2798
Val Ala Gly Val Phe Tyr Ile Leu Val Gly Gly Leu Gly Leu Ala Met
        795                 800                 805

CTG GTG GCT TTG ATT GAG TTC TGT TAC AAG TCA AGG GCC GAG GCG AAA      2846
Leu Val Ala Leu Ile Glu Phe Cys Tyr Lys Ser Arg Ala Glu Ala Lys
    810                 815                 820

CGA ATG AAG GTG GCA AAG AAT GCA CAG AAT ATT AAC CCA TCT TCC TCG      2894
Arg Met Lys Val Ala Lys Asn Ala Gln Asn Ile Asn Pro Ser Ser Ser
825                 830                 835                 840

CAG AAT TCA CAG AAT TTT GCA ACT TAT AAG GAA GGT TAC AAC GTA TAT      2942
Gln Asn Ser Gln Asn Phe Ala Thr Tyr Lys Glu Gly Tyr Asn Val Tyr
                845                 850                 855

GGC ATC GAA AGT GTT AAA ATT TAGGGGATGA CCTTGAATGA TGCCATGAGG         2993
Gly Ile Glu Ser Val Lys Ile
            860

AACAAGGCAA GGCTGTCAAT TACAGGAAGT ACTGGAGAAA ATGGACGTGT TATGACTCCA    3053

GAATTTCCCA AAGCNGTGCA TGCTGTCCCT TACGTGAGTC CTGGCATGGG AATGAATGTC    3113

AGTGTGACTG ATCTCTCGTG ATTGATAAGA ACCTTTTGAG TGCCTTACAC AATGGTTTTC    3173

TTGTGTGTTT ATTGTCAAAG TGGTGAGAGG CATCCAGTAT CTTGAAGACT TTTCTTTCAG    3233

CCAAGAATTC TTAAATATGT GGAGTTCATC TTGAATTGTA AGGAATGATT AATTAAAACA    3293

CAACATCTTT TTCTACTCGA GTTACAGACA AAGCGTGGTG GACATGCACA GCTAACATGG    3353

AAGTACTATA ATTTACCTGA AGTCTTTGTA CAGACAACAA ACCTGTTTCT GCAG          3407
```

(2) INFORMATION FOR SEQ ID NO:8:

(i) SEQUENCE CHARACTERISTICS:
        (A) LENGTH: 883 amino acids
        (B) TYPE: amino acid
        (D) TOPOLOGY: linear (ii) MOLECULE TYPE: protein -continued (xi) SEQUENCE DESCRIPTION: SEQ ID NO:8:

```
Met Gln Lys Ile Met His Ile Ser Val Leu Leu Ser Pro Val Leu Trp
-20             -15                 -10                 -5

Gly Leu Ile Phe Gly Val Ser Ser Asn Ser Ile Gln Ile Gly Gly Leu
                1               5                   10

Phe Pro Arg Gly Ala Asp Gln Glu Tyr Ser Ala Phe Arg Val Gly Met
        15                  20                  25

Val Gln Phe Ser Thr Ser Glu Phe Arg Leu Thr Pro His Ile Asp Asn
    30                  35                  40

Leu Glu Val Ala Asn Ser Phe Ala Val Thr Asn Ala Phe Cys Ser Gln
45                  50                  55                  60

Phe Ser Arg Gly Val Tyr Ala Ile Phe Gly Phe Tyr Asp Lys Lys Ser
                65                  70                  75

Val Asn Thr Ile Thr Ser Phe Cys Gly Thr Leu His Val Ser Phe Ile
            80                  85                  90

Thr Pro Ser Phe Pro Thr Asp Gly Thr His Pro Phe Val Ile Gln Met
        95                  100                 105

Arg Pro Asp Leu Lys Gly Ala Leu Leu Ser Leu Ile Glu Tyr Tyr Gln
    110                 115                 120

Trp Asp Lys Phe Ala Tyr Leu Tyr Asp Ser Asp Arg Gly Leu Ser Thr
125                 130                 135                 140

Leu Gln Ala Val Leu Asp Ser Ala Ala Glu Lys Lys Trp Gln Val Thr
                145                 150                 155

Ala Ile Asn Val Gly Asn Ile Asn Asn Asp Lys Lys Asp Glu Met Tyr
            160                 165                 170

Arg Ser Leu Phe Gln Asp Leu Glu Leu Lys Lys Glu Arg Arg Val Ile
        175                 180                 185

Leu Asp Cys Glu Arg Asp Lys Val Asn Asp Ile Val Asp Gln Val Ile
    190                 195                 200

Thr Ile Gly Lys His Val Lys Gly Tyr His Tyr Ile Ile Ala Asn Leu
205                 210                 215                 220

Gly Phe Thr Asp Gly Asp Leu Leu Lys Ile Gln Phe Gly Gly Ala Asn
                225                 230                 235

Val Ser Gly Phe Gln Ile Val Asp Tyr Asp Asp Ser Leu Val Ser Lys
            240                 245                 250

Phe Ile Glu Arg Trp Ser Thr Leu Glu Glu Lys Glu Tyr Pro Gly Ala
        255                 260                 265

His Thr Thr Thr Ile Lys Tyr Thr Ser Ala Leu Thr Tyr Asp Ala Val
    270                 275                 280

Gln Val Met Thr Glu Ala Phe Arg Asn Leu Arg Lys Gln Arg Ile Glu
285                 290                 295                 300

Ile Ser Arg Arg Gly Asn Ala Gly Asp Cys Leu Ala Asn Pro Ala Val
                305                 310                 315

Pro Trp Gly Gln Gly Val Glu Ile Glu Arg Ala Leu Lys Gln Val Gln
            320                 325                 330

Val Glu Gly Leu Ser Gly Asn Ile Lys Phe Asp Gln Asn Gly Lys Arg
        335                 340                 345

Ile Asn Tyr Thr Ile Asn Ile Met Glu Leu Lys Thr Asn Gly Pro Arg
    350                 355                 360

Lys Ile Gly Tyr Trp Ser Glu Val Asp Lys Met Val Val Thr Leu Thr
365                 370                 375                 380

Glu Leu Pro Ser Gly Asn Asp Thr Ser Gly Leu Glu Asn Lys Thr Val
                385                 390                 395
```

-continued

```
Val Val Thr Thr Ile Leu Glu Ser Pro Tyr Val Met Met Lys Lys Asn
            400                 405                 410

His Glu Met Leu Glu Gly Asn Glu Arg Tyr Glu Gly Tyr Cys Val Asp
            415                 420                 425

Leu Ala Ala Glu Ile Ala Lys His Cys Gly Phe Lys Tyr Lys Leu Thr
            430                 435                 440

Ile Val Gly Asp Gly Lys Tyr Gly Ala Arg Asp Ala Asp Thr Lys Ile
445                 450                 455                 460

Trp Asn Gly Met Val Gly Glu Leu Val Tyr Gly Lys Ala Asp Ile Ala
                    465                 470                 475

Ile Ala Pro Leu Thr Ile Thr Leu Val Arg Glu Glu Val Ile Asp Phe
            480                 485                 490

Ser Lys Pro Phe Met Ser Leu Gly Ile Ser Ile Met Ile Lys Lys Pro
            495                 500                 505

Gln Lys Ser Lys Pro Gly Val Phe Ser Phe Leu Asp Pro Leu Ala Tyr
            510                 515                 520

Glu Ile Trp Met Cys Ile Val Phe Ala Tyr Ile Gly Val Ser Val Val
525                 530                 535                 540

Leu Phe Leu Val Ser Arg Phe Ser Pro Tyr Glu Trp His Thr Glu Glu
                    545                 550                 555

Phe Glu Asp Gly Arg Glu Thr Gln Ser Ser Glu Ser Thr Asn Glu Phe
                    560                 565                 570

Gly Ile Phe Asn Ser Leu Trp Phe Ser Leu Gly Ala Phe Met Arg Gln
            575                 580                 585

Gly Cys Asp Ile Ser Pro Arg Ser Leu Ser Gly Arg Ile Val Gly Gly
            590                 595                 600

Val Trp Trp Phe Phe Thr Leu Ile Ile Ile Ser Ser Tyr Thr Ala Asn
605                 610                 615                 620

Leu Ala Ala Phe Leu Thr Val Glu Arg Met Val Ser Pro Ile Glu Ser
                    625                 630                 635

Ala Glu Asp Leu Ser Lys Gln Thr Glu Ile Ala Tyr Gly Thr Leu Asp
                    640                 645                 650

Ser Gly Ser Thr Lys Glu Phe Phe Arg Arg Ser Lys Ile Ala Val Phe
            655                 660                 665

Asp Lys Met Trp Thr Tyr Met Arg Ser Ala Glu Pro Ser Val Phe Val
670                 675                 680

Arg Thr Thr Ala Glu Gly Val Ala Arg Val Arg Lys Ser Lys Gly Lys
685                 690                 695                 700

Tyr Ala Tyr Leu Leu Glu Ser Thr Met Asn Glu Tyr Ile Glu Gln Arg
                    705                 710                 715

Lys Pro Cys Asp Thr Met Lys Val Gly Gly Asn Leu Asp Ser Lys Gly
            720                 725                 730

Tyr Gly Ile Ala Thr Pro Lys Gly Ser Ser Leu Gly Thr Pro Val Asn
            735                 740                 745

Leu Ala Val Leu Lys Leu Ser Glu Gln Gly Val Leu Asp Lys Leu Lys
            750                 755                 760

Asn Lys Trp Trp Tyr Asp Lys Gly Glu Cys Gly Ala Lys Asp Ser Gly
765                 770                 775                 780

Ser Lys Glu Lys Thr Ser Ala Leu Ser Leu Ser Asn Val Ala Gly Val
                    785                 790                 795

Phe Tyr Ile Leu Val Gly Gly Leu Gly Leu Ala Met Leu Val Ala Leu
            800                 805                 810
```

```
Ile Glu Phe Cys Tyr Lys Ser Arg Ala Glu Ala Lys Arg Met Lys Val
        815                 820                 825

Ala Lys Asn Ala Gln Asn Ile Asn Pro Ser Ser Gln Asn Ser Gln
    830                 835                 840

Asn Phe Ala Thr Tyr Lys Glu Gly Tyr Asn Val Tyr Gly Ile Glu Ser
845                 850                 855                 860

Val Lys Ile (2) INFORMATION FOR SEQ ID NO:9:

(i) SEQUENCE CHARACTERISTICS:
        (A) LENGTH: 3385 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 418..3132

(ix) FEATURE:
        (A) NAME/KEY: mat_peptide
        (B) LOCATION: 508..3132

(ix) FEATURE:
        (A) NAME/KEY: sig_peptide
        (B) LOCATION: 418..507

(xi) SEQUENCE DESCRIPTION: SEQ ID NO:9:

GAATTCCGTC TTCTTTCCCC CTTTTCCCTC CTCTGTCTGT GCCTATCCCC CGACTTTTGC      60

ATCTGACCAA AGGACGAATG AGGGAGACGT TCCTGCAGAT CGGGGCAGCA ACTTTCCTCA     120

GCTGGTCTCT GGGCTCCGGA GCCAGAGAGC GCTGATCCTC CGCGTCTGCG GCCCATGAAG     180

AGAGAGAGAG CCGTGATGGG CTAGCGACAG CACTGAGGAG CCCCGAGAGA GCTCAGCCTT     240

GCCAGCCAGC TCCGCGGTCC CACGCGGGTT CCCTCGAGCT CGCTCCGTGG GGAGCGCGCA     300

GCGTGCTTGG AACCGGAGCA TCCAGAGAGG ATGAGGCGGG GACCCGGCCC AAGTTGGGTG     360

CATCTCTCGG GCGTCCGGCA GCGGCTGTAT CTCGGCATGA ATTAAGAAGC TAGGAAG       417

ATG GAG CAC GGC ACA CTC CTC GCC CAG CCC GGG CTC TGG ACC AGG GAC      465
Met Glu His Gly Thr Leu Leu Ala Gln Pro Gly Leu Trp Thr Arg Asp
-30             -25                 -20                 -15

ACC AGC TGG GCA CTC CTC TAT TTC CTC TGC TAT ATC CTC CCT CAG ACC      513
Thr Ser Trp Ala Leu Leu Tyr Phe Leu Cys Tyr Ile Leu Pro Gln Thr
            -10                 -5                   1

GCC CCG CAA GTA CTC AGG ATC GGA GGG ATT TTT GAA ACA GTG GAA AAT      561
Ala Pro Gln Val Leu Arg Ile Gly Gly Ile Phe Glu Thr Val Glu Asn
                5                   10                  15

GAG CCT GTT AAT GTT GAA GAA TTA GCT TTC AAG TTT GCA GTC ACC AGC      609
Glu Pro Val Asn Val Glu Glu Leu Ala Phe Lys Phe Ala Val Thr Ser
        20                  25                  30

ATT AAC AGA AAC CGA ACC CTG ATG CCT AAC ACC ACA TTA ACC TAT GAC      657
Ile Asn Arg Asn Arg Thr Leu Met Pro Asn Thr Thr Leu Thr Tyr Asp
 35                  40                  45                  50

ATC CAG AGA ATT AAC CTT TTT GAT AGT TTT GAA GCC TCG CGG AGA GCA      705
Ile Gln Arg Ile Asn Leu Phe Asp Ser Phe Glu Ala Ser Arg Arg Ala
                 55                  60                  65

TGT GAC CAG CTG GCT CTT GGT GTG GCT GCT CTC TTT GGC CCT TCC CAT      753
Cys Asp Gln Leu Ala Leu Gly Val Ala Ala Leu Phe Gly Pro Ser His
                 70                  75                  80
```

```
AGC TCC TCC GTC AGT GCT GTG CAG TCT ATT TGC AAT GCT CTC GAA GTT      801
Ser Ser Ser Val Ser Ala Val Gln Ser Ile Cys Asn Ala Leu Glu Val
            85                  90                  95

CCA CAC ATA CAG ACC CGC TGG AAA CAC CCC TCG GTG GAC AAC AAA GAT      849
Pro His Ile Gln Thr Arg Trp Lys His Pro Ser Val Asp Asn Lys Asp
100                 105                 110

TTG TTT TAC ATC AAC CTT TAC CCA GAT TAT GCA GCT ATC AGC AGG GCG      897
Leu Phe Tyr Ile Asn Leu Tyr Pro Asp Tyr Ala Ala Ile Ser Arg Ala
115                 120                 125                 130

ATC CTG GAT CTG GTC CTC TAT TAC AAC TGG AAA ACA GTG ACA GTG GTG      945
Ile Leu Asp Leu Val Leu Tyr Tyr Asn Trp Lys Thr Val Thr Val Val
            135                 140                 145

TAT GAA GAC AGC ACA GGT CTA ATT CGT CTA CAA GAG CTC ATC AAA GCT      993
Tyr Glu Asp Ser Thr Gly Leu Ile Arg Leu Gln Glu Leu Ile Lys Ala
                150                 155                 160

CCC TCC AGA TAT AAT ATT AAA ATC AAA ATC CGC CAG CTG CCC TCT GGG     1041
Pro Ser Arg Tyr Asn Ile Lys Ile Lys Ile Arg Gln Leu Pro Ser Gly
            165                 170                 175

AAT AAA GAT GCC AAG CCT TTA CTC AAG GAG ATG AAG AAA GGC AAG GAG     1089
Asn Lys Asp Ala Lys Pro Leu Leu Lys Glu Met Lys Lys Gly Lys Glu
180                 185                 190

TTC TAT GTG ATA TTT GAT TGT TCA CAT GAA ACA GCC GCT GAA ATC CTT     1137
Phe Tyr Val Ile Phe Asp Cys Ser His Glu Thr Ala Ala Glu Ile Leu
195                 200                 205                 210

AAG CAG ATT CTG TTC ATG GGC ATG ATG ACC GAA TAC TAT CAC TAC TTT     1185
Lys Gln Ile Leu Phe Met Gly Met Met Thr Glu Tyr Tyr His Tyr Phe
            215                 220                 225

TTC ACA ACC CTG GAC TTA TTT GCT TTG GAT CTG GAA CTC TAT AGG TAC     1233
Phe Thr Thr Leu Asp Leu Phe Ala Leu Asp Leu Glu Leu Tyr Arg Tyr
                230                 235                 240

AGT GGC GTA AAC ATG ACC GGG TTT GGG CTG CTT AAC ATT GAC AAC CCT     1281
Ser Gly Val Asn Met Thr Gly Phe Gly Leu Leu Asn Ile Asp Asn Pro
            245                 250                 255

CAC GTG TCA TCC ATC ATT GAG AAG TGG TCC ATG GAG AGA CTG CAG GCC     1329
His Val Ser Ser Ile Ile Glu Lys Trp Ser Met Glu Arg Leu Gln Ala
260                 265                 270

CCA CCC AGG CCC GAG ACT GGC CTT TTG GAT GGC ATG ATG ACA ACT GAA     1377
Pro Pro Arg Pro Glu Thr Gly Leu Leu Asp Gly Met Met Thr Thr Glu
275                 280                 285                 290

GCG GCT CTG ATG TAC GAT GCT GTG TAC ATG GTG GCC ATT GCC TCG CAC     1425
Ala Ala Leu Met Tyr Asp Ala Val Tyr Met Val Ala Ile Ala Ser His
            295                 300                 305

CGG GCA TCC CAG CTG ACC GTC AGC TCC CTG CAG TGC CAT AGA CAT AAG     1473
Arg Ala Ser Gln Leu Thr Val Ser Ser Leu Gln Cys His Arg His Lys
                310                 315                 320

CCA TGG CGC CTC GGA CCC AGA TTT ATG AAC CTG ATC AAA GAG GCC CGG     1521
Pro Trp Arg Leu Gly Pro Arg Phe Met Asn Leu Ile Lys Glu Ala Arg
            325                 330                 335

TGG GAT GGC TTG ACT GGG CAT ATC ACC TTT AAT AAA ACC AAT GGC TTG     1569
Trp Asp Gly Leu Thr Gly His Ile Thr Phe Asn Lys Thr Asn Gly Leu
340                 345                 350

AGG AAG GAT TTT GAT CTG GAC ATT ATT AGT CTC AAA GAG GAA GGA ACT     1617
Arg Lys Asp Phe Asp Leu Asp Ile Ile Ser Leu Lys Glu Glu Gly Thr
355                 360                 365                 370

GAA AAG ATT GGG ATT TGG AAT TCC AAC AGT GGG CTT AAC ATG ACG GAC     1665
Glu Lys Ile Gly Ile Trp Asn Ser Asn Ser Gly Leu Asn Met Thr Asp
            375                 380                 385

AGC AAC AAA GAC AAG TCC AGC AAT ATC ACT GAT TCA TTG GCC AAC AGA     1713
Ser Asn Lys Asp Lys Ser Ser Asn Ile Thr Asp Ser Leu Ala Asn Arg
                390                 395                 400
```

```
ACA CTC ATT GTC ACC ACC ATT CTG GAA GAA CCC TAT GTT ATG TAC AGG    1761
Thr Leu Ile Val Thr Thr Ile Leu Glu Glu Pro Tyr Val Met Tyr Arg
            405                 410                 415

AAA TCT GAT AAG CCT CTA TAT GGA AAT GAC AGA TTT GAA GGA TAT TGC    1809
Lys Ser Asp Lys Pro Leu Tyr Gly Asn Asp Arg Phe Glu Gly Tyr Cys
420                 425                 430

CTA GAC CTG TTG AAA GAA TTG TCA AAC ATC CTG GGT TTC ATT TAT GAT    1857
Leu Asp Leu Leu Lys Glu Leu Ser Asn Ile Leu Gly Phe Ile Tyr Asp
435                 440                 445                 450

GTT AAA CTA GTT CCC GAT GGC AAA TAT GGG GCC CAG AAT GAC AAA GGG    1905
Val Lys Leu Val Pro Asp Gly Lys Tyr Gly Ala Gln Asn Asp Lys Gly
            455                 460                 465

GAG TGG AAC GGG ATG GTT AAA GAA CTC ATA GAT CAC AGG GCT GAC CTG    1953
Glu Trp Asn Gly Met Val Lys Glu Leu Ile Asp His Arg Ala Asp Leu
        470                 475                 480

GCA GTG GCT CCT CTT ACC ATC ACC TAC GTG CGG GAG AAA GTC ATT GAC    2001
Ala Val Ala Pro Leu Thr Ile Thr Tyr Val Arg Glu Lys Val Ile Asp
            485                 490                 495

TTC TCC AAA CCC TTC ATG ACC CTA GGC ATC AGC ATT CTC TAC CGG AAG    2049
Phe Ser Lys Pro Phe Met Thr Leu Gly Ile Ser Ile Leu Tyr Arg Lys
500                 505                 510

CCC AAT GGT ACC AAT CCA GGC GTT TTC TCC TTC CTC AAC CCC CTG TCT    2097
Pro Asn Gly Thr Asn Pro Gly Val Phe Ser Phe Leu Asn Pro Leu Ser
515                 520                 525                 530

CCA GAT ATT TGG ATG TAT GTG CTC TTA GCC TGC TTG GGA GTC AGC TGT    2145
Pro Asp Ile Trp Met Tyr Val Leu Leu Ala Cys Leu Gly Val Ser Cys
            535                 540                 545

GTA CTC TTT GTG ATT GCA AGG TTT ACA CCC TAC GAG TGG TAT AAC CCC    2193
Val Leu Phe Val Ile Ala Arg Phe Thr Pro Tyr Glu Trp Tyr Asn Pro
        550                 555                 560

CAC CCA TGC AAC CCT GAC TCA GAC GTG GTG GAA AAC AAT TTT ACT TTA    2241
His Pro Cys Asn Pro Asp Ser Asp Val Val Glu Asn Asn Phe Thr Leu
            565                 570                 575

CTA AAT AGT TTC TGG TTT GGA GTT GGA GCT CTC ATG CGG CAA GGA TCA    2289
Leu Asn Ser Phe Trp Phe Gly Val Gly Ala Leu Met Arg Gln Gly Ser
        580                 585                 590

GAG CTG ATG CCC AAA GCT CTA TCG ACC AGA ATA GTT GGA GGG ATA TGG    2337
Glu Leu Met Pro Lys Ala Leu Ser Thr Arg Ile Val Gly Gly Ile Trp
595                 600                 605                 610

TGG TTT TTC ACC CTA ATC ATC ATT TCA TCC TAC ACG GCC AAT CTG GCT    2385
Trp Phe Phe Thr Leu Ile Ile Ile Ser Ser Tyr Thr Ala Asn Leu Ala
            615                 620                 625

GCC TTC TTG ACA GTA GAG AGA ATG GAA TCC CCC ATA GAT TCG GCA GAT    2433
Ala Phe Leu Thr Val Glu Arg Met Glu Ser Pro Ile Asp Ser Ala Asp
            630                 635                 640

GAT CTG GCA AAG CAA ACC AAG ATA GAA TAT GGG GCG GTT AGA GAT GGA    2481
Asp Leu Ala Lys Gln Thr Lys Ile Glu Tyr Gly Ala Val Arg Asp Gly
            645                 650                 655

TCA ACA ATG ACC TTC TTC AAG AAA TCA AAA ATC TCC ACC TAT GAG AAG    2529
Ser Thr Met Thr Phe Phe Lys Lys Ser Lys Ile Ser Thr Tyr Glu Lys
660                 665                 670

ATG TGG GCT TTC ATG AGC AGC AGG CAG CAG ACC GCC CTG GTA AGA AAC    2577
Met Trp Ala Phe Met Ser Ser Arg Gln Gln Thr Ala Leu Val Arg Asn
675                 680                 685                 690

AGT GAT GAG GGG ATC CAG AGA GTG CTC ACC ACA GAC TAC GCG CTG CTG    2625
Ser Asp Glu Gly Ile Gln Arg Val Leu Thr Thr Asp Tyr Ala Leu Leu
            695                 700                 705

ATG GAG TCC ACC AGC ATT GAG TAT GTG ACG CAG AGA AAC TGC AAC CTC    2673
Met Glu Ser Thr Ser Ile Glu Tyr Val Thr Gln Arg Asn Cys Asn Leu
            710                 715                 720
```

-continued

```
ACT CAG ATC GGG GGC CTC ATT GAC TCC AAA GGT TAC GGA GTG GGA ACA         2721
Thr Gln Ile Gly Gly Leu Ile Asp Ser Lys Gly Tyr Gly Val Gly Thr
        725                 730                 735

CCT ATT GGT TCT CCT TAC CGG GAT AAA ATT ACT ATT GCT ATT CTT CAA         2769
Pro Ile Gly Ser Pro Tyr Arg Asp Lys Ile Thr Ile Ala Ile Leu Gln
        740                 745                 750

CTC CAA GAA GAA GGG AAG CTG CAT ATG ATG AAA GAG AAG TGG TGG CGT         2817
Leu Gln Glu Glu Gly Lys Leu His Met Met Lys Glu Lys Trp Trp Arg
755                 760                 765                 770

GGG AAT GGC TGC CCC GAG GAA GAC AAC AAA GAA GCC AGT GCC CTG GGA         2865
Gly Asn Gly Cys Pro Glu Glu Asp Asn Lys Glu Ala Ser Ala Leu Gly
                775                 780                 785

GTG GAA AAT ATT GGA GGC ATC TTC ATT GTT CTG GCT GCC GGA CTG GTC         2913
Val Glu Asn Ile Gly Gly Ile Phe Ile Val Leu Ala Ala Gly Leu Val
        790                 795                 800

CTT TCT GTA TTT GTA GCT ATT GGA GAA TTC ATA TAC AAA TCA CGG AAG         2961
Leu Ser Val Phe Val Ala Ile Gly Glu Phe Ile Tyr Lys Ser Arg Lys
        805                 810                 815

AAT AAT GAT ATT GAA CAG TGT CTC TCT TTC AAC GCT ATC ATG GAA GAA         3009
Asn Asn Asp Ile Glu Gln Cys Leu Ser Phe Asn Ala Ile Met Glu Glu
        820                 825                 830

CTG GGA ATC TCA CTG AAG AAT CAG AAA AAA ATA AAG AAA AAG TCA AGA         3057
Leu Gly Ile Ser Leu Lys Asn Gln Lys Lys Ile Lys Lys Lys Ser Arg
835                 840                 845                 850

ACT AAG GGG AAA TCT TCC TTC ACA AGT ATC CTT ACT TGT CAT CAG AGA         3105
Thr Lys Gly Lys Ser Ser Phe Thr Ser Ile Leu Thr Cys His Gln Arg
                855                 860                 865

CGA ACT CAG AGA AAA GAG ACT GTG GCG TGATCCAAGG AAACGCCTGT               3152
Arg Thr Gln Arg Lys Glu Thr Val Ala
                870                 875

AGGAAGAAAA AGGATGCATT CCCTACAGAT TTTTGGAGAA AGGATTTCTG AGGAGTTGTG       3212

TGATGTGTTT CCATATATCT ATATCCATAA CTCTGATTAT GAATACAGAT ATAAGAAATA       3272

CAAAAGTTTA AAAAGCTCAC ATAGATATGA CTTGGGAAGT GACACCAGTT CTTTTAAAAT       3332

AAATTTGTAT GCACAAAAAA AAAAAAAAAA AAAAAAAAA AAAAAGGAA TTC                3385
```

(2) INFORMATION FOR SEQ ID NO:10:

(i) SEQUENCE CHARACTERISTICS:
        (A) LENGTH: 905 amino acids
        (B) TYPE: amino acid
        (D) TOPOLOGY: linear (ii) MOLECULE TYPE: protein (xi) SEQUENCE DESCRIPTION: SEQ ID NO:10:

```
Met Glu His Gly Thr Leu Leu Ala Gln Pro Gly Leu Trp Thr Arg Asp
-30                 -25                 -20                 -15

Thr Ser Trp Ala Leu Leu Tyr Phe Leu Cys Tyr Ile Leu Pro Gln Thr
                -10                 -5                  1

Ala Pro Gln Val Leu Arg Ile Gly Gly Ile Phe Glu Thr Val Glu Asn
        5                   10                  15

Glu Pro Val Asn Val Glu Glu Leu Ala Phe Lys Phe Ala Val Thr Ser
        20                  25                  30

Ile Asn Arg Asn Arg Thr Leu Met Pro Asn Thr Thr Leu Thr Tyr Asp
35                  40                  45                  50

Ile Gln Arg Ile Asn Leu Phe Asp Ser Phe Glu Ala Ser Arg Arg Ala
                55                  60                  65
```

-continued

```
Cys Asp Gln Leu Ala Leu Gly Val Ala Ala Leu Phe Gly Pro Ser His
             70                  75                  80
Ser Ser Ser Val Ser Ala Val Gln Ser Ile Cys Asn Ala Leu Glu Val
         85                  90                  95
Pro His Ile Gln Thr Arg Trp Lys His Pro Ser Val Asp Asn Lys Asp
    100                 105                 110
Leu Phe Tyr Ile Asn Leu Tyr Pro Asp Tyr Ala Ala Ile Ser Arg Ala
115                 120                 125                 130
Ile Leu Asp Leu Val Leu Tyr Tyr Asn Trp Lys Thr Val Thr Val Val
                135                 140                 145
Tyr Glu Asp Ser Thr Gly Leu Ile Arg Leu Gln Glu Leu Ile Lys Ala
            150                 155                 160
Pro Ser Arg Tyr Asn Ile Lys Ile Lys Ile Arg Gln Leu Pro Ser Gly
        165                 170                 175
Asn Lys Asp Ala Lys Pro Leu Leu Lys Glu Met Lys Lys Gly Lys Glu
    180                 185                 190
Phe Tyr Val Ile Phe Asp Cys Ser His Glu Thr Ala Ala Glu Ile Leu
195                 200                 205                 210
Lys Gln Ile Leu Phe Met Gly Met Met Thr Glu Tyr Tyr His Tyr Phe
                215                 220                 225
Phe Thr Thr Leu Asp Leu Phe Ala Leu Asp Leu Glu Leu Tyr Arg Tyr
            230                 235                 240
Ser Gly Val Asn Met Thr Gly Phe Gly Leu Leu Asn Ile Asp Asn Pro
        245                 250                 255
His Val Ser Ser Ile Ile Glu Lys Trp Ser Met Glu Arg Leu Gln Ala
    260                 265                 270
Pro Pro Arg Pro Glu Thr Gly Leu Leu Asp Gly Met Met Thr Thr Glu
275                 280                 285                 290
Ala Ala Leu Met Tyr Asp Ala Val Tyr Met Val Ala Ile Ala Ser His
                295                 300                 305
Arg Ala Ser Gln Leu Thr Val Ser Ser Leu Gln Cys His Arg His Lys
            310                 315                 320
Pro Trp Arg Leu Gly Pro Arg Phe Met Asn Leu Ile Lys Glu Ala Arg
        325                 330                 335
Trp Asp Gly Leu Thr Gly His Ile Thr Phe Asn Lys Thr Asn Gly Leu
    340                 345                 350
Arg Lys Asp Phe Asp Leu Asp Ile Ile Ser Leu Lys Glu Glu Gly Thr
355                 360                 365                 370
Glu Lys Ile Gly Ile Trp Asn Ser Asn Ser Gly Leu Asn Met Thr Asp
                375                 380                 385
Ser Asn Lys Asp Lys Ser Ser Asn Ile Thr Asp Ser Leu Ala Asn Arg
            390                 395                 400
Thr Leu Ile Val Thr Thr Ile Leu Glu Glu Pro Tyr Val Met Tyr Arg
        405                 410                 415
Lys Ser Asp Lys Pro Leu Tyr Gly Asn Asp Arg Phe Glu Gly Tyr Cys
    420                 425                 430
Leu Asp Leu Leu Lys Glu Leu Ser Asn Ile Leu Gly Phe Ile Tyr Asp
435                 440                 445                 450
Val Lys Leu Val Pro Asp Gly Lys Tyr Gly Ala Gln Asn Asp Lys Gly
                455                 460                 465
Glu Trp Asn Gly Met Val Lys Glu Leu Ile Asp His Arg Ala Asp Leu
            470                 475                 480
```

-continued

```
Ala Val Ala Pro Leu Thr Ile Thr Tyr Val Arg Glu Lys Val Ile Asp
            485                 490                 495

Phe Ser Lys Pro Phe Met Thr Leu Gly Ile Ser Ile Leu Tyr Arg Lys
500                 505                 510

Pro Asn Gly Thr Asn Pro Gly Val Phe Ser Phe Leu Asn Pro Leu Ser
515                 520                 525                 530

Pro Asp Ile Trp Met Tyr Val Leu Leu Ala Cys Leu Gly Val Ser Cys
                535                 540                 545

Val Leu Phe Val Ile Ala Arg Phe Thr Pro Tyr Glu Trp Tyr Asn Pro
            550                 555                 560

His Pro Cys Asn Pro Asp Ser Asp Val Val Glu Asn Asn Phe Thr Leu
            565                 570                 575

Leu Asn Ser Phe Trp Phe Gly Val Gly Ala Leu Met Arg Gln Gly Ser
580                 585                 590

Glu Leu Met Pro Lys Ala Leu Ser Thr Arg Ile Val Gly Gly Ile Trp
595                 600                 605                 610

Trp Phe Phe Thr Leu Ile Ile Ile Ser Ser Tyr Thr Ala Asn Leu Ala
                615                 620                 625

Ala Phe Leu Thr Val Glu Arg Met Glu Ser Pro Ile Asp Ser Ala Asp
            630                 635                 640

Asp Leu Ala Lys Gln Thr Lys Ile Glu Tyr Gly Ala Val Arg Asp Gly
            645                 650                 655

Ser Thr Met Thr Phe Phe Lys Lys Ser Lys Ile Ser Thr Tyr Glu Lys
            660                 665                 670

Met Trp Ala Phe Met Ser Ser Arg Gln Gln Thr Ala Leu Val Arg Asn
675                 680                 685                 690

Ser Asp Glu Gly Ile Gln Arg Val Leu Thr Thr Asp Tyr Ala Leu Leu
                695                 700                 705

Met Glu Ser Thr Ser Ile Glu Tyr Val Thr Gln Arg Asn Cys Asn Leu
            710                 715                 720

Thr Gln Ile Gly Gly Leu Ile Asp Ser Lys Gly Tyr Gly Val Gly Thr
            725                 730                 735

Pro Ile Gly Ser Pro Tyr Arg Asp Lys Ile Thr Ile Ala Ile Leu Gln
740                 745                 750

Leu Gln Glu Glu Gly Lys Leu His Met Met Lys Glu Lys Trp Trp Arg
755                 760                 765                 770

Gly Asn Gly Cys Pro Glu Glu Asp Asn Lys Glu Ala Ser Ala Leu Gly
                775                 780                 785

Val Glu Asn Ile Gly Gly Ile Phe Ile Val Leu Ala Ala Gly Leu Val
            790                 795                 800

Leu Ser Val Phe Val Ala Ile Gly Glu Phe Ile Tyr Lys Ser Arg Lys
            805                 810                 815

Asn Asn Asp Ile Glu Gln Cys Leu Ser Phe Asn Ala Ile Met Glu Glu
820                 825                 830

Leu Gly Ile Ser Leu Lys Asn Gln Lys Lys Ile Lys Lys Lys Ser Arg
835                 840                 845                 850

Thr Lys Gly Lys Ser Ser Phe Thr Ser Ile Leu Thr Cys His Gln Arg
                855                 860                 865

Arg Thr Gln Arg Lys Glu Thr Val Ala
            870                 875
```

(2) INFORMATION FOR SEQ ID NO:11:

(i) SEQUENCE CHARACTERISTICS:
        (A) LENGTH: 2878 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig_peptide
        (B) LOCATION: 134..226

(ix) FEATURE:
        (A) NAME/KEY: mat_peptide
        (B) LOCATION: 227..2860

(ix) FEATURE:
        (A) NAME/KEY: CDS
        (B) LOCATION: 134..2860

(xi) SEQUENCE DESCRIPTION: SEQ ID NO:11:

```
GAATTCCCTC TCTATGACCA TGCCGTGATC GTGTCTGCGG TCACCACTCG ACGCATCCTC         60

ATTTCTACCC GAACCCAGGA GCCGAACGCT AGATCGGGGA AGTGGGTGCC GTGCGTGTGG        120

GCACAGAAAC ACC ATG AAG ATT ATT TTC CCG ATT CTA AGT AAT CCA GTC          169
            Met Lys Ile Ile Phe Pro Ile Leu Ser Asn Pro Val
            -31 -30             -25                 -20

TTC AGG CGC ACC GTT AAA CTC CTG CTC TGT TTA CTG TGG ATT GGA TAT         217
Phe Arg Arg Thr Val Lys Leu Leu Leu Cys Leu Leu Trp Ile Gly Tyr
            -15                 -10                 -5

TCT CAA GGA ACC ACA CAT GTA TTA AGA TTT GGT GGT ATT TTT GAA TAT         265
Ser Gln Gly Thr Thr His Val Leu Arg Phe Gly Gly Ile Phe Glu Tyr
              1               5                  10

GTG GAA TCT GGC CCA ATG GGA GCT GAG GAA CTT GCA TTC AGA TTT GCT         313
Val Glu Ser Gly Pro Met Gly Ala Glu Glu Leu Ala Phe Arg Phe Ala
     15              20                  25

GTG AAC ACA ATT AAC AGA AAC AGA ACA TTG CTA CCC AAT ACT ACC CTT         361
Val Asn Thr Ile Asn Arg Asn Arg Thr Leu Leu Pro Asn Thr Thr Leu
 30              35                  40                  45

ACC TAT GAT ACC CAG AAG ATA AAC CTT TAT GAT AGT TTT GAA GCA TCC         409
Thr Tyr Asp Thr Gln Lys Ile Asn Leu Tyr Asp Ser Phe Glu Ala Ser
                 50                  55                  60

AAG AAA GCC TGT GAT CAG CTG TCT CTT GGG GTG GCT GCC ATC TTC GGG         457
Lys Lys Ala Cys Asp Gln Leu Ser Leu Gly Val Ala Ala Ile Phe Gly
                     65                  70                  75

CCT TCA CAC AGC TCA TCA GCA AAC GCA GTG CAG TCC ATC TGC AAT GCT         505
Pro Ser His Ser Ser Ser Ala Asn Ala Val Gln Ser Ile Cys Asn Ala
             80                  85                  90

CTG GGA GTT CCC CAC ATA CAG ACC CGC TGG AAG CAC CAG GTG TCA GAC         553
Leu Gly Val Pro His Ile Gln Thr Arg Trp Lys His Gln Val Ser Asp
         95                 100                 105

AAC AAA GAT TCC TTC TAT GTC AGT CTC TAC CCA GAC TTC TCT TCA CTC         601
Asn Lys Asp Ser Phe Tyr Val Ser Leu Tyr Pro Asp Phe Ser Ser Leu
110                 115                 120                 125

AGC CGT GCC ATT TTA GAC CTG GTG CAG TTT TTC AAG TGG AAA ACC GTC         649
Ser Arg Ala Ile Leu Asp Leu Val Gln Phe Phe Lys Trp Lys Thr Val
                130                 135                 140

ACG GTT GTG TAT GAT GAC AGC ACT GGT CTC ATT CGT TTG CAA GAG CTC         697
Thr Val Val Tyr Asp Asp Ser Thr Gly Leu Ile Arg Leu Gln Glu Leu
            145                 150                 155

ATC AAA GCT CCA TCA AGG TAT AAT CTT CGA CTC AAA ATT CGT CAG TTA         745
Ile Lys Ala Pro Ser Arg Tyr Asn Leu Arg Leu Lys Ile Arg Gln Leu
        160                 165                 170
```

```
CCT GCT GAT ACA AAG GAT GCA AAA CCC TTA CTA AAA GAA ATG AAA AGA      793
Pro Ala Asp Thr Lys Asp Ala Lys Pro Leu Leu Lys Glu Met Lys Arg
    175             180                 185

GGC AAG GAG TTT CAT GTA ATC TTT GAT TGT AGC CAT GAA ATG GCA GCA      841
Gly Lys Glu Phe His Val Ile Phe Asp Cys Ser His Glu Met Ala Ala
190             195                 200                 205

GGC ATT TTA AAA CAG GCA TTA GCT ATG GGA ATG ATG ACA GAA TAC TAT      889
Gly Ile Leu Lys Gln Ala Leu Ala Met Gly Met Met Thr Glu Tyr Tyr
                210                 215                 220

CAT TAT ATC TTT ACC ACT CTG GAC CTC TTT GCT CTT GAT GTT GAG CCC      937
His Tyr Ile Phe Thr Thr Leu Asp Leu Phe Ala Leu Asp Val Glu Pro
            225                 230                 235

TAC CGA TAC AGT GGT GTT AAC ATG ACA GGG TTC AGA ATA TTA AAT ACA      985
Tyr Arg Tyr Ser Gly Val Asn Met Thr Gly Phe Arg Ile Leu Asn Thr
        240                 245                 250

GAA AAT ACC CAA GTC TCC TCC ATC ATT GAA AAG TGG TCG ATG GAA CGA     1033
Glu Asn Thr Gln Val Ser Ser Ile Ile Glu Lys Trp Ser Met Glu Arg
    255                 260                 265

TTG CAG GCA CCT CCG AAA CCC GAT TCA GGT TTG CTG GAT GGA TTT ATG     1081
Leu Gln Ala Pro Pro Lys Pro Asp Ser Gly Leu Leu Asp Gly Phe Met
270             275                 280                 285

ACG ACT GAT GCT GCT CTA ATG TAT GAT GCT GTG CAT GTG GTG TCT GTG     1129
Thr Thr Asp Ala Ala Leu Met Tyr Asp Ala Val His Val Val Ser Val
                290                 295                 300

GCC GTT CAA CAG TTT CCC CAG ATG ACA GTC AGT TCC TTG CAG TGT AAT     1177
Ala Val Gln Gln Phe Pro Gln Met Thr Val Ser Ser Leu Gln Cys Asn
            305                 310                 315

CGA CAT AAA CCC TGG CGC TTC GGG ACC CGC TTT ATG AGT CTA ATT AAA     1225
Arg His Lys Pro Trp Arg Phe Gly Thr Arg Phe Met Ser Leu Ile Lys
        320                 325                 330

GAG GCA CAT TGG GAA GGC CTC ACA GGC AGA ATA ACT TTC AAC AAA ACC     1273
Glu Ala His Trp Glu Gly Leu Thr Gly Arg Ile Thr Phe Asn Lys Thr
    335                 340                 345

AAT GGC TTG AGA ACA GAT TTT GAT TTG GAT GTG ATC AGT CTG AAG GAA     1321
Asn Gly Leu Arg Thr Asp Phe Asp Leu Asp Val Ile Ser Leu Lys Glu
350             355                 360                 365

GAA GGT CTA GAA AAG ATT GGA ACG TGG GAT CCA GCC AGT GGC CTG AAT     1369
Glu Gly Leu Glu Lys Ile Gly Thr Trp Asp Pro Ala Ser Gly Leu Asn
                370                 375                 380

ATG ACA GAA AGT CAA AAG GGA AAG CCA GCG AAC ATC ACA GAT TCC TTA     1417
Met Thr Glu Ser Gln Lys Gly Lys Pro Ala Asn Ile Thr Asp Ser Leu
            385                 390                 395

TCC AAT CGT TCT TTG ATT GTT ACC ACC ATT TTG GAA GAG CCT TAT GTC     1465
Ser Asn Arg Ser Leu Ile Val Thr Thr Ile Leu Glu Glu Pro Tyr Val
        400                 405                 410

CTT TTT AAG AAG TCT GAC AAA CCT CTC TAT GGT AAT GAT CGA TTT GAA     1513
Leu Phe Lys Lys Ser Asp Lys Pro Leu Tyr Gly Asn Asp Arg Phe Glu
    415                 420                 425

GGC TAT TGC ATT GAT CTC CTC AGA GAG TTA TCT ACA ATC CTT GGC TTT     1561
Gly Tyr Cys Ile Asp Leu Leu Arg Glu Leu Ser Thr Ile Leu Gly Phe
430             435                 440                 445

ACA TAT GAA ATT AGA CTT GTG GAA GAT GGG AAA TAT GGA GCC CAG GAT     1609
Thr Tyr Glu Ile Arg Leu Val Glu Asp Gly Lys Tyr Gly Ala Gln Asp
                450                 455                 460

GAT GCC AAT GGA CAA TGG AAT GGA ATG GTT CGT GAA CTA ATT GAT CAT     1657
Asp Ala Asn Gly Gln Trp Asn Gly Met Val Arg Glu Leu Ile Asp His
            465                 470                 475

AAA GCT GAC CTT GCA GTT GCT CCA CTG GCT ATT ACC TAT GTT CGA GAG     1705
Lys Ala Asp Leu Ala Val Ala Pro Leu Ala Ile Thr Tyr Val Arg Glu
        480                 485                 490
```

```
AAG GTC ATC GAC TTT TCC AAG CCC TTT ATG ACA CTT GGA ATA AGT ATT           1753
Lys Val Ile Asp Phe Ser Lys Pro Phe Met Thr Leu Gly Ile Ser Ile
    495                 500                 505

TTG TAC CGC AAG CCC AAT GGT ACA AAC CCA GGC GTC TTC TCC TTC CTG           1801
Leu Tyr Arg Lys Pro Asn Gly Thr Asn Pro Gly Val Phe Ser Phe Leu
510                 515                 520                 525

AAT CCT CTC TCC CCT GAT ATC TGG ATG TAT GTT CTG CTG GCT TGC TTG           1849
Asn Pro Leu Ser Pro Asp Ile Trp Met Tyr Val Leu Leu Ala Cys Leu
                530                 535                 540

GGT GTC AGT TGT GTG CTC TTT GTC ATA GCC AGG TTT AGT CCT TAT GAG           1897
Gly Val Ser Cys Val Leu Phe Val Ile Ala Arg Phe Ser Pro Tyr Glu
        545                 550                 555

TGG TAT AAT CCA CAC CCT TGC AAC CCT GAC TCA GAC GTG GTG GAA AAC           1945
Trp Tyr Asn Pro His Pro Cys Asn Pro Asp Ser Asp Val Val Glu Asn
            560                 565                 570

AAT TTT ACC TTG CTA AAT AGT TTC TGG TTT GGA GTT GGA GCT CTC ATG           1993
Asn Phe Thr Leu Leu Asn Ser Phe Trp Phe Gly Val Gly Ala Leu Met
575                 580                 585

CGG CAA GGT TCT GAG CTC ATG CCC AAA GCA CTG TCC ACC AGG ATA GTG           2041
Arg Gln Gly Ser Glu Leu Met Pro Lys Ala Leu Ser Thr Arg Ile Val
590                 595                 600                 605

GGA GGC ATT TGG TGG TTT TTC ACA CTT ATC ATC ATT TCT TCG TAT ACT           2089
Gly Gly Ile Trp Trp Phe Phe Thr Leu Ile Ile Ile Ser Ser Tyr Thr
                610                 615                 620

GCT AAC TTA GCC GCC TTT CTG ACA GTG GAA CGC ATG GAA TCC CCT ATT           2137
Ala Asn Leu Ala Ala Phe Leu Thr Val Glu Arg Met Glu Ser Pro Ile
            625                 630                 635

GAC TCT GCT GAT GAT TTA GCT AAA CAA ACC AAG ATA GAA TAT GGA GCA           2185
Asp Ser Ala Asp Asp Leu Ala Lys Gln Thr Lys Ile Glu Tyr Gly Ala
            640                 645                 650

GTA GAG GAT GGT GCA ACC ATG ACT TTT TTC AAG AAA TCA AAA ATC TCC           2233
Val Glu Asp Gly Ala Thr Met Thr Phe Phe Lys Lys Ser Lys Ile Ser
655                 660                 665

ACG TAT GAC AAA ATG TGG GCC TTT ATG AGT AGC AGA AGG CAG TCA GTG           2281
Thr Tyr Asp Lys Met Trp Ala Phe Met Ser Ser Arg Arg Gln Ser Val
670                 675                 680                 685

CTG GTC AAA AGT AAT GAA GAA GGA ATC CAG CGA GTC CTC ACC TCT GAT           2329
Leu Val Lys Ser Asn Glu Glu Gly Ile Gln Arg Val Leu Thr Ser Asp
                690                 695                 700

TAT GCT TTC CTA ATG GAG TCA ACA ACC ATC GAG TTT GTT ACC CAG CGG           2377
Tyr Ala Phe Leu Met Glu Ser Thr Thr Ile Glu Phe Val Thr Gln Arg
            705                 710                 715

AAC TGT AAC CTG ACA CAG ATT GGC GGC CTT ATA GAC TCT AAA GGT TAT           2425
Asn Cys Asn Leu Thr Gln Ile Gly Gly Leu Ile Asp Ser Lys Gly Tyr
            720                 725                 730

GGC GTT GGC ACT CCC ATG GGT TCT CCA TAT CGA GAC AAA ATT ACC ATA           2473
Gly Val Gly Thr Pro Met Gly Ser Pro Tyr Arg Asp Lys Ile Thr Ile
735                 740                 745

GCA ATT CTT CAG CTG CAA GAG GAA GGC AAA CTG CAT ATG ATG AAG GAG           2521
Ala Ile Leu Gln Leu Gln Glu Glu Gly Lys Leu His Met Met Lys Glu
750                 755                 760                 765

AAA TGG TGG AGG GGC AAT GGT TGC CCA GAA GAG GAA AGC AAA GAG GCC           2569
Lys Trp Trp Arg Gly Asn Gly Cys Pro Glu Glu Glu Ser Lys Glu Ala
                770                 775                 780

AGT GCC CTG GGG GTT CAG AAT ATT GGT GGC ATC TTC ATT GTT CTG GCA           2617
Ser Ala Leu Gly Val Gln Asn Ile Gly Gly Ile Phe Ile Val Leu Ala
            785                 790                 795

GCC GGC TTG GTG CTT TCA GTT TTT GTG GCA GTG GGA GAA TTT TTA TAC           2665
Ala Gly Leu Val Leu Ser Val Phe Val Ala Val Gly Glu Phe Leu Tyr
            800                 805                 810
```

```
AAA TCC AAA AAA AAC GCT CAA TTG GAA AAG AGG TCC TTC TGT AGT GCC         2713
Lys Ser Lys Lys Asn Ala Gln Leu Glu Lys Arg Ser Phe Cys Ser Ala
815                 820                 825

ATG GTA GAA GAA TTG AGG ATG TCC CTG AAG TGC CAG CGT CGG TTA AAA         2761
Met Val Glu Glu Leu Arg Met Ser Leu Lys Cys Gln Arg Arg Leu Lys
830                 835                 840                 845

CAT AAG CCA CAG GCC CCA GTT ATT GTG AAA ACA GAA GAA GTT ATC AAC         2809
His Lys Pro Gln Ala Pro Val Ile Val Lys Thr Glu Glu Val Ile Asn
                850                 855                 860

ATG CAC ACA TTT AAC GAC AGA AGG TTG CCA GGT AAA GAA ACC ATG GCA         2857
Met His Thr Phe Asn Asp Arg Arg Leu Pro Gly Lys Glu Thr Met Ala
            865                 870                 875

TAAAGCTGGG AGGCGGAATT C                                                  2878

(2) INFORMATION FOR SEQ ID NO:12:

(i) SEQUENCE CHARACTERISTICS:
        (A) LENGTH: 908 amino acids
        (B) TYPE: amino acid
        (D) TOPOLOGY: linear (ii) MOLECULE TYPE: protein (xi) SEQUENCE DESCRIPTION: SEQ ID NO:12:

Met Lys Ile Ile Phe Pro Ile Leu Ser Asn Pro Val Phe Arg Arg Thr
-31 -30             -25                 -20

Val Lys Leu Leu Leu Cys Leu Leu Trp Ile Gly Tyr Ser Gln Gly Thr
-15             -10                  -5                   1

Thr His Val Leu Arg Phe Gly Gly Ile Phe Glu Tyr Val Glu Ser Gly
                5                  10                  15

Pro Met Gly Ala Glu Glu Leu Ala Phe Arg Phe Ala Val Asn Thr Ile
            20                  25                  30

Asn Arg Asn Arg Thr Leu Leu Pro Asn Thr Thr Leu Thr Tyr Asp Thr
        35                  40                  45

Gln Lys Ile Asn Leu Tyr Asp Ser Phe Glu Ala Ser Lys Lys Ala Cys
50                  55                  60                  65

Asp Gln Leu Ser Leu Gly Val Ala Ala Ile Phe Gly Pro Ser His Ser
                70                  75                  80

Ser Ser Ala Asn Ala Val Gln Ser Ile Cys Asn Ala Leu Gly Val Pro
            85                  90                  95

His Ile Gln Thr Arg Trp Lys His Gln Val Ser Asp Asn Lys Asp Ser
        100                 105                 110

Phe Tyr Val Ser Leu Tyr Pro Asp Phe Ser Ser Leu Ser Arg Ala Ile
    115                 120                 125

Leu Asp Leu Val Gln Phe Phe Lys Trp Lys Thr Val Thr Val Val Tyr
130                 135                 140                 145

Asp Asp Ser Thr Gly Leu Ile Arg Leu Gln Glu Leu Ile Lys Ala Pro
                150                 155                 160

Ser Arg Tyr Asn Leu Arg Leu Lys Ile Arg Gln Leu Pro Ala Asp Thr
            165                 170                 175

Lys Asp Ala Lys Pro Leu Leu Lys Glu Met Lys Arg Gly Lys Glu Phe
        180                 185                 190

His Val Ile Phe Asp Cys Ser His Glu Met Ala Ala Gly Ile Leu Lys
    195                 200                 205

Gln Ala Leu Ala Met Gly Met Met Thr Glu Tyr Tyr His Tyr Ile Phe
210                 215                 220                 225
```

```
Thr Thr Leu Asp Leu Phe Ala Leu Asp Val Glu Pro Tyr Arg Tyr Ser
            230                 235                 240

Gly Val Asn Met Thr Gly Phe Arg Ile Leu Asn Thr Glu Asn Thr Gln
            245                 250                 255

Val Ser Ser Ile Ile Glu Lys Trp Ser Met Glu Arg Leu Gln Ala Pro
            260                 265                 270

Pro Lys Pro Asp Ser Gly Leu Leu Asp Gly Phe Met Thr Thr Asp Ala
275                 280                 285

Ala Leu Met Tyr Asp Ala Val His Val Ser Val Ala Val Gln Gln
290                 295                 300                 305

Phe Pro Gln Met Thr Val Ser Ser Leu Gln Cys Asn Arg His Lys Pro
            310                 315                 320

Trp Arg Phe Gly Thr Arg Phe Met Ser Leu Ile Lys Glu Ala His Trp
            325                 330                 335

Glu Gly Leu Thr Gly Arg Ile Thr Phe Asn Lys Thr Asn Gly Leu Arg
            340                 345                 350

Thr Asp Phe Asp Leu Asp Val Ile Ser Leu Lys Glu Glu Gly Leu Glu
355                 360                 365

Lys Ile Gly Thr Trp Asp Pro Ala Ser Gly Leu Asn Met Thr Glu Ser
370                 375                 380                 385

Gln Lys Gly Lys Pro Ala Asn Ile Thr Asp Ser Leu Ser Asn Arg Ser
            390                 395                 400

Leu Ile Val Thr Thr Ile Leu Glu Glu Pro Tyr Val Leu Phe Lys Lys
            405                 410                 415

Ser Asp Lys Pro Leu Tyr Gly Asn Asp Arg Phe Glu Gly Tyr Cys Ile
            420                 425                 430

Asp Leu Leu Arg Glu Leu Ser Thr Ile Leu Gly Phe Thr Tyr Glu Ile
            435                 440                 445

Arg Leu Val Glu Asp Gly Lys Tyr Gly Ala Gln Asp Ala Asn Gly
450                 455                 460                 465

Gln Trp Asn Gly Met Val Arg Glu Leu Ile Asp His Lys Ala Asp Leu
            470                 475                 480

Ala Val Ala Pro Leu Ala Ile Thr Tyr Val Arg Glu Lys Val Ile Asp
            485                 490                 495

Phe Ser Lys Pro Phe Met Thr Leu Gly Ile Ser Ile Leu Tyr Arg Lys
            500                 505                 510

Pro Asn Gly Thr Asn Pro Gly Val Phe Ser Phe Leu Asn Pro Leu Ser
            515                 520                 525

Pro Asp Ile Trp Met Tyr Val Leu Leu Ala Cys Leu Gly Val Ser Cys
530                 535                 540                 545

Val Leu Phe Val Ile Ala Arg Phe Ser Pro Tyr Glu Trp Tyr Asn Pro
            550                 555                 560

His Pro Cys Asn Pro Asp Ser Asp Val Val Glu Asn Asn Phe Thr Leu
            565                 570                 575

Leu Asn Ser Phe Trp Phe Gly Val Gly Ala Leu Met Arg Gln Gly Ser
            580                 585                 590

Glu Leu Met Pro Lys Ala Leu Ser Thr Arg Ile Val Gly Gly Ile Trp
            595                 600                 605

Trp Phe Phe Thr Leu Ile Ile Ile Ser Ser Tyr Thr Ala Asn Leu Ala
610                 615                 620                 625

Ala Phe Leu Thr Val Glu Arg Met Glu Ser Pro Ile Asp Ser Ala Asp
            630                 635                 640
```

```
Asp Leu Ala Lys Gln Thr Lys Ile Glu Tyr Gly Ala Val Glu Asp Gly
            645                 650                 655

Ala Thr Met Thr Phe Phe Lys Lys Ser Lys Ile Ser Thr Tyr Asp Lys
        660                 665                 670

Met Trp Ala Phe Met Ser Ser Arg Arg Gln Ser Val Leu Val Lys Ser
    675                 680                 685

Asn Glu Glu Gly Ile Gln Arg Val Leu Thr Ser Asp Tyr Ala Phe Leu
690                 695                 700                 705

Met Glu Ser Thr Thr Ile Glu Phe Val Thr Gln Arg Asn Cys Asn Leu
            710                 715                 720

Thr Gln Ile Gly Gly Leu Ile Asp Ser Lys Gly Tyr Gly Val Gly Thr
            725                 730                 735

Pro Met Gly Ser Pro Tyr Arg Asp Lys Ile Thr Ile Ala Ile Leu Gln
        740                 745                 750

Leu Gln Glu Glu Gly Lys Leu His Met Met Lys Glu Lys Trp Trp Arg
    755                 760                 765

Gly Asn Gly Cys Pro Glu Glu Ser Lys Glu Ala Ser Ala Leu Gly
770                 775                 780                 785

Val Gln Asn Ile Gly Gly Ile Phe Ile Val Leu Ala Ala Gly Leu Val
            790                 795                 800

Leu Ser Val Phe Val Ala Val Gly Glu Phe Leu Tyr Lys Ser Lys Lys
        805                 810                 815

Asn Ala Gln Leu Glu Lys Arg Ser Phe Cys Ser Ala Met Val Glu Glu
    820                 825                 830

Leu Arg Met Ser Leu Lys Cys Gln Arg Arg Leu Lys His Lys Pro Gln
    835                 840                 845

Ala Pro Val Ile Val Lys Thr Glu Glu Val Ile Asn Met His Thr Phe
850                 855                 860                 865

Asn Asp Arg Arg Leu Pro Gly Lys Glu Thr Met Ala
            870                 875

(2) INFORMATION FOR SEQ ID NO:13:

(i) SEQUENCE CHARACTERISTICS:
        (A) LENGTH: 2878 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig_peptide
        (B) LOCATION: 134..226

(ix) FEATURE:
        (A) NAME/KEY: mat_peptide
        (B) LOCATION: 227..2860

(ix) FEATURE:
        (A) NAME/KEY: CDS
        (B) LOCATION: 134..2860

(xi) SEQUENCE DESCRIPTION: SEQ ID NO:13:

GAATTCCCTC TCTATGACCA TGCCGTGATC GTGTCTGCGG TCACCACTCG ACGCATCCTC      60

ATTTCTACCC GAACCCAGGA GCCGAACGCT AGATCGGGGA AGTGGGTGCC GTGCGTGTGG     120

GCACAGAAAC ACC ATG AAG ATT ATT TTC CCG ATT CTA AGT AAT CCA GTC       169
           Met Lys Ile Ile Phe Pro Ile Leu Ser Asn Pro Val
           -31 -30                 -25                 -20
```

```
TTC AGG CGC ACC GTT AAA CTC CTG CTC TGT TTA CTG TGG ATT GGA TAT      217
Phe Arg Arg Thr Val Lys Leu Leu Leu Cys Leu Leu Trp Ile Gly Tyr
            -15             -10                         -5

TCT CAA GGA ACC ACA CAT GTA TTA AGA TTT GGT GGT ATT TTT GAA TAT      265
Ser Gln Gly Thr Thr His Val Leu Arg Phe Gly Gly Ile Phe Glu Tyr
            1           5                       10

GTG GAA TCT GGC CCA ATG GGA GCT GAG GAA CTT GCA TTC AGA TTT GCT      313
Val Glu Ser Gly Pro Met Gly Ala Glu Glu Leu Ala Phe Arg Phe Ala
    15              20                      25

GTG AAC ACA ATT AAC AGA AAC AGA ACA TTG CTA CCC AAT ACT ACC CTT      361
Val Asn Thr Ile Asn Arg Asn Arg Thr Leu Leu Pro Asn Thr Thr Leu
30              35                      40                  45

ACC TAT GAT ACC CAG AAG ATA AAC CTT TAT GAT AGT TTT GAA GCA TCC      409
Thr Tyr Asp Thr Gln Lys Ile Asn Leu Tyr Asp Ser Phe Glu Ala Ser
                50                      55                  60

AAG AAA GCC TGT GAT CAG CTG TCT CTT GGG GTG GCT GCC ATC TTC GGG      457
Lys Lys Ala Cys Asp Gln Leu Ser Leu Gly Val Ala Ala Ile Phe Gly
                65                      70                  75

CCT TCA CAC AGC TCA TCA GCA AAC GCA GTG CAG TCC ATC TGC AAT GCT      505
Pro Ser His Ser Ser Ser Ala Asn Ala Val Gln Ser Ile Cys Asn Ala
            80                      85                  90

CTG GGA GTT CCC CAC ATA CAG ACC CGC TGG AAG CAC CAG GTG TCA GAC      553
Leu Gly Val Pro His Ile Gln Thr Arg Trp Lys His Gln Val Ser Asp
    95                      100                     105

AAC AAA GAT TCC TTC TAT GTC AGT CTC TAC CCA GAC TTC TCT TCA CTC      601
Asn Lys Asp Ser Phe Tyr Val Ser Leu Tyr Pro Asp Phe Ser Ser Leu
110             115                     120                     125

AGC CGT GCC ATT TTA GAC CTG GTG CAG TTT TTC AAG TGG AAA ACC GTC      649
Ser Arg Ala Ile Leu Asp Leu Val Gln Phe Phe Lys Trp Lys Thr Val
                130                     135                     140

ACG GTT GTG TAT GAT GAC AGC ACT GGT CTC ATT CGT TTG CAA GAG CTC      697
Thr Val Val Tyr Asp Asp Ser Thr Gly Leu Ile Arg Leu Gln Glu Leu
                145                     150                     155

ATC AAA GCT CCA TCA AGG TAT AAT CTT CGA CTC AAA ATT CGT CAG TTA      745
Ile Lys Ala Pro Ser Arg Tyr Asn Leu Arg Leu Lys Ile Arg Gln Leu
            160                     165                     170

CCT GCT GAT ACA AAG GAT GCA AAA CCC TTA CTA AAA GAA ATG AAA AGA      793
Pro Ala Asp Thr Lys Asp Ala Lys Pro Leu Leu Lys Glu Met Lys Arg
            175                     180                     185

GGC AAG GAG TTT CAT GTA ATC TTT GAT TGT AGC CAT GAA ATG GCA GCA      841
Gly Lys Glu Phe His Val Ile Phe Asp Cys Ser His Glu Met Ala Ala
190                     195                     200                     205

GGC ATT TTA AAA CAG GCA TTA GCT ATG GGA ATG ATG ACA GAA TAC TAT      889
Gly Ile Leu Lys Gln Ala Leu Ala Met Gly Met Met Thr Glu Tyr Tyr
                210                     215                     220

CAT TAT ATC TTT ACC ACT CTG GAC CTC TTT GCT CTT GAT GTT GAG CCC      937
His Tyr Ile Phe Thr Thr Leu Asp Leu Phe Ala Leu Asp Val Glu Pro
                225                     230                     235

TAC CGA TAC AGT GGT GTT AAC ATG ACA GGG TTC AGA ATA TTA AAT ACA      985
Tyr Arg Tyr Ser Gly Val Asn Met Thr Gly Phe Arg Ile Leu Asn Thr
            240                     245                     250

GAA AAT ACC CAA GTC TCC TCC ATC ATT GAA AAG TGG TCG ATG GAA CGA     1033
Glu Asn Thr Gln Val Ser Ser Ile Ile Glu Lys Trp Ser Met Glu Arg
            255                     260                     265

TTG CAG GCA CCT CCG AAA CCC GAT TCA GGT TTG CTG GAT GGA TTT ATG     1081
Leu Gln Ala Pro Pro Lys Pro Asp Ser Gly Leu Leu Asp Gly Phe Met
270             275                     280                     285

ACG ACT GAT GCT GCT CTA ATG TAT GAT GCT GTG CAT GTG GTG TCT GTG     1129
Thr Thr Asp Ala Ala Leu Met Tyr Asp Ala Val His Val Val Ser Val
                290                     295                     300
```

```
GCC GTT CAA CAG TTT CCC CAG ATG ACA GTC AGT TCC TTG CAG TGT AAT    1177
Ala Val Gln Gln Phe Pro Gln Met Thr Val Ser Ser Leu Gln Cys Asn
            305                 310                 315

CGA CAT AAA CCC TGG CGC TTC GGG ACC CGC TTT ATG AGT CTA ATT AAA    1225
Arg His Lys Pro Trp Arg Phe Gly Thr Arg Phe Met Ser Leu Ile Lys
            320                 325                 330

GAG GCA CAT TGG GAA GGC CTC ACA GGC AGA ATA ACT TTC AAC AAA ACC    1273
Glu Ala His Trp Glu Gly Leu Thr Gly Arg Ile Thr Phe Asn Lys Thr
            335                 340                 345

AAT GGC TTG AGA ACA GAT TTT GAT TTG GAT GTG ATC AGT CTG AAG GAA    1321
Asn Gly Leu Arg Thr Asp Phe Asp Leu Asp Val Ile Ser Leu Lys Glu
350                 355                 360                 365

GAA GGT CTA GAA AAG ATT GGA ACG TGG GAT CCA GCC AGT GGC CTG AAT    1369
Glu Gly Leu Glu Lys Ile Gly Thr Trp Asp Pro Ala Ser Gly Leu Asn
                370                 375                 380

ATG ACA GAA AGT CAA AAG GGA AAG CCA GCG AAC ATC ACA GAT TCC TTA    1417
Met Thr Glu Ser Gln Lys Gly Lys Pro Ala Asn Ile Thr Asp Ser Leu
                385                 390                 395

TCC AAT CGT TCT TTG ATT GTT ACC ACC ATT TTG GAA GAG CCT TAT GTC    1465
Ser Asn Arg Ser Leu Ile Val Thr Thr Ile Leu Glu Glu Pro Tyr Val
                400                 405                 410

CTT TTT AAG AAG TCT GAC AAA CCT CTC TAT GGT AAT GAT CGA TTT GAA    1513
Leu Phe Lys Lys Ser Asp Lys Pro Leu Tyr Gly Asn Asp Arg Phe Glu
            415                 420                 425

GGC TAT TGC ATT GAT CTC CTC AGA GAG TTA TCT ACA ATC CTT GGC TTT    1561
Gly Tyr Cys Ile Asp Leu Leu Arg Glu Leu Ser Thr Ile Leu Gly Phe
430                 435                 440                 445

ACA TAT GAA ATT AGA CTT GTG GAA GAT GGG AAA TAT GGA GCC CAG GAT    1609
Thr Tyr Glu Ile Arg Leu Val Glu Asp Gly Lys Tyr Gly Ala Gln Asp
                450                 455                 460

GAT GCC AAT GGA CAA TGG AAT GGA ATG GTT CGT GAA CTA ATT GAT CAT    1657
Asp Ala Asn Gly Gln Trp Asn Gly Met Val Arg Glu Leu Ile Asp His
                465                 470                 475

AAA GCT GAC CTT GCA GTT GCT CCA CTG GCT ATT ACC TAT GTT CGA GAG    1705
Lys Ala Asp Leu Ala Val Ala Pro Leu Ala Ile Thr Tyr Val Arg Glu
            480                 485                 490

AAG GTC ATC GAC TTT TCC AAG CCC TTT ATG ACA CTT GGA ATA AGT ATT    1753
Lys Val Ile Asp Phe Ser Lys Pro Phe Met Thr Leu Gly Ile Ser Ile
            495                 500                 505

TTG TAC CGC AAG CCC AAT GGT ACA AAC CCA GGC GTC TTC TCC TTC CTG    1801
Leu Tyr Arg Lys Pro Asn Gly Thr Asn Pro Gly Val Phe Ser Phe Leu
510                 515                 520                 525

AAT CCT CTC TCC CCT GAT ATC TGG ATG TAT NTT CTG CTG GCT TNC TTG    1849
Asn Pro Leu Ser Pro Asp Ile Trp Met Tyr Xaa Leu Leu Ala Xaa Leu
                530                 535                 540

GGT GTC AGT TGT GTG CTC TTT GTC ATA GCC AGG TTT AGT CCT TAT GAG    1897
Gly Val Ser Cys Val Leu Phe Val Ile Ala Arg Phe Ser Pro Tyr Glu
                545                 550                 555

TGG TAT AAT CCA CAC CCT TGC AAC CCT GAC TCA GAC GTG GTG GAA AAC    1945
Trp Tyr Asn Pro His Pro Cys Asn Pro Asp Ser Asp Val Val Glu Asn
                560                 565                 570

AAT TTT ACC TTG CTA AAT AGT TTC TGG TTT GGA GTT GGA GCT CTC ATG    1993
Asn Phe Thr Leu Leu Asn Ser Phe Trp Phe Gly Val Gly Ala Leu Met
            575                 580                 585

CNG CAA GGT TCT GAG CTC ATG CCC AAA GCA CTG TCC ACC AGG ATA GTG    2041
Xaa Gln Gly Ser Glu Leu Met Pro Lys Ala Leu Ser Thr Arg Ile Val
590                 595                 600                 605

GGA GGC ATT TGG TGG TTT TTC ACA CTT ATC ATC ATT TCT TCG TAT ACT    2089
Gly Gly Ile Trp Trp Phe Phe Thr Leu Ile Ile Ile Ser Ser Tyr Thr
                610                 615                 620
```

```
GCT AAC TTA GCC GCC TTT CTG ACA GTG GAA CGC ATG GAA TCC CCT ATT      2137
Ala Asn Leu Ala Ala Phe Leu Thr Val Glu Arg Met Glu Ser Pro Ile
            625                 630                 635

GAC TCT GCT GAT GAT TTA GCT AAA CAA ACC AAG ATA GAA TAT GGA GCA      2185
Asp Ser Ala Asp Asp Leu Ala Lys Gln Thr Lys Ile Glu Tyr Gly Ala
            640                 645                 650

GTA GAG GAT GGT GCA ACC ATG ACT TTT TTC AAG AAA TCA AAA ATC TCC      2233
Val Glu Asp Gly Ala Thr Met Thr Phe Phe Lys Lys Ser Lys Ile Ser
655                 660                 665

ACG TAT GAC AAA ATG TGG GCC TTT ATG AGT AGC AGA AGG CAG TCA GTG      2281
Thr Tyr Asp Lys Met Trp Ala Phe Met Ser Ser Arg Arg Gln Ser Val
670                 675                 680                 685

CTG GTC AAA AGT AAT GAA GAA GGA ATC CAG CGA GTC CTC ACC TCT GAT      2329
Leu Val Lys Ser Asn Glu Glu Gly Ile Gln Arg Val Leu Thr Ser Asp
            690                 695                 700

TAT GCT TTC CTA ATG GAG TCA ACA ACC ATC GAG TTT GTT ACC CAG CGG      2377
Tyr Ala Phe Leu Met Glu Ser Thr Thr Ile Glu Phe Val Thr Gln Arg
            705                 710                 715

AAC TGT AAC CTG ACA CAG ATT GGC GGC CTT ATA GAC TCT AAA GGT TAT      2425
Asn Cys Asn Leu Thr Gln Ile Gly Gly Leu Ile Asp Ser Lys Gly Tyr
            720                 725                 730

GGC GTT GGC ACT CCC ATG GGT TCT CCA TAT CGA GAC AAA ATT ACC ATA      2473
Gly Val Gly Thr Pro Met Gly Ser Pro Tyr Arg Asp Lys Ile Thr Ile
735                 740                 745

GCA ATT CTT CAG CTG CAA GAG GAA GGC AAA CTG CAT ATG ATG AAG GAG      2521
Ala Ile Leu Gln Leu Gln Glu Glu Gly Lys Leu His Met Met Lys Glu
750                 755                 760                 765

AAA TGG TGG AGG GGC AAT GGT TGC CCA GAA GAG GAA AGC AAA GAG GCC      2569
Lys Trp Trp Arg Gly Asn Gly Cys Pro Glu Glu Glu Ser Lys Glu Ala
            770                 775                 780

AGT GCC CTG GGG GTT CAG AAT ATT GGT GGC ATC TTC ATT GTT CTG GCA      2617
Ser Ala Leu Gly Val Gln Asn Ile Gly Gly Ile Phe Ile Val Leu Ala
            785                 790                 795

GCC GGC TTG GTG CTT TCA GTT TTT GTG GCA GTG GGA GAA TTT TTA TAC      2665
Ala Gly Leu Val Leu Ser Val Phe Val Ala Val Gly Glu Phe Leu Tyr
            800                 805                 810

AAA TCC AAA AAA AAC GCT CAA TTG GAA AAG AGG TCC TTC TGT AGT GCC      2713
Lys Ser Lys Lys Asn Ala Gln Leu Glu Lys Arg Ser Phe Cys Ser Ala
815                 820                 825

ATG GTA GAA GAA TTG AGG ATG TCC CTG AAG TGC CAG CGT CGG TTA AAA      2761
Met Val Glu Glu Leu Arg Met Ser Leu Lys Cys Gln Arg Arg Leu Lys
830                 835                 840                 845

CAT AAG CCA CAG GCC CCA GTT ATT GTG AAA ACA GAA GAA GTT ATC AAC      2809
His Lys Pro Gln Ala Pro Val Ile Val Lys Thr Glu Glu Val Ile Asn
            850                 855                 860

ATG CAC ACA TTT AAC GAC AGA AGG TTG CCA GGT AAA GAA ACC ATG GCA      2857
Met His Thr Phe Asn Asp Arg Arg Leu Pro Gly Lys Glu Thr Met Ala
            865                 870                 875

TAAAGCTGGG AGGCGGAATT C                                              2878

(2) INFORMATION FOR SEQ ID NO:14:

(i) SEQUENCE CHARACTERISTICS:
        (A) LENGTH: 908 amino acids
        (B) TYPE: amino acid
        (D) TOPOLOGY: linear (ii) MOLECULE TYPE: protein
```

(xi) SEQUENCE DESCRIPTION: SEQ ID NO:14:

```
Met Lys Ile Ile Phe Pro Ile Leu Ser Asn Pro Val Phe Arg Arg Thr
-31 -30             -25              -20
Val Lys Leu Leu Leu Cys Leu Leu Trp Ile Gly Tyr Ser Gln Gly Thr
-15             -10              -5                           1
Thr His Val Leu Arg Phe Gly Gly Ile Phe Glu Tyr Val Glu Ser Gly
             5                   10                  15
Pro Met Gly Ala Glu Glu Leu Ala Phe Arg Phe Ala Val Asn Thr Ile
         20                  25                  30
Asn Arg Asn Arg Thr Leu Leu Pro Asn Thr Thr Leu Thr Tyr Asp Thr
         35                  40                  45
Gln Lys Ile Asn Leu Tyr Asp Ser Phe Glu Ala Ser Lys Lys Ala Cys
 50                  55                  60                  65
Asp Gln Leu Ser Leu Gly Val Ala Ala Ile Phe Gly Pro Ser His Ser
                 70                  75                  80
Ser Ser Ala Asn Ala Val Gln Ser Ile Cys Asn Ala Leu Gly Val Pro
             85                  90                  95
His Ile Gln Thr Arg Trp Lys His Gln Val Ser Asp Asn Lys Asp Ser
            100                 105                 110
Phe Tyr Val Ser Leu Tyr Pro Asp Phe Ser Ser Leu Ser Arg Ala Ile
        115                 120                 125
Leu Asp Leu Val Gln Phe Phe Lys Trp Lys Thr Val Thr Val Val Tyr
130                 135                 140                 145
Asp Asp Ser Thr Gly Leu Ile Arg Leu Gln Glu Leu Ile Lys Ala Pro
                150                 155                 160
Ser Arg Tyr Asn Leu Arg Leu Lys Ile Arg Gln Leu Pro Ala Asp Thr
                165                 170                 175
Lys Asp Ala Lys Pro Leu Leu Lys Glu Met Lys Arg Gly Lys Glu Phe
            180                 185                 190
His Val Ile Phe Asp Cys Ser His Glu Met Ala Ala Gly Ile Leu Lys
        195                 200                 205
Gln Ala Leu Ala Met Gly Met Met Thr Glu Tyr Tyr His Tyr Ile Phe
210                 215                 220                 225
Thr Thr Leu Asp Leu Phe Ala Leu Asp Val Glu Pro Tyr Arg Tyr Ser
                230                 235                 240
Gly Val Asn Met Thr Gly Phe Arg Ile Leu Asn Thr Glu Asn Thr Gln
                245                 250                 255
Val Ser Ser Ile Ile Glu Lys Trp Ser Met Glu Arg Leu Gln Ala Pro
            260                 265                 270
Pro Lys Pro Asp Ser Gly Leu Leu Asp Gly Phe Met Thr Thr Asp Ala
            275                 280                 285
Ala Leu Met Tyr Asp Ala Val His Val Val Ser Val Ala Val Gln Gln
290                 295                 300                 305
Phe Pro Gln Met Thr Val Ser Ser Leu Gln Cys Asn Arg His Lys Pro
                310                 315                 320
Trp Arg Phe Gly Thr Arg Phe Met Ser Leu Ile Lys Glu Ala His Trp
            325                 330                 335
Glu Gly Leu Thr Gly Arg Ile Thr Phe Asn Lys Thr Asn Gly Leu Arg
            340                 345                 350
Thr Asp Phe Asp Leu Asp Val Ile Ser Leu Lys Glu Glu Gly Leu Glu
            355                 360                 365
Lys Ile Gly Thr Trp Asp Pro Ala Ser Gly Leu Asn Met Thr Glu Ser
370                 375                 380                 385
```

-continued

```
Gln Lys Gly Lys Pro Ala Asn Ile Thr Asp Ser Leu Ser Asn Arg Ser
            390                 395                 400

Leu Ile Val Thr Thr Ile Leu Glu Glu Pro Tyr Val Leu Phe Lys Lys
            405                 410                 415

Ser Asp Lys Pro Leu Tyr Gly Asn Asp Arg Phe Glu Gly Tyr Cys Ile
            420                 425                 430

Asp Leu Leu Arg Glu Leu Ser Thr Ile Leu Gly Phe Thr Tyr Glu Ile
435                 440                 445

Arg Leu Val Glu Asp Gly Lys Tyr Gly Ala Gln Asp Ala Asn Gly
450                 455                 460                 465

Gln Trp Asn Gly Met Val Arg Glu Leu Ile Asp His Lys Ala Asp Leu
            470                 475                 480

Ala Val Ala Pro Leu Ala Ile Thr Tyr Val Arg Glu Lys Val Ile Asp
            485                 490                 495

Phe Ser Lys Pro Phe Met Thr Leu Gly Ile Ser Ile Leu Tyr Arg Lys
            500                 505                 510

Pro Asn Gly Thr Asn Pro Gly Val Phe Ser Phe Leu Asn Pro Leu Ser
            515                 520                 525

Pro Asp Ile Trp Met Tyr Xaa Leu Leu Ala Xaa Leu Gly Val Ser Cys
530                 535                 540                 545

Val Leu Phe Val Ile Ala Arg Phe Ser Pro Tyr Glu Trp Tyr Asn Pro
            550                 555                 560

His Pro Cys Asn Pro Asp Ser Asp Val Val Glu Asn Asn Phe Thr Leu
            565                 570                 575

Leu Asn Ser Phe Trp Phe Gly Val Gly Ala Leu Met Xaa Gln Gly Ser
            580                 585                 590

Glu Leu Met Pro Lys Ala Leu Ser Thr Arg Ile Val Gly Gly Ile Trp
            595                 600                 605

Trp Phe Phe Thr Leu Ile Ile Ile Ser Ser Tyr Thr Ala Asn Leu Ala
610                 615                 620                 625

Ala Phe Leu Thr Val Glu Arg Met Glu Ser Pro Ile Asp Ser Ala Asp
            630                 635                 640

Asp Leu Ala Lys Gln Thr Lys Ile Glu Tyr Gly Ala Val Glu Asp Gly
            645                 650                 655

Ala Thr Met Thr Phe Phe Lys Lys Ser Lys Ile Ser Thr Tyr Asp Lys
            660                 665                 670

Met Trp Ala Phe Met Ser Ser Arg Arg Gln Ser Val Leu Val Lys Ser
            675                 680                 685

Asn Glu Glu Gly Ile Gln Arg Val Leu Thr Ser Asp Tyr Ala Phe Leu
690                 695                 700                 705

Met Glu Ser Thr Thr Ile Glu Phe Val Thr Gln Arg Asn Cys Asn Leu
            710                 715                 720

Thr Gln Ile Gly Gly Leu Ile Asp Ser Lys Gly Tyr Gly Val Gly Thr
            725                 730                 735

Pro Met Gly Ser Pro Tyr Arg Asp Lys Ile Thr Ile Ala Ile Leu Gln
            740                 745                 750

Leu Gln Glu Glu Gly Lys Leu His Met Met Lys Glu Lys Trp Trp Arg
            755                 760                 765

Gly Asn Gly Cys Pro Glu Glu Ser Lys Glu Ala Ser Ala Leu Gly
770                 775                 780                 785

Val Gln Asn Ile Gly Gly Ile Phe Ile Val Leu Ala Ala Gly Leu Val
            790                 795                 800
```

```
Leu Ser Val Phe Val Ala Val Gly Glu Phe Leu Tyr Lys Ser Lys Lys
            805                 810                 815

Asn Ala Gln Leu Glu Lys Arg Ser Phe Cys Ser Ala Met Val Glu Glu
            820                 825                 830

Leu Arg Met Ser Leu Lys Cys Gln Arg Arg Leu Lys His Lys Pro Gln
            835                 840                 845

Ala Pro Val Ile Val Lys Thr Glu Glu Val Ile Asn Met His Thr Phe
850                 855                 860                 865

Asn Asp Arg Arg Leu Pro Gly Lys Glu Thr Met Ala
                870                 875

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

AACCTTGGCG AAATATCGCA TCC                                           23

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

GAGCCTCGGG ATATCTATCA TG                                            22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:17:

ACACACCTCC AACAATGCGC CC                                            22

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:18:

CTTGCAATCA CAAAGAGTAC ACAG                                          24
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:19:

CTGGTCGATA GAGCTTTGGG                                               20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

CTCCAAACCC TTCATGACCC                                               20

(2) INFORMATION FOR SEQ ID NO:21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

GGGAAAATAG CAGGCTGGAA TCGTATACCT TG                                 32

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

CCCTACGAGT GGTATAACCC C                                             21

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

GCTGACCTTG CAGTTGCTCC                                               20

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:24:

CCTGGCTATG ACAAAGAGCA C                                          21

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:25:

CTGGTGGACA GTGCTTTGGG                                           20

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:26:

GGCAAAATGG GCAACCGGTG TACCTTG                                27

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:27:

CCACACCCTT GCAACCCTGA                                           20

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:28:

AATGATGCGT GTGGACAGGG C                                          21

-continued (2) INFORMATION FOR SEQ ID NO:29:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:29:

CCCCTGACCA TCACCCATGT                                              20

(2) INFORMATION FOR SEQ ID NO:30:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:30:

CTGGCTCCGA GGTGGTGGAA                                              20

(2) INFORMATION FOR SEQ ID NO:31:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:31:

CCTTTGGGCA TCAGCACAGA C                                            21

(2) INFORMATION FOR SEQ ID NO:32:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:32:

CTGGCGATGA CGAAGAGGAC                                              20